(12) United States Patent
Rameshwar

(10) Patent No.: US 8,383,806 B2
(45) Date of Patent: Feb. 26, 2013

(54) METHOD OF REVERSING CARBOPLATIN RESISTANCE BY INHIBITION OF HGFIN

(75) Inventor: Pranela Rameshwar, Maplewood, NJ (US)

(73) Assignee: University of Medicine and Dentistry of New Jersey, Somerset, NJ (US)

( * ) Notice: Subject to any disclaimer, the term of this patent is extended or adjusted under 35 U.S.C. 154(b) by 0 days.

(21) Appl. No.: 13/085,612

(22) Filed: Apr. 13, 2011

(65) Prior Publication Data

US 2011/0237519 A1 Sep. 29, 2011

Related U.S. Application Data

(63) Continuation-in-part of application No. 11/782,185, filed on Jul. 24, 2007, which is a continuation-in-part of application No. 10/463,106, filed on Jun. 17, 2003, now abandoned, which is a continuation-in-part of application No. 10/039,272, filed on Oct. 20, 2001, now Pat. No. 6,939,955.

(60) Provisional application No. 60/241,881, filed on Oct. 20, 2000.

(51) Int. Cl.
*C07H 21/02* (2006.01)
*A61K 39/00* (2006.01)

(52) U.S. Cl. .................... 536/24.5; 536/23.1; 424/198.1

(58) Field of Classification Search .................. None
See application file for complete search history.

(56) References Cited

U.S. PATENT DOCUMENTS

2002/0151486 A1* 10/2002 Popoff et al. .................. 514/12

OTHER PUBLICATIONS

Gura, T. Systems for identifying new drugs are often faulty. Science, 1997, vol. 278, p. 1041-1042.*
Rose, A.A.N. Osteoactivin promotes breast cancer metastasis to bone. Molecular Cancer Research, 2007, vol. 5, No. 10, p. 1001-1014.*
Rose, A.A.N. Glycoprotein nonmetastatic B is an independent prognostic indicator of recurrence and a novel therapeutic taret in breast cancer. Clinicial Cancer Research, 2010, vol. 16, No. 7, p. 2147-2156.*
Aalto et al. "Enhanced Expression of Neuropeptides in Human Breast Cancer Cell Lines Following Irradiation" Peptides 1998 19(2):231-239.
Abrahams et al. "Cyclic AMP Regulates the Expression of Neurokinin₁ Receptors by Neonatal Rat Spinal Neurons in Culture" Journal of Neurochemistry 1999 73:50-58.
Adamus, M. A. and Dabrowski, Z. J. "Effect of the Neuropeptide Substance P on the Rat Bone Marrow-derived Osteogenic Cells in Vitro" Journal of Cellular Biochemistry 2001 81:499-506.
Akashi et al. "A Clonogenic Common Myeloid Progenitor that Gives Rise to All Myeloid Lineages" Nature 2000 404:193-197.

Bandari et al. "Hematopoietic Growth Factor Inducible Neurokinin-1 Type: a Transmembrane Protein That is Similar to Neurokinin 1 Interacts with Substance P" Regulatory Peptides 2003 111:169-178.
Begley et al. "Primary Human Myeloid Leukemia Cells: Comparative Responsiveness to Proliferative Stimulation by GM-CSF or G-CSF and Membrane Expression of CSF Receptors" Leukemia 1987 1(1):1-8.
Bianco et al. "Bone Marrow Stromal Stem Cells: Nature, Biology, and Potential Applications" Stem Cells 2001 19:180-192.
Biggs et al. "A Human Id-like Helix-Loop-Helix Protein Expressed during Early Development" Proceedings of the National Academy of the Sciences USA 1992 89:1512-1516.
Brekken, R. A. and Sage, E. H. "SPARC, a Matricellular Protein: At the Crossroads of Cell-matrix Communication" Matrix Biology 2000 19:816-827.
Cooper, C. L. and Newburger, P. E. "Differential Expression of Id Genes in Multipotent Myeloid Progenitor Cells: Id-1 Is Induced by Early- and Late-Acting Cytokines While Id-2 is Selectively Induced by Cytokines That Drive Terminal Granulocytic Differentiation" Journal of Cellular Biochemistry 1998 71:277-285.
Fan et al. "Stimulation of Angiogenesis by Substance P and Interleukin-1 in the Rat and Its Inhibition by $NK_1$ or Interleukin-1 Receptor Antagonists" British Journal of Pharmacology 1993 110:43-49.
Freedman, A. S. "Immunobiology of Chronic Lymphocytic Leukemia" Hematology/Oncology Clinics of North America 1990 4(2):405-429.
Gerard et al. "Human Substance P Receptor (NK-1): Organization of the Gene, Chromosome Localization and Functional Expression of cDNA Clones" Biochemistry 1991 30:10640-10646.
Glück, S. "Autologous Transplantation for Patients with Advanced Breast Cancer with Emphasis on Bony Metastasis" Supplement of the Canadian Journal of Oncology 1995 1:58-62.
Hegde et al. "c-Maf Induces Monocytic Differentiation and Apoptosis in Bipotent Myeloid Progenitors" Blood 1999 94(5):1578-1589.
Ho et al. "Human Monocytes and Macrophages Express Substance P and Neurokinin-1 Receptor" The Journal of Immunology 1997 159:5654-5660.
Ishiguro et al. "Id2 Expression Increases With Differentiation of Human Myeloid Cells" Blood 1996 87(12):5225-5231.
King et al. "Lineage Infidelity in Myeloid Cells with TCR Gene Rearrangement: A Latent Developmental Potential of proT Cells Revealed by Ectopic Cytokine Receptor Signaling" Proceedings of the National Academy of the Sciences USA 2002 99(7):4508-4513.
Krause et al. "Structure, Functions and Mechanisms of Substance P Receptor Action" Journal of Investigative Dermatology 1992 98(6):2S-7S.
Little, M. and Storb, R. "History of Haematopoietic Stem-cell Transplantation" Nature Reviews 2002 2:231-238.

(Continued)

*Primary Examiner* — Robert Landsman
*Assistant Examiner* — Bruce D Hissong
(74) *Attorney, Agent, or Firm* — Licata & Tyrrell P.C.

(57) ABSTRACT

The present invention discloses the cloning of a new cDNA, HGFIN, from stimulated bone marrow stromal cells that was retrieved with a probe specific for the neurokinin-1 (NK-1) receptor. The novel gene, HGFIN, encodes a protein receptor that is involved in the regulation of hematopoietic proliferation and differentiation. HGFIN is implicated in the treatment of hyperproliferative disorders, particularly bone and breast cancer, because it acts to suppress the proliferating cells.

1 Claim, 8 Drawing Sheets

OTHER PUBLICATIONS

Maggi, C. A. "Tachykinins in the Autonomic Nervous System" Pharmacological Research 1996 33(3):161-170.

Malawer, M. M. and Delaney, T. F. Cancer. *Principles & Practice of Oncology*. Philadelphia: J.B. Lippincott Company, 1993. pp. 2225-2245.

Massari, M. E. and Murre, C. "Helix-Loop-Helix Proteins: Regulators of Transcription in Eucaryotic Organisms" Molecular and Cellular Biology 2000 20(2):429-440.

Metcalf, D. "The Molecular Control of Cell Division, Differentiation Commitment and Maturation in Haemopoietic Cells" Nature 1989 339:27-30.

Miura et al. "Pyk2 and Syk Participate in Functional Activation of Granulocytic HL-60 Cells in a Different Manner" Blood 2000 96(5):1733-1739.

Müller-Sieburg, C. E. and Deryugina, E. "The Stromal Cells' Guide to the Stem Cell Universe" Stem Cells 1995 13:477-486.

Nagata (1990) "Peptide Growth Factors and Their Receptors", *Handbook of Experimental Pharmacology*, eds. Sporn & Roberts, Spring-Verlag, Heidelberg, vol. 95/1, pp. 699-722.

Nicola, N.A. "Hemopoietic Cell Growth Factors and Their Receptors" Annual Review of Biochemistry 1989 58:45-77.

Nicola, N. A. and Metcalf, D. "Binding of the Differentiation-Inducer, Granulocyte-Colony-Stimulating Factor, to Responsive but not Unresponsive Leukemic Cell Lines" Proceedings of the National Academy of the Sciences USA 1984 81:3765-3769.

Norton et al. "Id Helix—Loop—Helix Proteins in Cell Growth and Differentiation" Trends in Cell Biology 1998 8:58-65.

Punzel et al. "Functional Analysis of Initial Cell Divisions Defines the Subsequent Fate of Individual Human $CD34^+CD38^-$ Cells" Experimental Hematology 2002 30:464-472.

Qian et al. "Cloning of Human Preprotachykinin-I Promoter and the Role of Cyclic Adenosine 5'-Monophosphate Response Elements in its Expression by IL-1 and Stem Cell Factor" The Journal of Immunology 2001 166:2553-2561.

Qian et al. "Induction of Hypoxia-Inducible Factor-$1\alpha$ and Activation of Caspase-3 in Hypoxia-Reoxygenated Bone Marrow Stroma Is Negatively Regulated by the Delayed Production of Substance P" The Journal of Immunology 2001 167:4600-4608.

Quinn et al. "Molecular Models to Analyse Preprotachykinin-A Expression and Function" Neuropeptides 2000 34(5):292-302.

Rameshwar et al. "Hematopoietic Regulation Mediated by Interactions among the Neurokinins and Cytokines" Leukemia and Lymphoma 1997 28:1-10.

Rameshwar et al. "Mimicry between Neurokinin-1 and Fibronectin May Explain the Transport and Stability of Increased Substance P Immunoreactivity in Patients with Bone Marrow Fibrosis" Blood 2001 97(10):3025-3031.

Rameshwar et al. "Receptor Induction Regulates the Synergistic Effects of Substance P with IL-1 and Platelet-Derived Growth Factor on the Proliferation of Bone Marrow Fibroblasts" The Journal of Immunology 1997 158:3417-3424.

Rameshwar, P. "Substance P: a Regulatory Neuropeptide for Hematopoiesis and Immune Functions" Clinical Immunology and Immunopathology 1997 85(2):129-133.

Rameshwar, P. and Gascón, P. "Hematopoietic Modulation by the Tachykinins" Acta Haematologica 1997 98:59-63.

Randall, T. D. and Weissman, I. L. "Characterization of a Population of Cells in the Bone Marrow that Phenotypically Mimics Hematopoietic Stem Cells: Resting Stem Cells or Mystery Population?" Stem Cells 1998 16:38-48.

Reeve, J. G. and Bleehen, N. M. "[D-$Arg^1$, D-$Phe^5$, D-$Trp^{7,9}$, $Leu^{11}$] Substance P Induces Apoptosis in Lung Cancer Cell Lines in Vitro" Biochemical and Biophysical Research Communications 1994 199(3):1313-1319.

Rich et al. "Bone-related Genes Expressed in Advanced Malignancies Induce Invasion and Metastasis in a Genetically Defined Human Cancer Model" The Journal of Biological Chemistry 2003 278(18):15951-15957.

Roodman, G. D. "Cell Biology of the Osteoclast" Experimental Hematology 1999 27:1229-1241.

Spits et al. "Early Stages in the Development of Human T, Natural Killer and Thymic Dendritic Cells" Immunological Reviews 1998 165:75-86.

Weterman et al. "*nmb*, A Novel Gene, Is Expressed in Low-metastatic Human Melanoma Cell Lines and Xenografts" International Journal of Cancer 1995 60:73-81.

Yao et al. "Neurokinin-1 Expression and Co-Localization with Glutamate and GABA in the Hypothalamus of the Cat" Molecular Brain Research 1999 71:149-158.

Zon, L. I. "Developmental Biology of Hematopoiesis" Blood 1995 86(8):2876-2891.

\* cited by examiner

```
  1  MECLYYFLGF  LLLAARLPLD  AAKRFHDVLG
 31  NERPSAYMRE  HNQLNGWSSD  ENDWNEKLYP
 61  VWKRGDMRKW  NSWKGGRVQA  VLTSDSPALV
 91  GSNITFAVNL  IFPRCQKEDA  NGNIVYEKNC
121  RNEAGLSADP  YVYNWTAWSE  DSDGENGTGQ
151  SHHNVFPDGK  PFPHHPGWRR  WNFIYVFHTL
181  GQYFQKLGRC  SVRVSVNTAN  VTLGPQLMEV
211  TVYRRHGRAY  VPIAQVKDVY  VVTDQIPVFV
241  TMFQKNDRNS  SDETFLKDLP  IMFDVLIHDP
271  SHFLNYSTIN  YKWSFGDNTG  LFVSTNHTVN
301  HTYVLNGTFS  LNLTVKAAAP  GPCPPPPPPP
331  RPSKPTPSLG  PAGDNPLELS  RIPDENCQIN
361  RYGHFQATIT  IVEGILEVNI  IQMTDVLMPV
391  PWPESSLIDF  VVTCQGSIPT  EVCTIISDPT
421  CEITQNTVCS  PVDVDEMCLL  TVRRTFNGSG
451  TYCVNLTLGD  DTSLALTSTL  ISVPDRDPAS
481  PLRMansali  svgclaifvt  visllvykkh
511  KEYNPIENSP  GNVVRSKGLS  VFLNRAKAVF
541  FPGNQEKDPL  LKNQEFKGVS
```

RGD = CELL ADHESION REGION

*N = ASN GLYCOSYLATION SITE

ITALIC = PKD REGION

LOWERCASE = TRANSMEMBRANE

*FIG. 1B*

METHOD OF REVERSING CARBOPLATIN RESISTANCE BY INHIBITION OF HGFIN

INTRODUCTION

This application is a continuation-in-part application of U.S. patent application Ser. No. 11/782,185 filed Jul. 24, 2007, which is a continuation-in-part of U.S. patent application Ser. No. 10/463,106, filed Jun. 17, 2003, now abandoned, which is a continuation-in-part of U.S. patent application Ser. No. 10/039,272, filed Oct. 20, 2001, now U.S. Pat. No. 6,939,955, which claims priority to provisional patent application U.S. Ser. No. 60/241,881, filed Oct. 20, 2000, the disclosures of which are incorporated by reference in their entirety herein.

This invention was made with government support under Grant Nos: HL-54973 and HL-57675 awarded by the National Institute of Health and Grant No. CA89868 awarded by the National Cancer Institute. The government has certain rights in the present invention.

BACKGROUND OF THE INVENTION

Bone Marrow is the major source of both lymphocytes (immune cells) and erythrocytes in the adult. Among the various cells that constitute the bone marrow are primitive hematopoietic pluripotent stem cells and progenitor cells. An important property of stem cells is their ability to both proliferate, which ensures a continuous supply throughout the lifetime of an individual, and differentiate into the mature cells of the peripheral blood system. When necessary, a pluripotent stem cell can begin to differentiate, and after successive divisions become committed, thus losing the capacity for self-renewal, to a particular line of development. All of the circulating blood cells, including erythrocytes, leukocytes or lymphocytes, granulocytes and platelets originate from various progenitor cells that are themselves derived from precursor stem cells.

The morphologically recognizable and functionally capable cells circulating in the blood include erythrocytes (red blood cells), leukocytes (white blood cells including both B and T cells), non B- and T-lymphocytes, phagocytes, neutrophilic, eosinophilic and basophilic granulocytes, and platelets. These mature cells are derived, on demand, from dividing progenitor cells, such as erythroblasts (for erythrocytes), lymphoid precursors, myeloblasts (for phagocytes including monocytes, macrophages and neutrophils), promyelocytes and myelocytes (for the various granulocytes) and megakaryocytes for the platelets. As stated above, these progenitor cells are themselves derived from precursor stem cells.

A complex network of soluble factors as well as inter- and intra-cellular interactions regulate the proliferation and differentiation of a finite pool of hematopoietic stem cells (HSC). Adult bone marrow consists of a finite number of self-renewing HSCs that replenish the immune system throughout life. Proliferation and differentiation of hematopoietic cells are regulated by hormone-like growth and differentiation factors designated as colony-stimulating factors (CSF) (Metcalf (1989) Nature 339:27-30). CSF can be classified into several factors according to the stage of the hematopoietic cells to be stimulated and the surrounding conditions as follows: granulocyte colony-stimulation factor (G-CSF), granulocyte-macrophage colony-stimulation factor (GM-CSF), macrophage colony-stimulation factor (M-CSF), and interleukin 3 (IL-3). Hematopoiesis is also regulated by inter-cellular and intra-cellular interactions that involve several adhesion molecules.

The stromal cells are a major compartment of the bone marrow microenvironment. These cells exert functional plasticity by producing molecules that belong to classes that include cytokines, neurotrophic factors, neuropeptides and extracellular matrix proteins. Stromal cells provide a niche for HSC at a site close to the endosteal region. At this site, the oxygen level is the lowest in the bone marrow and perhaps, HSC could be protected from oxygen radicals, insults from chemical compounds and from other insults.

Small amounts of certain hematopoietic growth factors account for the differentiation of stem cells into a variety of blood cell progenitors, for the tremendous proliferation of those cells, and for their differentiation into mature blood cells. For instance, G-CSF participates greatly in the differentiation and growth of neutrophilic granulocytes and plays an important role in the regulation of blood levels of neutrophils and the activation of mature neutrophils (Nagata (1990) "Handbook of Experimental Pharmacology", volume "Peptide Growth Factors and Their Receptors", eds. Sporn & Roberts, Spring-Verlag, Heidelberg, Vol. 95/1, pp. 699-722; Nicola, et al. (1989) *Annu. Rev. Biochem.* 58:45-77). It is also reported that G-CSF stimulates the growth of tumor cells such as myeloid leukemia cells (Nicola & Metcalf (1984) *Proc. Natl. Acad. Sci. USA* 81:3765-3769; Begley et al. (1987) *Leukemia* 1:1-8). Other growth factors include, erythropoietin (EPO), which is responsible for stimulating the differentiation of erythroblasts into erythrocytes and M-CSF responsible for stimulating the differentiation of myeloblasts and myelocytes into monocytes.

Growth factors are part of a family of chemical messengers known as the cytokines. Cytokines are among the factors that act upon the hematopoietic system to regulate blood cell proliferation and differentiation. Cytokines are also important mediators of the immune response being secreted by both B and T cells, as well as other various lymphocytes. Cytokines encourage cell growth, promote cell activation, direct cellular traffic, act as messengers between cells of the hematopoietic system, and destroy target cells (i.e., cancer cells). Tachykinins are among the various components involved in the modulation and regulation of the hematopoietic system that cytokines play a role in modulating.

The tachykinins are immune and hematopoietic modulators that belong to a family of peptides encoded by a single copy of the evolutionarily conserved preprotachykinin-I (PPT-1) gene (Quinn, et al. (2000) *Neuropeptides* 34:292-302). PPT-1 is alternatively spliced into four possible transcripts and is ubiquitously expressed. The tachykinins can be released in the bone marrow and other lymphoid organs as neurotransmitters or from the resident bone marrow immune cells (Rameshwar (1997) supra; Ho, et al. (1997) *J. Immunol.* 159:5654-5660; Maggi (1996) *Pharmacol. Res.* 33:161-170; 2-6). In the bone marrow, PPT-1 and other hematopoietic growth factors regulate expression of each other through autocrine and paracrine activities. It is believed that various cytokines induce the expression of the PPT-1 gene in bone marrow mesenchymal cells (Rameshwar (1997) supra). The tachykinin family of peptides exerts pleiotropic functions such as neurotransmission and immune/hematopoietic modulation.

PPT-1 peptides exert both stimulatory and inhibitory hematopoietic effects by interacting with different affinities to the G-protein coupled receptors: NK-1, NK-2 and NK-3 (Krause, et al. (1992) *J. Invest. Dermatol.* 98:2S-7S). NK-1 and NK-2 expression has been reported in bone marrow cells (Rameshwar, et al. (1997) *Leuk. Lymphoma* 28:1-10), whereas NK-3 has not been detected. NK-1 is induced in bone marrow cells by cytokines and other stimulatory hematopoietic regulators. NK-2 is constitutively expressed in bone marrow cells that are unstimulated or stimulated with suppressive hematopoietic regulators. NK-1 and NK-2 are not co-expressed in bone marrow cells because NK-1 induction by cytokines is correlated with the down regulation of NK-2. NK-1 and NK-2 are co-expressed in breast cancer, however. In bone marrow cells, NK-1 expression requires cell stimulation whereas its expression in neural tissue is constitutive (Rameshwar (1997) supra; Yao, et al. (1999) *Mol. Brain. Res.* 71:149-158; Abrahams, et al. (1999) *J. Neurochem.* 73:50-58). It is believed that a particular cytokine discriminates between the expression of NK-1 and NK-2, which directs the type of bone marrow functions: stimulatory vs. inhibitory (Rameshwar, et al. (1997) supra).

PPT-1 is constitutively expressed in several cancers including breast cancer (Singh, et al. (2000) *Proc. Natl. Acad. Sci. USA* 97:388-393), but its expression requires induction in normal mammary epithelial cells (Rameshwar, et al. (1997) supra; Rameshwar & Gascon (1997) *Acta Haematol.* 98:59; Qian et al. (2001) *J. Immunol.* 166:2553). PPT-1 peptides protect cancer cells from radiation damage (Aalto et al. (1998) *Peptides* 19:231), prevent apoptosis (Reeve et al. (1994) *Biochem. Biophy. Res. Comm.* 199:1313), enhance breast cancer cell proliferation (Miura, et al. (2000) *Blood* 96:1733-1739) and could be produced by hypoxia (Fan et al. (1993) *Br. J. Pharmacol.* 110:43; Qian et al. (2001) *J. Immunol.* 167:4600). The association between PPT-1 overexpression in cancers that show preference for bone marrow (Gluck (1995) *Canadian J. Oncol.* 1:58; Malawer & Delaney (1993) In *Cancer. Principles and Practice of Oncology*. DeVita et al. (eds.) J. B. Lippincott, Philadelphia, p 2225) could provide insights into bone marrow metastasis.

Substance P (SP), the major tachykinin released in the bone marrow, stimulates hematopoiesis through interactions with the neurokinin-1 (NK-1) receptor, which is resident on bone marrow stroma, immune cells and other lymphoid organ cells. Hence, the expression of NK-1 determines the hematopoietic response of the tachykinins. NK-2 inhibits hematopoiesis by interacting with neurokinin-A, another tachykinin encoded for by the PPT-1 gene. The present inventors have discovered that the stimulatory effects mediated by NK-1 can be changed to hematopoietic inhibition in the presence of the amino terminal of SP, a fragment found endogenously in the bone marrow due to enzymatic digestion of SP by endogenous endopeptidases. Further, dysregulated expression of the PPT-1 gene has been associated with different pathologies such as cancer.

Typically, cancer is due to failure of the immune surveillance system in an individual. Even immunocompetent individuals can succumb to aggressive tumors. However, most endocrine cancers (such as cervical, neuroblastoma, breast, prostate), lung and colon cancers have homing preference for the bone marrow, although breast cancer is linked predominantly to bone marrow. Breast cancer metastasis to the bone marrow is a clinical dilemma since the prognosis for the patient is generally poor. Through the functioning presence of different families of growth factors and other molecules, the bone marrow microenvironment is conducive to the survival and transient changes of breast cancer cell function from an aggressive type tumor cell to a more benign-type cell. This reduction in short-term aggression is part of what allow the breast cancer cell to survive and remain undetectable in the bone marrow for prolonged periods.

Despite the emphasis on regular mammograms and self-examination, a breast cancer patient could present with metastasis with cells from the bone marrow to tertiary site for up to ten years after the start of remission. A major reason for breast cancer evasion in the bone marrow is that therapeutic intensity is limited by toxicity to the finite and limited number of hematopoietic stem cells in the bone marrow. It is believed that breast cancer cells are located in the marrow compartment during early phase of cancer and during remission. The cancer cells from the marrow can invade the bone and other distant organs during metastasis. To develop proper drugs to target cancer cells, two areas of cancer entry to the marrow could be targeted: during entry and at "seeding."

Breast cancer cells have shown increased expression of PPT-1 and its receptor NK-1 as compared to normal mammary epithelial cells. Specific NK-1 antagonists have inhibited breast cancer cell proliferation, suggesting autocrine and/or intercrine stimulation of breast cancer cells by PPT-1 peptides. Thus, PPT-1 and NK-1 are thought to be important in breast cancer development. Further, since PPT-1 peptides are considered hematopoietic modulators, the relationship of PPT-1 peptides and NK-1 receptor with breast cancer may assist in understanding the early integration of breast cancer cells in the bone marrow (Rameshwar, et al. (2000) *Proc. Natl. Acad. Sci. USA* 97: 388-393).

Under normal circumstances, the bone marrow is able to respond quickly to an increased demand for a particular type of cell. The pluripotential stem cell is capable of creating and reconstituting all the cells that circulate in the blood, including both red and white blood cells and platelets. As stated, progenitor cells that derive from stem cells can replicate and differentiate at an astounding, if not alarming rate. On average, 3-10 billion lymphocyte cells can be generated in an hour. The bone marrow can increase this by ten-fold in response to need. However, in the throes of a diseased state, the bone marrow may not produce enough stem cells, may produce too many stem cells or various ones produced may begin to proliferate uncontrollably. Further complications arise when these stem cells or their associated progenitors are not able to differentiate into the various morphologically recognizable and functionally capable cells circulating in the blood.

Lymphoproliferative syndromes consist of types of diseases known as leukemia and malignant lymphoma, which can further be classified as acute and chronic myeloid or lymphocytic leukemia, Hodgkin's lymphoma, and non-Hodgkin's lymphoma. These diseases are characterized by the uncontrollable multiplication or proliferation of leukocytes (primarily the B-cells) and tissue of the lymphatic system, especially lymphocyte cells produced in the bone marrow and lymph nodes.

Lymphocytes (also called leukocytes) are core components of the body's immune system, which is one of the principal mechanisms by which the body attacks and controls cancers. Lymphocytes, or their derivatives, recognize the foreign antigenic nature of cancer cells or of antibodies associated therewith and attack the cancer cells. Upon exposure to a foreign antigen in the human body, lymphocytes naturally proliferate or multiply to combat the antigen.

B and T cells are two broad sub-types of lymphocyte cells, derived from the bone marrow. T cells undergo a process of maturation in the thymus gland. Mature lymphocytes all have a similar appearance. They are small cells with a deeply basophilic nucleus and scanty cytoplasm. B and T cells circulate in the blood and through body tissues. B cells primarily work by secreting soluble substances called antibodies. Each B cell is programmed to make one specific antibody. When a B cell encounters its triggering antigen, it goes through a process wherein it is changed into many large plasma cells. Hence, B cells give rise to plasma cells, which secrete a specific immunoglobulin (antibodies). T cells also respond to antigens. Some of them (CD4+) secrete lymphokines that act on other cells, thus regulating the complex workings of the immune response. Others (CD8+, cytotoxic) directly contact infected cells and are able to cause lysis thereby destroying the infected cells.

Leukemia and other such B-cell malignancies, such as acute and chronic myeloid and lymphocytic leukemia as well as the B-cell subtype of Hodgkins and non-Hodgkin's lymphoma, are examples of lymphoproliferative syndromes that are significant contributors to cancer mortality. In fact, the majority of chronic lymphocytic leukemias are of B-cell lineage (Freedman (1990) *Hematol. Oncol. Clin. North Am.* 4:405).

Leukemia can be defined as the uncontrolled proliferation of a clone of abnormal hematopoietic cells. Leukemias are further typically characterized as being myelocytic or lymphocytic. Myeloid leukemias affect the descendents of the myeloid lineage, whereas the lymphocytic leukemias involve abnormalities in the lymphoid lineage. Most B cell leukemias and lymphomas are monoclonal, meaning that all of the related tumor cells are derived from one particular aberrant cell.

Generally, leukemia is a neoplastic disease in which white corpuscle maturation is arrested at a primitive stage of cell development. The disease is characterized by an increased number of leukemic blast cells in the bone marrow and by varying degrees of failure to produce normal hematopoietic cells. The condition may be either acute or chronic. Acute myelocytic leukemia (AML) arises from bone marrow hematopoietic stem cells or their progeny. The term "acute myelocytic leukemia" subsumes several subtypes of leukemia, e.g., myeloblastic leukemia, promyelocytic leukemia and myelomonocytic leukemia and is a form of cancer that affects the cells producing myeloid blood cells in the bone marrow. As stated above, myeloid cells are red blood cells, platelets and all white blood cells (which include: neutrophils, monocytes, macrophages, eosinophils and basophils). Primarily, AML involves abnormal white blood cells of the neutrophil type. Production of blood cells is obstructed and immature cells known as "blast cells" accumulate in the bone marrow. These cells are unable to mature and differentiate properly leading to a significant reduction of normal blood cells in the circulation. The accumulation of blast cells in the bone marrow prevents production of other cell types resulting in anemia and low platelet blood counts. Acute lymphocytic leukemia (ALL) arises in lymphoid tissues and ordinarily first manifests its presence in bone marrow. ALL is primarily a form of cancer that affects the lymphocytes and lymphocyte-producing cells in the bone marrow.

Chronic myelogenous leukemia (CML) is characterized by abnormal proliferation of immature granulocytes, for example, neutrophils, eosinophils and basophils, in the blood, bone marrow, the spleen, liver and sometimes in other tissues. A large portion of chronic myelogenous leukemia patients develop a transformation into a pattern indistinguishable from the acute form of the disease.

This change is known as the "blast crises". Chronic lymphocytic leukemia (CLL) is a form of leukemia in which there is an excess number of mature, but poorly functioning, lymphocytes in the circulating blood. It is to be noted that the rate of production of lymphocytes is not significantly increased and may in fact even be slower than normal. CLL has several phases. In the early phase, it is characterized by the accumulation of small, mature functionally-incompetent malignant B-cells having a lengthened life span. The late stages of CLL are characterized by significant anemia and/or thrombocytopenia.

The two main types of lymphoma are Hodgkin's and non-Hodgkin's lymphoma. Hodgkin's disease is a cancer of the lymphatic system, the network of lymph glands and channels that occurs throughout the body. The defining feature of Hodgkin's disease is the presence of a distinctive abnormal lymphocyte called a Reed-Sternberg cell. There are five. recognized sub-groups of Hodgkin's disease including lymphocyte rich, nodular sclerosing, mixed cellularity, lymphocyte depleted and nodular lymphocyte predominant (which predominantly affects one isolated lymph node). All other types of lymphoma are collectively known as non-Hodgkin's lymphoma. There are thirty sub-types of non-Hodgkin's type lymphoma.

Traditional methods of treating these B-cell malignancies, which include chemotherapy and radiotherapy, have limited utility due to toxic side effects. Short-term side effects of chemotherapy may include significant toxicity, extreme nausea, vomiting, and serious discomfort. The long-term side effects may include diabetes, other forms of B-cell malignancies, other forms of cancer, heart, lung or other organ disease, fatal bleeding during remission induction, and myelodysplasia. The short-term side effects of radiotherapy may include extreme nausea, vomiting, serious discomfort, sterility and infertility. The long-term side effects of radiotherapy may include other forms of B-cell malignancies, cancer, thyroid gland, spleen or other organ failure. These side effects may be moderated by reduced dosages, however, this also increases the risk of remission.

Another traditional method for treating B-cell malignancies includes either bone marrow or stem cell transplantation. However, these procedures are plagued with exorbitant cost and high rates of failure. It is both difficult and costly to locate a sufficient donor and even when one is located, rejection of the transplanted cells often takes place, which in turn can lead to graft versus host disease. Most often, these treatments also include a combination of both chemo and radiotherapies, hence, the concomitant risks involved therein would apply here as well.

There is, therefore, a need for a more non-evasive treatment for lymphoproliferative diseases related to either an increase or decrease in differentiation, as well as uncontrolled proliferation. The present invention meets this need in the art.

SUMMARY OF THE INVENTION

The present invention involves a novel gene, its antisense polynucleotide sequence, the coded for protein and antibodies immunospecific to the coded for protein. More particularly, the present invention provides pharmaceutical compositions of the novel gene, its antisense sequence, the protein and/or antibodies immunospecific to the protein, which can be used to either increase or decrease lymphocyte differentiation and may be useful in inhibiting white blood cell proliferation. The present invention can be used to treat hyperproliferative diseases such as bone and breast cancer, blood vessel proliferative disorder, fibrotic disorder, or the rejection of transplanted material. The present invention is especially suited for treating breast cancer.

Hence, the methods of the present invention are useful for the prevention and treatment of lymphoproliferative syndromes such as B-cell related maladies, including but not limited to acute and chronic myeloid and lymphocytic leukemia as well as the B-cell subtype of Hodgkin's and non- Hodgkin's lymphomas. The methods of the present invention are further directed to inhibition of cancer cell growth in a variety of cancers including but not limited to breast cancer, as well as treatment of cancer in patients with breast cancer. Further, the methods of the present invention can be used to increase the effectiveness of both chemo- and radiotherapy. Further still, the use of monoclonal antibodies, in conjunction with the gene, antisense polynucleotide or protein of the present invention, to direct radionuclides, toxins, or other therapeutic agents offers the possibility that such agents can be delivered at lower dosages, selectively to tumor sites, thus limiting toxicity to normal tissues. Finally, the present invention is a method for reversing the resistance of cancer cells to chemotherapeutic drug treatment which comprises inhibiting the activity of HGFIN in tumor cells before treatment with a drug to which the cells have become resistant, a method that is based on a role for HGFIN to induce cancer stem cell differentiation.

BRIEF DESCRIPTION OF THE DRAWINGS

FIG. 1 is a diagram of the putative structure for HGFIN protein based on information provided by PredictProtein. FIG. 1B is a sequence annotation for regions within the HGFIN protein (SEQ ID NO:2).

FIG. 3 shows the results of transformation of HGFIN in MCF12A. Five-day clonogenic assays were performed in methylcellulose with MCF-12A cells, untransfected, HGFIN knockdown or stably transfected with pPMSKH1, or pPM-SKH1-HGFIN siRNA.

FIG. 6 shows role of Exon 1 in the activity of 5' flanking region of HGFIN.

FIG. 7 shows HGFIN reporter gene activity in MDA-MDB-231, ectopically expressed for p53.

DETAILED DESCRIPTION OF THE INVENTION

The bone marrow is the major organ where immune cells are derived. Homeostasis in the bone marrow is maintained by inter- and intra-cellular interactions by the various subsets of bone marrow cells. An understanding of normal bone marrow functions has been extended to unravel a novel mechanism of bone marrow-derived diseases such as leukemia and lymphoma. The present invention discloses the cloning of a new cDNA from stimulated bone marrow stromal cells that was retrieved with a probe specific for the neurokinin-1 (NK-1) receptor. The cloned cDNA was designated 'Hematopoietic Growth Factor Inducible Neurokinin-1 type' (HGFIN) gene based on its expression in differentiated hematopoietic cells, undetectable levels in the corresponding progenitors, and the concomitant down regulation of Id2, an inhibitor of cell differentiation.

When HGFIN expression is down-regulated in differentiated cells that were stimulated with the mitogen lipopolysaccharide, HGFIN can be an inhibitor of cell activation. This is in contrast to its effect in mesenchymal bone marrow cells in which HGFIN is induced by cytokines and a neurotrophic factor. Since bone marrow mesenchymal cells support hematopoiesis and are involved in bone remodeling, these data show that HGFIN can be involved in bone marrow functions throughout the hematopoietic hierarchy.

These discoveries have led to the compositions and methods of the present invention. Hence, the present invention provides a novel gene, HGFIN, which encodes a protein receptor that is involved in the regulation of hematopoietic proliferation and differentiation, and appears to act as a negative regulator of the Id2 protein. The protein of the present invention appears to be involved as a central mediator of white blood cell, progenitor, differentiation, and therefore, is useful in the prevention and treatment of lymphoproliferative syndromes such as B-cell related maladies, including but not limited to acute and chronic myeloid and lymphocytic leukemia as well as the B-cell subtype of Hodgkin's and non-Hodgkin's lymphomas.

In another embodiment, HGFIN can be used in controlling breast cancer. HGFIN and HGFIN-specific agonists can be used to inhibit breast cancer cell proliferation. The present studies of HGFIN expression in breast cancer cells (primary and cell lines) show that HGFIN is a tumor suppressor gene. The role of HGFIN as a tumor suppressor is underscored by experiments with siRNA specific for HGFIN in non-transformed mammary epithelial cells. HGFIN is highly expressed in the latter cells. Deficiency of HGFIN in non-transformed cells results in loss of contact for their growth, again indicating a role for HGFIN as a tumor suppressor gene.

Figure 8:
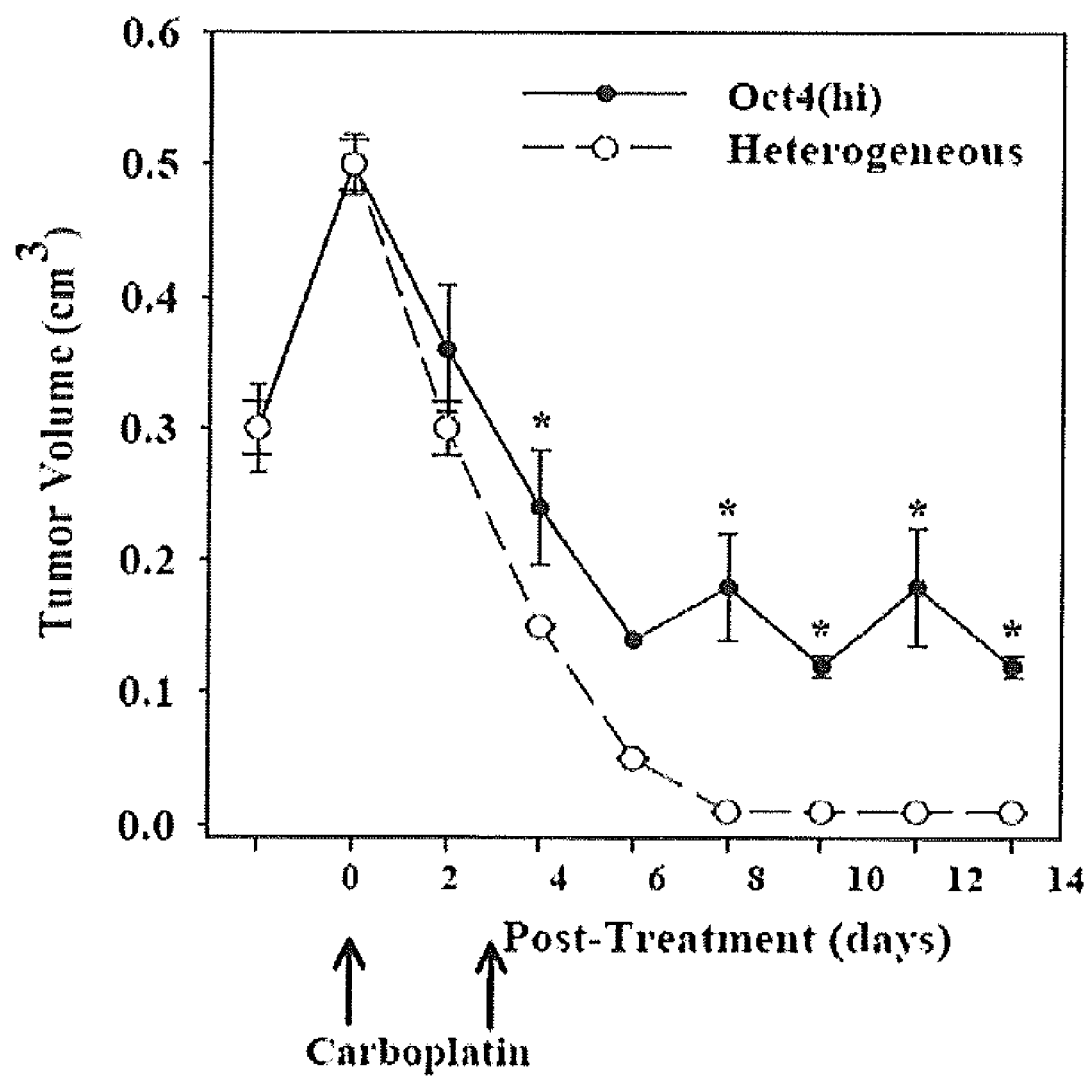
FIG. 8 depicts the effects of carboplatin treatment on tumor cell volume in vivo in mice. Two weeks after a second carboplatin injection (50 mg/kg), there were statistically significant decreases in tumor cell volume in Oct4 (+) breast cancer cells that expressed hi levels of HGFIN (Oct4(hi)), as compared to tumor cell volume before carboplatin treatment.

In yet another embodiment, HGFIN can be used in a method of reversing chemotherapeutic drug resistance. It has now been found that due to the role of HGFIN activity differentiation of stem cells, inhibition of HGFIN activity in cancer cells can lead to reversal of chemotherapeutic drug resistance in these cells (FIG. 8). Thus, the present invention includes a method for reversing chemotherapeutic drug resistance in cancer cells which comprises contacting the cancer cells with agents that inhibit the activity of HGFIN or decrease HGFIN gene expression. In a preferred embodiment, the cancer cells are breast cancer cells and the drug is carboplatin. The role of HGFIN to affect drug resistance is consistent with the role of HGFIN to affect stem cell differentiation as has been shown in hematopoietic cells.

The present disclosure further provides that HGFIN gene has a consensus sequence that binds to p53, collaborating the finding of a link between HGFIN and hematopoietic cell differentiation. In the latter state, the cells are in G0/G1 phase of the cell cycle, which could be mediated by the multiple p53 sites in the regulatory region of HGFIN. Until the discoveries of the present invention, an understanding of role of HGFIN in cancer was scant. A gene, similar to HGFIN, nmb, confers low metastatic potential in melanoma cells (Bandari et al. (2003) *Regul. Peptide* 111:169). Recently, a longer form of a murine-related gene, osteoactivin, showed bone invasion and confers an aggressive form of tumor in mice (Weterman, et al. (1995) *Int. J. Cancer* 60:73-81). Osteoactivin is expressed in several cancers, breast cancer included (Rich et al. (2003) *J. Biol. Chem.* 278:15951). The studies of the present inventors have reported that HGFIN is expressed in differentiated hematopoietic cells (Brekken & Sage (2001) *Matrix Biol.* 19:816). Analysis of the human and murine genome sequence databases indicate that HGFIN is only in humans as a truncated form of osteoactivin. Ongoing studies cloned the HGFIN promoter, which showed eight consensus sequences for p53. The present studies indicate that HGFIN may have properties consistent with tumor suppression.

The HGFIN gene is on chromosome 7, flanked by microsatellites indicating that this gene could become unstable. Cancer stem cells, which prefer the bone marrow as their site of metastasis, have long doubling time and are resistant to chemotherapy. It appears that HGFIN could be one of the first "hits" of the cancer cells. This means that the cancer cells disrupt the production and/or activity of HGFIN as one of its first progressive actions. Subsequent "hits" result in the formation of cancer progenitors that are susceptible to chemotherapy and other targeting agents.

The research of the present invention also indicates that HGFIN is a decoy receptor for Substance P, which is the high affinity receptor for NK-1.

Contemplated by the present invention is a method for inhibiting the growth of a cancer cell wherein cancer cells are contacted with an effective amount of HGFIN which results in inhibition of the growth of the cancer cell. The present invention, thus, also includes methods for treating cancer that are based on administering to a patient an effective dose of HGFIN. Experiments have been performed in a mouse model of tumor growth showing in vivo activity of HGFIN to affect tumor cell growth, and thus identifying HGFIN as a molecular target for cancer therapy. These in vivo data extend the findings in vitro and provide direct evidence that HGFIN is active in vivo as a tumor suppressor gene in cancer cells. Moreover, these data provide in vivo evidence that contacting a cancer cell with an effective amount of HGFIN inhibits cancer cell growth. Based on these data it is clear that HGFIN activity in vitro correlates with its activity in vivo as a tumor suppressor agent.

In the context of the present invention, "an effective amount" or "an effective dose" of HGFIN is any amount of HGFIN that has the ability to inhibit tumor cell growth or reduce the volume of a tumor as compared to no treatment. Also in the context of the present invention, a "pharmaceutically acceptable carrier" is any substance that is mixed with HGFIN in order to allow it to be administered to an animal, including humans. Thus, one of skill in the art would chose a carrier based on their experience since such carriers are well-known in the art. A generally recognized compendium of such methods and ingredients is Remington: The Science and Practice of Pharmacy, Alfonso R. Gennaro, editor, 20th ed. Lippincott Williams & Wilkins: Philadelphia, Pa., 2000. All carriers must be acceptable in the sense of being compatible with the other ingredients of the formulation and not injurious to the patient. Examples of materials which can serve as pharmaceutically acceptable carriers include but are not limited to saline, phosphate-buffered saline, sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminium hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in formulations.

According to one aspect of this invention, an isolated polynucleotide encoding a novel white blood cell regulating protein is provided. Preferably, the polynucleotide comprises the sequence: SEQ ID NO:1; an allelic variant of SEQ ID NO:1; a sequence hybridizing with SEQ ID NO:1 or its complement under moderate hybridization and washing conditions; an antisense sequence to SEQ ID NO:1; a sequence encoding a polypeptide having an amino acid sequence of SEQ ID NO:2 with up to 30% conservative substitutions; SEQ ID NO:2; an allelic variant of SEQ ID NO:2 and a sequence hybridizing with SEQ ID NO:2 or its complement under moderate hybridization and washing conditions.

Another aspect of the invention features a recombinant DNA or RNA molecule comprising a vector having an insert that includes part or all of an HGFIN, or its antisense, polynucleotide and cells transformed with the recombinant DNA molecule. Preferably, the cells are murine, human, bovine, canine, feline or rat cells. Most preferably, the cells are bone marrow derived cells, such as stem cells, progenitor cells, white and/or red blood cells, including B-cells, T-cells, granulocytes, monocytes, macrophages, neutrophils, and the like, of the aforementioned organisms.

The invention also features an isolated polypeptide produced by expression of the HGFIN polynucleotides described above. Antibodies immunologically specific for the protein, or one or more epitopes thereof, are also provided. Pharmaceutical compositions containing the HGFIN polynucleotide, antisense sequence, protein, protein fragments and/or antibodies immunospecific to the protein, are also provided.

The present invention may be implicated in diseases and conditions such as leukemia, lymphoma, and breast cancer. Hence, the invention relates to compositions and methods for treating diseases associated with increased cell proliferation, by administering a HGFIN gene or protein to increase differentiation. Conversely, the invention may be used to treat a disease associated with decreased cell proliferation by administering an HGFIN antisense sequence, thereby downregulating the expression of the HGFIN protein or antibody, to competitively inhibit the SP modulator, or any other natural or synthetic ligand. for HGFIN, from binding to the HGFIN receptor and inducing cell differentiation.

In a more specific embodiment, the invention relates to methods for using such polynucleotides, polypeptides and antibodies for preventing or treating acute and chronic myeloid leukemia and acute and chronic lymphocytic leukemia, as well as the B-cell subtype of Hodgkin's and non-Hodgkin's lymphomas. More specifically, for example, the compositions of the present invention may be used for the treatment of Acute Myelocytic Leukemia, which is associated with the accumulation of immature blast cells, wherein the administration of HGFIN compositions may enhance the maturation of the affected cells thus alleviating the leukemic condition and the anemia and low platelet blood count associated with this disease. Further, the compositions of the present invention may also be useful in the treatment of Acute Lymphocytic Leukemia which is associated with increased proliferation of immature lymphocytes, wherein the administration of an HGFIN composition may inhibit and/or slow down proliferation and promote differentiation, helping the cells mature before becoming the cells of the peripheral blood system.

The compositions of the present invention may also be useful in the treatment of Chronic Myelogenous Leukemia which is marked by the abnormal proliferation of immature granulocytes in the bone marrow and blood, wherein the administration of an HGFIN composition that includes an HGFIN antisense sequence or HGFIN immunospecific antibody may inhibit and or slow down proliferation, allowing the developing cells time to mature before differentiating into the cells of the peripheral blood system. Further, the compositions of the present invention may also be useful in the treatment of Chronic Lymphocytic Leukemia which is marked by mature but poorly functioning lymphocytes circulating in the blood, wherein the administration of an HGFIN composition may inhibit and or slow down the earlier stages of proliferation, allowing more time for the cells to mature before terminal differentiation.

In the same way, the compositions and methods of the present invention can be used in the treatment of both Hodgkin's and non-Hodgkin's type Lymphoma, which can be marked both by lymphocytic-rich and lymphocytic-depleted blood levels.

In another embodiment HGFIN immunospecific antibodies may be used to target disease cells, these antibodies may also be conjugated with chemo- or radio-toxic agents to kill off leukemia or lymphoma associated cells. Such a method would also allow for the reduction of side effects caused by the administration of such, cyto- or radio-toxic elements by reducing the amount of dosage of the toxic agent needed to kill affected cells.

In yet another aspect of the present invention, HGFIN is administered to a patient with a hyperproliferative disease. Preferably, HGFIN is administered in a pharmaceutically effective does and the administration is repeated to maintain a therapeutically effective dosage in the blood and/or site of the hyperproliferation within the body. The dosage may be between 0.01 µg and 500 mg/administration, but is preferably between 30 µg and 50 mg/administration, and more preferably between 100 µg and 1 mg/administration. The administration may be oral, intravenous, parenteral, nasal, or transdermal. Preferably, the HGFIN is administered into the circulatory system or respiratory system. The route of administration will be selected based upon whether the site of hyperproliferation is occurring at one or a few selected locations, such as with a localized tumor, or is a systemic problem throughout the patient. The dosage will be based upon the route of administration, body weight of the patient, health of the patient at the time of administration and other factors, all of which are routinely considered by an ordinarily skilled clinician.

HGFIN may be used to treat hyperproliferative diseases either in the protein or nucleic acid form. If it is used in the nucleic acid form, it is preferably administered in one of the vectors described herein. Preferably, the HGFIN nucleotide sequence used to treat hyperproliferative disorders is at least 80% homologous to SEQ ID NO:1, more preferably at least 95% homologous to SEQ ID NO:1, even more preferably is at least 98% homologous to SEQ ID NO:1, and most preferably is SEQ ID NO:1. If a protein sequence of HGFIN is administered, preferably, it is at least 80% homologous to SEQ ID NO:2, more preferably at least 95% homologous to SEQ ID NO:2, even more preferably is at least 98% homologous to SEQ ID NO:2, and most preferably is SEQ ID NO:2. When the HGFIN protein is administered, it is preferably in a pharmaceutically acceptable carrier.

The hyperproliferative disorder may be any hyperproliferative disorder such as cancer, blood vessel proliferative disorder, fibrotic disorder, or rejection of transplanted material. Preferably, the disorder to be treated is cancer. Cancer is a general term for more than one hundred diseases, which are characterized by uncontrollable, abnormal growth of cells. Most preferably, the disorder to be treated is breast cancer.

Treatment of the hyperproliferative disorder may occur in combination with another therapy for treating the disorder. In the context of the present invention a "therapy" is any one of a number of treatments or agents and would include but not be limited to radiation therapy, chemotherapy, ablative surgery, or partially ablative surgery, all of which are also aimed at treating the hyperproliferative disease or disorder, such as cancer. HGFIN may also be administered in combination with methods aimed at modulating and typically down-regulating NK-1 and/or NK-2. SP, for which HGFIN is a probable decoy receptor, may also be modulated to increase the activity and/or expression of HGFIN in a patient so that HGFIN can exert its hyperproliferative-suppressing activity. PPT-1 activity and/or expression can also be regulated in conjunction with the methods described herein so that HGFIN activity and/or expression can be sufficient to suppress hyperproliferative activity, such as tumor formation and cancer cell growth. Finally, HGFIN agonists may be administered to a patient, either with the HGFIN administration, or separately, to increase the effectiveness of HGFIN. Regulation of all of the above substances may be achieved through direct administration of the product, stimulation of endogenous production, the addition of enhancers, promoters, agonists, antagonists, and/or other methods known in the art for upregulating or down-regulating a given substance.

HGFIN antagonists, such as an HGFIN antibody, may be used to treat hypoproliferative disorders, such as hypoproliferative anemia. In this case, the HGFIN antibody would be administered in a pharmaceutically effective amount and in a suitable carrier as that the affected cells would be encouraged to grow. HGFIN antagonists could also be used in conjunction with the HGFIN administration techniques described herein as a method of controlling for an overabundance of HGFIN and/or to keep a precise balance of HGFIN activity in a patient within the prescribed limits.

As indicated, Applicants have identified Hemtaopoietic Growth Factor Inducible Neurokinin-I type (HGFIN) as a gene that is differentially regulated between differentiated peripheral hematopoietic cells and immature, unstimulated mesenchymal stromal cells. Applicants have performed differential cloning between mature, differentiated leukocytes and immature, unstimulated stromal cells and have identified the HGFIN gene by DNA sequence analysis. Based on an understanding of the leukemia and lymphoma related diseases, in which uncontrolled proliferation of immature progenitor cells without differentiation is indicative of the diseased state, the genes and/or proteins of the present invention appear to play a role in mediating the initiation and progression of B-cell related blood diseases, specifically, the various related leukemias and lymphomas.

From the methods, herein described, it has been determined that based on the fact that HGFIN expression was down-regulated in differentiated cells that were stimulated with the mitogen LPS, HGFIN could be an inhibitor of cell activation. Further, in mesenchymal bone marrow cells, HGFIN was induced by both cytokines and a neurotrophic factor. Since, the bone marrow mesenchymal cells support hematopoiesis and are involved in bone remodeling, these data indicate that HGFIN is likely involved in bone marrow functions throughout the hematopoietic hierarchy.

To understand the difference in NK-1 function in the bone marrow, three different cDNA libraries were screened with an NK-1-specific probe (Gerard et al. (1991) *Biochemistry* 30:10640-10646). Seven clones were selected after the cDNA libraries were screened with a cDNA probe specific for the human NK-1 (Gerard et al. (1991) supra). After sequencing the DNA inserts in the forward and reverse orientations, search of the DNA database indicated that Clone 7 was homologous to the mnb cDNA (Weterman, et al. (1995) supra) and that the coding region spanned +60/+1742 of SEQ ID NO:1

Since the mesenchymal/stromal cells were the major NK-1-expressing cell subsets (Rameshwar (1997) supra), two of the cDNA libraries were prepared with cytokine-stimulated bone marrow stroma. A cDNA library from unstimulated bone marrow mononuclear cells was also screened for the purpose of identifying NK-1 subtypes in baseline/unstimulated cells. One of the retrieved clones was sequenced and its expression in various tissues was studied. HGFIN expression was different at the various cellular levels that comprise the hematopoietic hierarchy. At the lower spectrum, HGFIN mRNA was detected in differentiated hematopoietic cells and in peripheral immune cells, which are predominantly differentiated cells.

In contrast, HGFIN mRNA was undetectable in unstimulated, mesenchymal stromal cells unless they were stimulated. The stromal cells are involved in the hematopoietic spectrum at all levels, in particular at the stem cell and osteoclast development (Muller-Sieburg & Deryugina (1995) *Stem Cells* 13:477-486; Randall & Weissman (1998) *Stem Cells* 16:38-48; Roodman (1999) *Exp. Hematol.* 27:1229-1241) levels. Thus, the expression of HGFIN in the stromal cells leads to the conclusion that the HGFIN gene is involved in the support of hematopoiesis at various stages, and might also be involved in bone remodeling (Randall & Weissman (1998) supra; Roodman (1999) supra). Further evidence for HGFIN as a mediator of cell differentiation was shown when its expression coincided with the down-regulation of Id2, the transcription factor that is a dominant negative regulator of cell differentiation (Biggs, et al. (1992) *Proc. Natl. Acad. Sci. USA* 89:1512-1516). Other functions of HGFIN were suggested by its down-regulation in immune cells following cell activation. Computational analyses provided insights into the properties of HGFIN protein. For further details, see the examples detailed herein.

The present disclosure further shows that there are two major subsets of breast cancer cells: stem cells and progenitors. Both types of cancer cells leave the mammary gland long before the tumor is clinically detectable, but the difference from transplantation is that the process of entry is facilitated by the underlying mesenchymal stem cells. The exiting cancer cells could enter different tissues through the circulation by the process of 'seeding', rather than 'homing'. Cancer stem cells and progenitors enter the bone cavity similar to the homing strategies of bone marrow hematopoietic stem cells (HSC) in transplantation (Little & Storb (2002) *Nature Rev.* 2:231). A HSC can form cell lineages to generate all types of immune and blood cells (Zon (1995) *Blood* 86:2876; Akashi et al. (2000) *Nature* 404:193). It is at a site close to the endosteal region that the cancer stem cells are found, which become part of the stromal compartment to regulate functions of HSC.

Once in the marrow, both the cancer progenitors and stem cells integrate among the stroma but only the stem cells survive in the long-term where the cells find a niche. At the early stages, the cancer stem cells will not interfere with the normal hematopoietic activity of the bone marrow. This seemingly normal function of the cancer stem cells in the bone marrow is due, in part, to the long-doubling time of the cancer stem cells and their transient transition from epithelial to fibroblastoid/stromal-type cells while retaining cytokeratin marker. The cancer stem cells can become an aggressive tumor through the formation of rapidly dividing cancer progenitors. The cancer stem cells protect themselves by self-renewal, which is analogous to hematopoietic stem cells (Punzel et al. (2002) *Exp. Hematol.* 30:464; Spits et al. (1998) *Immunol. Rev.* 165:75; King et al. (2001) *Proc. Natl. Acad. Sci. USA* 99:4508). PPT-1 and HGFN are central to the entry and formation of a niche of the breast cancer cells. These two genes are closely linked to other molecules and are important to the early events of breast cancer metastasis to bone marrow.

Mesenchymal Stem Cells (MSCs) are intriguing cells with respect to immunological properties. They surround the vasculature in the bone marrow. The present experiments show that a facilitating function of MSC is for exit of breast cancer cells through endothelial barrier to the periphery. These cells express MHC Class II and can elicit allogeneic responses. However, in an experimentally graft vs. host model, MSC show veto properties (Randall & Weissman (1998) supra). The present invention and related research shows that MSC express various categories of cytokines, chemokines and other molecules that are amendable to cancer metastasis (Bianco et al. (2001) *Stem Cells* 19:180).

This present disclosure studies show that suppression of PPT-1 expression in breast cancer cell lines and primary breast cancer cells (by siRNA strategies) correlate with the loss of breast cancer cells to integrate and become part of the stromal compartment of the bone marrow. Furthermore, overexpression of PPT-1 in normal mammary epithelial cells leads to colony formation in methylcellulose matrix. Non-transformed mammary epithelial cells cannot integrate as bone marrow stroma unless the PPT-1 gene is overexpressed and PPT-1 overexpressing cells show radioresistance. In summary, published and preliminary studies show a non-mutational oncogenic property for the PPT-1 gene that allows cells expressing this gene to integrate among stromal cells, in the absence of exogenous growth factors.

Although specific embodiments of the present invention will now be described, it should be understood that such embodiments are by way of example only and merely illustrative of but a small number of the many possible specific embodiments that can represent applications of the principles of the present invention. Various changes and modifications obvious to one skilled in the art to which the present invention pertains are deemed to be within the spirit, scope and contemplation of the present invention as further defined in the appended claims.

Various terms relating to the biological molecules of the present invention are used throughout the specification and claims.

"HGFIN" refers generally to an HGFIN polypeptide that is highly inducible by NK-1 stimulation in differentiated hematopoietic cells and also in peripheral immune cells, as well as having expression that coincides with the down regulation of Id2, in accordance with the present invention, which is described in detail herein above and throughout the specification.

"HGFIN activity or HGFIN polypeptide activity" or "biological activity of the HGFIN or HGFIN polypeptide" refers to the metabolic or physiologic function of said HGFIN including similar activities or improved activities or these activities with decreased undesirable side effects. Also included are antigenic and immunogenic activities of said HGFIN. In particular, HGFIN encodes a protein receptor that has homology at its C-terminal to PKD and may bind to SP.

"HGFIN gene" refers to a polynucleotide as defined above in accordance with the present invention, which encodes an HGFIN polypeptide.

An "HGFIN therapeutic" refers to a therapeutically effective amount of an HGFIN related genetic sequence such as, but not limited to polynucleotide, polynucleotide antisense sequence, and HGFIN peptide, protein or protein fragment as well as an HGFIN antibody or antibody fragment.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated," as the term is employed herein.

"Polynucleotide" generally refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA.

The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the gene-encoded amino acids. "Polypeptides" include amino acid sequences modified either by natural processes, such as posttranslational processing, or by chemical modification techniques that are well known in the art. Such modifications are well described in basic texts and in more detailed monographs, as well as in voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from post-translation natural processes or may be made by synthetic methods.

Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racernization, selenoylation, sulfation, transfer-RNA mediated addition of amino acids to proteins such as arginylation, and ubiquitination. See, for instance, Proteins—Structure and Molecular Properties, $2^{nd}$ Ed., T. E. Creighton, W. H. Freeman and Company, New York, 1993 and Wold, F., "Posttranslational Protein Modifications: Perspectives and Prospects, pgs. 1-12 in "Posttranslational Covalent Modification Of Proteins", B, C. Johnson, Ed., Academic Press, New York, 1983; Seifter et al. (1990) *Meth Enzymol* 182:626-646 and Rattan et al. (1992) *Ann NY Acad Sci* 663:48-62.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical.

A variant and reference polypeptide may differ in amino acid sequence by one or more substitutions, additions, and deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis. For instance, a conservative amino acid substitution may be made with respect to the amino acid sequence encoding the polypeptide. A "conservative amino acid substitution", as used herein, is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The term "substantially the same" refers to nucleic acid or amino acid sequences having sequence variation that do not materially affect the nature of the protein (i.e. the structure, stability characteristics, substrate specificity and/or biological activity of the protein). With particular reference to nucleic acid sequences, the term "substantially the same" is intended to refer to the coding region and to conserved sequences governing expression, and refers primarily to degenerate codons encoding the same amino acid, or alternate codons encoding conservative substitute amino acids in the encoded polypeptide. With reference to amino acid sequences, the term "substantially the same" refers generally to conservative substitutions and/or variations in regions of the polypeptide not involved in determination of structure or function.

The terms "percent identical" and "percent similar" are also used herein in comparisons among amino acid and nucleic acid sequences. When referring to amino acid sequences, "identity" or "percent identical" refers to the percent of the amino acids of the subject amino acid sequence that have been matched to identical amino acids in the compared amino acid sequence by a sequence analysis program. "Percent similar" refers to the percent of the amino acids of the subject amino acid sequence that have been matched to identical or conserved amino acids. Conserved amino acids are those which differ in structure but are similar in physical properties such that the exchange of one for another would not appreciably change the tertiary structure of the resulting protein. Conservative substitutions are defined in Taylor ((1986) *J. Theor. Biol.* 9:205). When referring to nucleic acid—molecules, "percent identical" refers to the percent of the nucleotides of the subject nucleic acid sequence that have been matched to identical nucleotides by a sequence analysis program "Identity" and "similarity" can be readily calculated by known methods. Nucleic acid sequences and amino acid sequences can be compared using computer programs that align the similar sequences of the nucleic or amino acids thus define the differences. In preferred methodologies, the BLAST programs (NCBI) and parameters used therein are employed, and the DNAstar system (Madison, Wis.) is used to align sequence fragments of genomic DNA sequences. However, equivalent alignments and similarity/identity assessments can be obtained through the use of any standard alignment software. For instance, the GCG Wisconsin Package version 9.1, available from the Genetics Computer Group in Madison, Wis., and the default parameters used (gap creation penalty=12, gap extension penalty=4) by that program may also be used to compare sequence identity and similarity.

With respect to single-stranded nucleic acid molecules, the term "specifically hybridizing" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule, to the substantial exclusion of hybridization of the oligonucleotide with single-stranded nucleic acids of non-complementary sequence.

With respect to oligonucleotide constructs, but not limited thereto, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide construct with a substantially complementary sequence contained within a single-stranded DNA or RNA molecule of the invention, to the substantial exclusion of hybridization of the oligonucleotide with single-stranded nucleic acids of non-complementary sequence.

The term "substantially pure" refers to a "preparation comprising at least 50-60% by weight the compound of interest (e.g., nucleic acid, oligonucleotide, protein, etc.). More preferably, the preparation comprises at least 75% by weight, and most preferably 90-99% by weight, the compound of interest. Purity is measured by methods appropriate to the compound of interest (e.g. chromatographic methods, agarose or polyacrylamide gel electrophoresis, HPLC analysis, and the like).

The term "expression cassette" refers to a nucleotide sequence that contains at least one coding sequence along with sequence elements that direct the initiation and termination of transcription. An expression cassette may include additional sequences, including, but not limited to promoters, enhancers, and sequences involved in post-transcriptional or post-translational processes.

A "coding sequence" or "coding region" refers to a nucleic acid molecule having sequence information necessary to produce a gene product, when the sequence is expressed.

The term "operably linked" or "operably inserted" means that the regulatory sequences necessary for expression of the coding sequence are placed in a nucleic acid molecule in the appropriate positions relative to the coding sequence so as to enable expression of the coding sequence. This same definition is sometimes applied to the arrangement other transcription control elements (e.g., enhancers) in an expression vector.

Transcriptional and translational control sequences are DNA regulatory sequences, such as promoters, enhancers, polyadenylation signals, terminators, and the like, that provide for the expression of a coding sequence in a host cell.

The terms "promoter," "promoter region" or "promoter sequence" refer generally to transcriptional regulatory regions of a gene, which may be found at the 5' or 3' side of the coding region, or within the coding region, or within introns. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase.

A "vector" is a replicon, such as plasmid, phage, cosmid, or virus to which another nucleic acid segment may be operably inserted so as to bring about the replication or expression of the segment.

The term "nucleic acid construct" or "DNA construct" is sometimes used to refer to a coding sequence or sequences operably linked to appropriate regulatory sequences and inserted into a vector for transforming a cell. This term may be used interchangeably with the term "transforming DNA". Such a nucleic acid construct may contain a coding sequence for a gene product of interest, along with a selectable marker gene and/or a reporter gene.

The term "selectable marker gene" refers to a gene encoding a product that, when expressed, confers a selectable phenotype such as antibiotic resistance on a transformed cell.

The term "reporter gene" refers to a gene that encodes a product that is detectable by standard methods, either directly or indirectly.

A "heterologous" region of a nucleic acid construct is an identifiable segment (or segments) of the nucleic acid molecule within a larger molecule that is not found in association with the larger molecule in nature. Thus, when the heterologous region encodes a mammalian gene, the gene will usually be flanked by DNA that does not flank the mammalian genomic DNA in the genome of the source organism. In another example, a heterologous region is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

The term "DNA construct", as defined above, is also used to refer to a heterologous region, particularly one constructed for use in transformation of a cell. A cell has been "transformed" or "transfected" or "transduced" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA.

The term "in vivo delivery" involves the use of any gene delivery system, such as viral- and liposome-mediated transformation for the delivery and introduction of a therapeutic agent to the cells of a subject while they remain in the subject. Such therapeutic agents may include, for example, HGFIN DNA, HGFIN cDNA, HGFIN RNA, and HGFIN antisense polynucleotide sequences.

As used herein, the term "transduction," is used to describe the delivery of DNA to eukaryotic cells using viral mediated delivery systems, such as, adenoviral, AAV, retroviral, or plasmid delivery gene transfer methods. Preferably the viral mediated delivery system is targeted specifically to the cell, wherein delivery is sought. The production of targeted delivery systems is well known and practiced in the recombinant arts. A number of methods for delivering therapeutic formulations, including DNA expression constructs (as described further below), into eukaryotic cells are known to those skilled in the art. In light of the present disclosure, the skilled artisan will be able to deliver the therapeutic agents of the present invention to cells in many different but effective ways. For instance, the specificity of viral gene delivery may be selected to preferentially direct the HGFIN gene to a particular target cell, such as by using viruses that are able to infect particular cell types (i.e., leukemia cells). Naturally, different viral host ranges will dictate the virus chosen for gene transfer.

In vitro gene delivery" refers to a variety of methods for introducing exogenous DNA into a cell that has been removed from its host environment.

As used herein the term "transfection" is used to describe the delivery and introduction of a therapeutic agent to a cell using non-viral mediated means, these methods include, e.g., calcium phosphate- or dextran sulfate-mediated transfection; electroporation; glass projectile targeting; and the like. These methods are known to those of skill in the art, with the exact compositions and execution being apparent in light of the present disclosure.

"Ex vivo gene delivery" refers to the procedure wherein appropriate cells are removed form the host organism, transformed, transduced or transfected in accordance with the teachings of the present invention, and replaced back into the host organism, for the purpose of therapeutic restoration and/or prevention.

"Delivery of a therapeutic agent" may be carried out through a variety of means, such as by using parenteral delivery methods such as intravenous and subcutaneous injection, and the like. Such methods are known to those of skill in the art of drug delivery, and are further described herein in the sections regarding pharmaceutical preparations and treatment. Compositions include pharmaceutical formulations comprising a HGFIN gene, protein, or antisense polynucleotide sequence that may be delivered in combination with a radio or chemotoxic agent, such as cisplatin. In such compositions, the HGFIN may be in the form a DNA segment, recombinant vector or recombinant virus that is capable of expressing a HGFIN protein in a cell, specifically, in a bone marrow cell. These compositions, including those comprising a recombinant viral gene delivery system, such as an adenovirus particle, may be formulated for in vivo administration by dispersion in a pharmacologically acceptable solution or buffer. Preferred pharmacologically acceptable solutions include neutral saline solutions buffered with phosphate, lactate, Tris, and the like.

A "clone" is a population of cells derived from a single cell or common ancestor by mitosis.

A "cell line" is a clone of a primary cell that is capable of stable growth in vitro for many generations.

The term "contacted" when applied to a cell is used herein to describe the process by which an HGFIN gene, protein or antisense sequence, and/or an accessory element (such as an antibody or cytotoxic agent), is delivered to a target cell or is placed in direct proximity with the target cell. This delivery may be in vitro or in vivo and may involve the use of a recombinant vector system. Any method may be used to contact a cell with the HGFIN associated protein or nucleotide sequence, so long as the method results in either increased or decreased levels of functional HGFIN protein within the cell. This includes both the direct delivery of an HGFIN protein to the cell and the delivery of a gene or DNA segment that encodes HGFIN, or its antisense polynucleotide sequence, which gene or antisense sequence will direct or inhibit, respectively, the expression and production of HGFIN within the cell. Since protein delivery is subject to drawbacks, such as degradation and low cellular uptake, it is contemplated that the use of a recombinant vector that expresses a HGFIN protein, or encodes for an HGFIN polynucleotide antisense sequence, will be of particular advantage for delivery.

The term "mammal" refers to such organisms as mice, rats, rabbits, goats, horse, sheep, cattle, cats, dogs, pigs, more preferably monkeys and apes, and most preferably humans.

"Antibodies" as used herein include polyclonal and monoclonal antibodies, chimeric, single chain, and humanized antibodies, as well as Fab fragments, including the products of a Fab or other immunoglobulin expression library. With respect to antibodies, the term, "immunologically specific" refers to antibodies that bind to one or more epitopes of a protein of interest, but which do not substantially recognize and bind other molecules in a sample containing a mixed population of antigenic biological molecules.

The term "specific binding affinity" is meant that the antibody or antibody fragment binds to target compounds with greater affinity than it binds to other compounds under specified conditions. Antibodies or antibody fragments having specific binding affinity to a compound may be used in methods for detecting the presence and/or amount of the compound in a sample by contacting the sample with the antibody or antibody fragment under conditions such that an immunocomplex forms and detects the presence and/or amount of the compound conjugated to the antibody or antibody fragment.

The term "polyclonal" refers to antibodies that are heterogeneous populations of antibody molecules derived from the sera of animals immunized with an antigen or an antigenic functional derivative thereof. For the production of polyclonal antibodies, various host animals may be immunized by injection with the antigen. Various adjuvants may be used to increase the immunological response, depending on the host species.

"Monoclonal antibodies" are substantially homogenous populations of antibodies to a particular antigen. They may be obtained by any technique that provides for the production of antibody molecules by continuous cell lines in culture. Monoclonal antibodies may be obtained by methods known to those skilled in the art. See, for example, Kohler, et al. (1975) *Nature* 256:495-497, and U.S. Pat. No. 4,376,110.

The term "antibody fragment" refers to a portion of an antibody, often the hypervariable region and portions of the surrounding heavy and light chains, that displays specific binding affinity for a particular molecule. A hypervariable region is a portion of an antibody that physically binds to the target compound. The term "antibody fragment" also includes single charge antibodies.

With respect to "therapeutically effective amount" is an amount of the polynucleotide, antisense polynucleotide or protein of HGFIN, or immunospecific antibody, or fragment thereof, that when administered to a subject is effective to bring about a desired effect (e.g., an increase or decrease in cell maturation, differentiation and/or proliferation, tumor suppression, or target cell activation) within the subject.

With respect to "radiotherapy agents" or "chemotherapy agents," these terms are defined herein as any chemical compound or treatment method that induces cell damage and/or results in death of a cell, when applied. Such agents and factors include adriamycin, 5-fluorouracil (5FU), etopside (VP-116), camptothecin, actinomycin-D, mitomycin C, cisplatin (CDDP), and even hydrogen peroxide. Other factors include radiation and waves, such as .gamma.-irradiation, X-rays, UV-irradiation, microwaves, electro-emissions, and the like. The invention also encompasses the use of a combination of one or more of these agents used in concert, whether radiation-based or actual compounds, such as the use of X-rays with cisplatin.

The present invention provides a novel gene, HGFIN, which appears to act as a mediator of pluripotent stem or progenitor cell differentiation and other interrelated physiological processes of hematopoieses. The HGFIN gene and protein of the present invention share a portion of sequence homology to the polycistic kidney disease (PKD) portion of the NK-1 receptor. Hence, like NK-1, the coded for HGFIN protein binds Substance P (SP) and thus plays a role in the stimulation of hematopoiesis and/or, as determined from the methods described herein, HGFIN may be instrumental in the regulation of leukocyte proliferation and differentiation, including the inducement of differentiation and inhibition of proliferation. In addition, since HGFIN can bind SP, treatments for cancer may involve targeting NK receptors in combination with HGFIN. This treatment method may be particularly effective for the treatment of breast cancer. The summary of the invention described above is non-limiting and other features and advantages of the invention will be apparent from the following detailed description.

The present invention concerns compositions and methods for treating various lymphoproliferative-related diseases associated with either an unhealthy increase or decrease in leukocyte proliferation and/or differentiation. The invention is based firstly on the discovery that HGFIN mRNA was detected in differentiated hematopoietic and peripheral immune cells but not in unstimulated mesenchymal stromal cells, and secondly on the proteomic analyses that show that SP binds to the PKD portion of the HGFIN protein receptor. Thus, the present inventors discovered that HGFIN plays a role in hematopoietic cell maturation and may be useful in the treatment of the various forms of leukemia, lymphoma and other maladies related to stem and/or progenitor cell proliferation or differentiation.

As stated, this invention is based in part on the discovery that HGFIN mRNA was detected in differentiated hematopoietic cells and in peripheral immune cells, which are predominantly differentiated cells. In contrast, HGFIN mRNA was undetectable in unstimulated, mesenchymal stromal cells unless they were stimulated. Since, the stromal cells regulate the hematopoietic spectrum at all levels, in particular with regard to stem cell and osteoclast development (Muller-Sieburg & Deryugina (1995) supra; Randall & Weissman (1998) supra; Roodman (1999) supra), the expression of HGFIN in the stromal cells suggests that the HGFIN gene plays a role in the support of hematopoiesis at various stages, and is likely to be involved in bone remodeling (Randall & Weissman (1998) supra; Roodman (1999) supra). Further evidence for HGFIN as a mediator of cell differentiation was shown when its expression coincided with the down regulation of Id2, the transcription factor that is a dominant negative regulator of cell differentiation (Biggs, et al. (1992) supra). Other functions of HGFIN were suggested by its down regulation in immune cells following cell activation.

As described in detail herein, the HGFIN gene was first identified and cloned from human bone marrow stroma cells. The human HGFIN gene is set out in SEQ ID NO:1. The nucleic acid sequence of the HGFIN cDNA was translated in six reading frames. Computer analysis of the protein sequence, using PredictProtein software, showed that the longest and most probable protein consisted of 560 residues. A BLAST search indicated homology to the mub precursor protein (SwissProt Q14956). This 560 amino acid protein was aligned to the sequence of the NK-1 receptor. PredictProtein results were used to determine the characteristics of the HGFIN protein. Among the databases used by PredictProtein were ProSite, ProDom, Predator, Globe and PHD (Corpet, et al. (1998) *Nucleic Acid Res.* 26:323-326; Bairoch, et al. (1997) *Nucleic Acid Res.* 25:217-221; Rost & Sander (1993) *J. Mol. Biol.* 232:584-599; Rost & Sander (1994) *Proteins* 19:55-72; Sonnhammer, et al. (1998) In *Proceedings of 6th International Conference on Intelligent Systems for Molecular Biology.* Glasgow, et al. (ed.) Menlo Park, Calif. p. 175-182). GeneMine's Look 3.5 (Molecular Ass. Group) was used to construct a 3-D model of a region of the HGFIN protein. TRIPOS SYBYL was used to minimize the 3-D structure and also examine the possible interaction with SP.

The HGFIN polynucleotides of the present invention include isolated polynucleotides encoding the HGFIN polypeptides and fragments, and polynucleotides closely related thereto. More specifically, HGFIN polynucleotides of the invention include a polynucleotide comprising the human nucleotide sequences contained in SEQ ID NO:1 encoding an HGFIN polypeptide of SEQ ID NO:2, and polynucleotides having the particular sequence of SEQ ID NO:1.

HGFIN polynucleotides further include a polynucleotide comprising a nucleotide sequence that has at least 70% identity over its entire length to a nucleotide sequence encoding the HGFIN polypeptide of SEQ ID NO:2, and a polynucleotide comprising a nucleotide sequence that is at least 70% identical to that of SEQ ID NO:1, over its entire length. In this regard, polynucleotides with at least 70% are preferred, more preferably at least 80% even more preferably at least 90% identity, yet more preferably at least 95% identity, 97% are highly preferred and those with at least 98-99% are most highly preferred, with at least 99% being the most preferred. Also included under HGFIN polynucleotides are a nucleotide sequence which has sufficient identity to a nucleotide sequence contained in SEQ ID NO:1 to hybridize under conditions useable for amplification or for use as a probe or marker. The invention also provides polynucleotides that are complementary to such HGFIN polynucleotides.

Also included in the present invention are polynucleotides encoding polypeptides which have at. least 70% identity, preferably at least 80% identity, more preferably at least 90% identity, yet more preferably at least 95% identity, even more preferably at least 97-99% identity, to the amino acid sequence of SEQ ID NO:2, over the entire length of the recited amino acid sequences.

The nucleotide sequences encoding the HGFIN polypeptide of SEQ ID NO:2 may be identical to the polypeptide encoding sequence contained in SEQ ID NO:1, or it may be a sequence, which as a result of the redundancy (degeneracy) of the genetic code, also encodes the polypeptide of SEQ ID NO:2.

When the polynucleotides of the invention are used for the recombinant production of the HGFIN polypeptide, the polynucleotide may include the coding sequence for the mature polypeptide or a fragment thereof, by itself; the coding sequence for the mature polypeptide or fragment in reading frame with other coding sequences, such as those encoding a leader or secretory sequence, a pre-, or pro- or prepro-protein sequence, or other fusion peptide portions. For example, a marker sequence which facilitates purification of the fused polypeptide can be encoded. The polynucleotide may also contain non-coding 5' and 3' sequences, such as transcribed, non-translated sequences, splicing and polyadenylation signals, ribosome binding sites and sequences that stabilize mRNA.

Thus, this invention provides oligonucleotides (sense or antisense strands of DNA, cDNA or RNA) having sequences capable of hybridizing with at least one sequence of a nucleic acid molecule encoding the protein of the present invention. Such oligonucleotides are useful as probes for detecting HGFIN genes or transcripts and may also be useful in the treatment of various blood cell related diseases, when delivered by an appropriate vehicle to the affected cells. In one preferred embodiment, oligonucleotides for use as probes or primers are based on, rationally-selected amino acid sequences chosen from SEQ ID NO:1. In preferred embodiments, the amino acid sequence information is used to make degenerate oligonucleotide sequences as is commonly done by those skilled in the art which can be used to screen cDNA libraries from human, mouse, bovine, canine, feline and rat.

HGFIN polynucleotides of the present invention may be prepared by two general methods: (1) they may be synthesized from appropriate nucleotide triphosphates, or (2) they may be isolated from biological sources. Both methods utilize protocols well-known in the art. The availability of nucleotide sequence information, such as the cDNA having SEQ ID NO:1, enables preparation of an isolated nucleic acid molecule of the invention by oligonucleotide synthesis.

Synthetic oligonucleotides may be prepared by the phosphoramadite method employed in the Applied Biosystems 38A DNA Synthesizer or similar devices. The resultant construct may be purified according to methods known in the art, such as high performance liquid chromatography (HPLC). Long, double-stranded polynucleotides, must be synthesized in stages, due to the size limitations inherent in current oligonucleotide synthetic methods. Thus, for example, a long double-stranded molecule may be synthesized as several smaller segments of appropriate complementarity. Complementary segments thus produced may be annealed such that each segment possesses appropriate cohesive termini for attachment of an adjacent segment. Adjacent segments may be ligated by annealing cohesive termini in the presence of DNA ligase to construct an entire long double-stranded molecule. A synthetic DNA molecule so constructed may then be cloned and amplified in an appropriate vector.

HGFIN genes also may be isolated from appropriate biological sources using methods known in the art. In the exemplary embodiment of the invention, HGFIN may be isolated from genomic libraries of human, mouse, bovine or rat. In alternative embodiments, cDNA clones of HGFIN may be isolated, such as what has been isolated from human, for instance from: murine, bovine and rat cDNA libraries. A preferred means for isolating HGFIN genes is PCR amplification using genomic or cDNA templates and HGFIN specific primers. Genomic and cDNA libraries are commercially available, and can also be made by procedures well known in the art. In positions of degeneracy where more than one nucleic acid residue could be used to encode the appropriate amino acid residue, all the appropriate nucleic acid residues may be incorporated to create a mixed oligonucleotide population, or a neutral base such as inosine may be used. The strategy of oligonucleotide design is well known in the art.

Alternatively, PCR primers may be designed by the above method to match the coding sequences of a human, murine, bovine, or rat protein and these primers used to amplify the native nucleic acids from isolated cDNA or genomic DNA.

In accordance with the present invention, nucleic acids having the appropriate level sequence homology (i.e., 70% identity or greater) with part or all the coding regions of SEQ ID NO:1 may be identified by using hybridization and washing conditions of appropriate stringency. For example, hybridizations may be performed, according to the method of Sambrook et al., using a hybridization solution comprising: 1.0% SDS, up to 50% formamide, 5×SSC (150 mM NaCl, 15 mM trisodium citrate), 0.05% sodium pyrophosphate (pH 7.6), 5×Denhardt's solution, and 100 microgram/ml denatured, sheared salmon sperm DNA. Hybridization is carried out at 37-42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes to 1 hour at 37° C. in 2×SSC and 0.1% SDS; (4) 2 hours at 45-55° C. in 2×SSC and 0.1% SDS, changing the solution every 30 minutes.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated $T_m$ of the of the hybrid. Wash conditions should be as stringent as possible for the degree of identity of the probe for the target. In general, wash conditions are selected to be approximately 12-20° C. below the $T_m$ of the hybrid. In regards to the nucleic acids of the current invention, a moderate stringency hybridization is defined as hybridization in 6×SSC, 5×Denhardt's solution, 0.5% SDS and 100 µg/ml denatured salmon sperm DNA at 42° C., and wash in 2×SSC and 0.5% SDS at 55° C. for 15 minutes. A high stringency hybridization is defined as hybridization in 6×SSC, 5×Denhardt's solution, 0.5% SDS and 100 µg/ml denatured salmon sperm DNA at 42° C., and wash in 1×SSC and 0.5% SDS at 6-5° C. for 15 minutes. Very high stringency hybridization is defined as hybridization in 6×SSC, 5×Denhardt's solution, 0.5% SDS and 100 µg/ml denatured salmon sperm DNA at 42° C., and wash in 0.1 SSC and 0.5% SDS at 65° C. for 15 minutes.

Nucleic acids of the present invention may be maintained as DNA in any convenient cloning vector. In a preferred embodiment, clones are maintained in plasmid cloning/expression vector, such as PBLUESCRIPT (STRATAGENE, La Jolla, Calif.), that is propagated in a suitable *E. coli* host cell.

The HGFIN polynucleotides may be used for a variety of purposes in accordance with the present invention. DNA, cDNA or RNA, or fragments thereof may be used as probes to detect the presence of and/or expression of HGFIN genes. Methods in which HGFIN nucleic acids may be utilized as probes for such assays include, but are not limited to: (1) in situ hybridization; (2) Southern hybridization (3) northern hybridization; and (4) assorted amplification reactions such as polymerase chain reaction (PCR).

The HGFIN nucleic acids may also be utilized as probes to identify related genes from other species. As is well-known in the art, hybridization stringencies may be adjusted to allow hybridization of nucleic acid probes with complementary sequences of varying degrees of homology.

As described above, HGFIN nucleic acids may be used to produce large quantities of substantially pure HGFIN proteins, or selected portions thereof.

The HGFIN nucleic acids of the present invention can be used to identify and isolate other members involved in the hematopoietic response to various members of the tachykinin family, in which HGFIN may be involved. A yeast two-hybrid system can be used to identify proteins that physically interact with the HGFIN protein, as well as isolate their nucleic acids. In this system, the coding sequence of the protein of interest is operably linked to the coding sequence of half of an activator protein. This construct is used to transform a yeast cell library that has been transformed with DNA constructs that contain the coding sequence for the other half of the activator protein operably linked to a random coding sequence from the organism of interest. When the protein made by the random coding sequence from the library interacts with the protein of interest, the two halves of the activator protein are physically associated and form a functional unit that activates the reporter gene.

In accordance with the present invention, all or part of the human HGFIN coding sequence may be operably linked to the coding sequence of the first half of the activator, and the library of random coding sequences may be constructed with cDNA from human and operably linked to the coding sequence of the second half of the activator protein. Several activator protein/reporter genes are customarily used in the yeast two hybrid system, the Gal4/LacZ system (see Clark et al. (1998) *Proc. Natl. Acad. Sci. USA* 95:5401-5406), among others.

The nucleotide sequences of the present invention are also valuable for chromosome localization. The sequence is specifically targeted to, and can hybridize with, a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. The relationship between genes and diseases that have been mapped to the same chromosomal region are then identified through linkage analysis (co-inheritance of physically adjacent genes).

In one aspect, the present invention relates to human HGFIN polypeptides (or HGFIN proteins). The human HGFIN polypeptides include the polypeptide of SEQ ID NO:2; as well as polypeptides comprising the amino acid sequence of SEQ ID NO:2; and polypeptides comprising the amino acid sequences which have at least 70% identity to that of SEQ ID NO:2, over its entire length. Preferably, an HGFIN polypeptide exhibits at least one biological activity of HGFIN. The present invention further provides for a polypeptide which comprises an amino acid sequence which has at least 80% identity, more preferably at least 90% identity, yet more preferably at least 95% identity, most preferably at least 97-99% identity, to that of SEQ ID NO:2 over the entire length of SEQ ID NO:2.

Figure 1A:
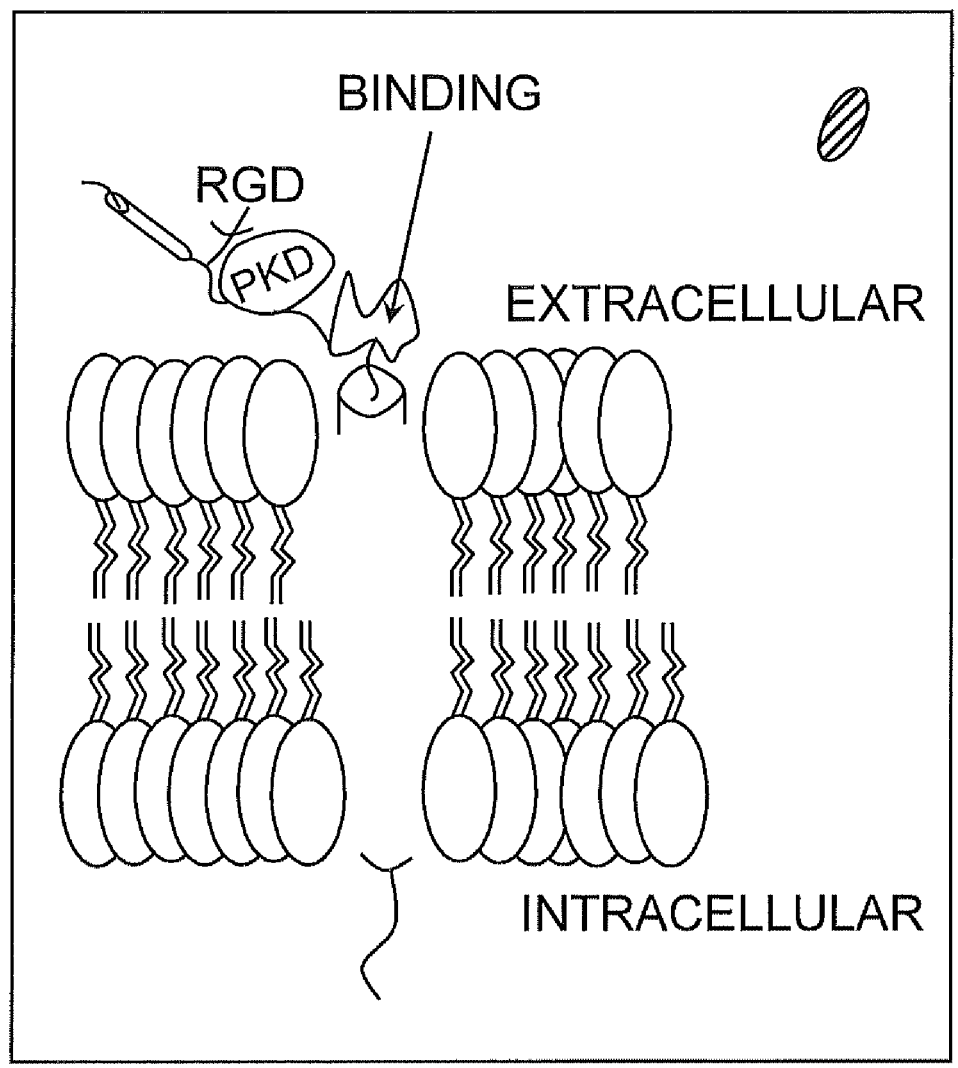
FIG. 1A is a spatial arrangement of the HGFIN protein within a lipid bilayer.

As stated above, the HGFIN gene and protein of the present invention share a portion of sequence homology to the PKD portion of the NK-1 receptor. The HGFIN coding sequence predicted that the most probable translational product was equivalent to 560 residues. Based on the results of ProSite, the HGFIN protein contains several stretches of glycosylated residues in the extracellular portion (FIG. 1). Both TMHMM (Sonnhammer, et al. (1998) supra) and PHDhtm. (Rost & Sander (1993) supra; Rost & Sander (1994) supra) programs predicted that residues 485-508 are transmembrane. TMHMM suggests that residues 1-485 are extracellular, and residues 509-560 are intracellular.

General structural analysis of HGFIN through PredictProtein gained further insights on the characteristics and molecular structure (FIG. 2A). Based on GLOBE analyses, the binding domain is predicted to be compact rather than extended. Predator analysis indicated that the extracellular domain consists mainly of extended sheets and loops. There are at least two distinct regions that are thought to form the binding domain (FIG. 2A, extracellular region). The results of structural analysis through PredictProtein matched information from SwissProt on the characteristics of nmb (Accession Q14956), which is 97% homologous to HGFIN. According to ProDom, a large stretch of the extracellular region of HGFIN is homologous to the PMEL-17 class of proteins found in polycystic kidney disorder. One important structural region of these proteins is the PKD region, whose structure is available in the RCSB protein database. The homologous region within HGFIN has been modeled from the PKD region of polycystein-1 (IB4R). The 3-D model of the PKD region within HGFIN was constructed using GeneMine Look 3.5 homology modeling algorithm.

The HGFIN polypeptides may be in the form of the "mature" protein or may be a part of a larger protein such as a fusion protein. It is often advantageous to include an additional amino acid sequence which contains secretory or leader sequences, pro-sequences, sequences which aid in purification such as multiple histidine residues, or an additional sequence for stability during recombinant production.

Fragments of the HGFIN polypeptides are also included in the invention. A fragment is a polypeptide having an amino acid sequence that entirely is the same as part, but not all, of the amino acid sequence of the aforementioned HGFIN polypeptides. Preferred fragments include, for example, truncation polypeptides having the amino acid sequence of HGFIN polypeptides, except for deletion of a continuous series of residues that includes the amino terminus, or a continuous series of residues that includes the carboxyl terminus or deletion of two continuous series of residues, one including the amino terminus and one including the carboxyl terminus. Also preferred are fragments characterized by structural or functional attributes such as fragments that comprise alpha-helix and alpha-helix forming regions, beta-sheet and beta-sheet forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Other preferred fragments are biologically active fragments. Biologically active fragments are those that mediate HGFIN activity, including those with a similar activity or an improved activity, or with a decreased undesirable activity. Also included are those that are antigenic or immunogenic in an animal, especially in a human.

Preferably, all of these polypeptide fragments retain the biological activity of the HGFIN, including antigenic activity. Variants of the defined sequence and fragments also form part of the present invention. Preferred variants are those that vary from the referents by conservative amino acid substitutions.

The HGFIN proteins and polypeptides of the invention can be prepared in any suitable manner. If produced in situ, the polypeptides may be purified from appropriate sources, e.g., appropriate vertebrate cells including mammalian cells from human, mouse, bovine or rat.

Alternatively, the availability of nucleic acid molecules encoding the polypeptides enables production of the proteins using in vitro expression methods known in the art. For example, a cDNA or gene may be cloned into an appropriate in vitro transcription vector, for in vitro transcription, followed by cell-free translation in a suitable cell-free translation system. In vitro transcription and translation systems are commercially available, e.g., from PROMEGA Biotech, Madison, Wis.; or BRL, Rockville, Md. While in vitro transcription and translation may not be ideal for preparing large quantities of the protein, it is ideal for preparing small amounts of native or mutant proteins for research purposes, particularly since it allows the incorporation of radioactive nucleotides.

According to a preferred embodiment, larger quantities of HGFIN encoded polypeptide may be produced by expression in a suitable prokaryotic or eukaryotic system. For example, part or all of a DNA molecule, such as the coding portion of SEQ ID NO:1 may be inserted into a plasmid vector adapted for expression in a bacterial cell (such as *E. coli*) or a yeast cell (such as *Saccharomyces cerevisiae*), or into a baculovirus vector for expression in an insect cell. Such vectors contain the regulatory elements necessary for expression of the DNA in the host cell, positioned in such a manner as to permit expression of the DNA into the host cell. Such regulatory elements required for expression include promoter sequences, transcription initiation sequences and, optionally, enhancer sequences.

Secretion signals may be used to facilitate purification of the resulting protein. The coding sequence for the secretion peptide is operably linked to the 5' end of the coding sequence for the protein, and this hybrid nucleic acid molecule is inserted into a plasmid adapted to express the protein in the host cell of choice. Plasmids specifically designed to express and secrete foreign proteins are available from commercial sources. For example, if expression and secretion is desired in *E. coli*, commonly used plasmids include pTrcPPA (Pharmacia); pPROK-C and pKK233-2 (Clontech); and pNH8a, pNH16a, pcDNAII and pAX (Stratagene), among others.

The HGFIN proteins produced by in vitro transcription and translation or by gene expression in a recombinant procaryotic or eukaryotic system may be purified according to methods known in the art. Recombinant proteins can be purified by affinity separation, such as by immunological interaction with antibodies that bind specifically to the recombinant protein or fusion proteins such as His tags, as described herein. Such methods are commonly used by skilled practitioners.

As mentioned, the proteins can be produced and fused to a "tag" protein in order to facilitate subsequent purification. These fusion proteins are produced by operably-linking the nucleic acid coding sequence of the "tag" protein to the coding sequence of the protein of interest, and expressing the fused protein by standard methods. Systems are commercially available that comprise a plasmid containing an expression cassette with the "tag" protein coding sequence and a polylinker into which a coding sequence of interest can be operably ligated. These fusion protein systems further provide chromatography matrices or beads that specifically bind the "tag" protein thereby facilitating the fusion protein purification. These fusion protein systems often have the recognition sequence of a protease at or near the junction of the "tag" protein and the protein of interest so that the "tag" protein can be removed if desired. Fusion protein systems include, but are not limited to, the His-6-tag system (Qiagen) and the glutathione-S-transferase system (Pharmacia).

The HGFIN proteins of the invention, prepared by one of the aforementioned methods, may be analyzed according to standard procedures. For example, the protein may be subjected to amino acid composition, amino acid sequence, or protein concentration analysis according to known methods.

Using appropriate amino acid sequence information, synthetic HGFIN proteins of the present invention may be prepared by various synthetic methods of peptide synthesis via condensation of one or more amino acid residues, in accordance with conventional peptide synthesis methods. Preferably, peptides are synthesized according to standard solid-phase methodologies, such as may be performed on an Applied Biosystems Model 430A peptide synthesizer (Applied Biosystems, Foster City, Calif.), according to manufacturer's instructions. Other methods of synthesizing peptides or peptidomimetics, either by solid phase methodologies or in liquid phase, are well known to those skilled in the art.

The HGFIN protein can be used as a label in many in vitro applications currently used. Purified HGFIN can be covalently linked to other proteins by methods well-known in the art, and used as a marker protein. The purified HGFIN protein can be covalently linked to a protein of interest in order to determine localization. In particularly preferred embodiments, a linker of 4 to 20 amino acids is used to separate HGFIN from the desired protein. This application may be used in living cells by micro-injecting the linked proteins. The HGFIN may also be linked to antibodies and used thus for localization in fixed and sectioned cells. The HGFIN may be linked to purified cellular proteins and used to identify binding proteins and nucleic acids in assays in vitro, using methods well known in the art.

The HGFIN protein can also be linked to nucleic acids and used to advantage. Applications for nucleic acid-linked HGFIN include, but are not limited, to FISH (fluorescent in situ hybridization), and labeling probes in standard methods utilizing nucleic acid hybridization.

The HGFIN proteins of the present invention can be used to identify binding partners of HGFIN. In these assays, the first protein of interest is allowed to form a physical interaction with the unknown binding protein(s), often in a heterologous solution of proteins. The complex of proteins is then isolated, and the nature of the protein complex is determined. This procedure is greatly facilitated by a simple method for isolating the HGFIN protein. For example, immunologically-specific antibodies can be used to precipitate the HGFIN protein, or the HGFIN protein can be bound to beads that can be easily purified. Such beads can be magnetized, or simply dense enough to be separated from the non-associated protein by centrifugation.

In preferred embodiments, the compositions of the invention further comprise a solid support to which the moiety detecting the HGFIN mRNA or protein is or can be attached. In certain embodiments, attachment of the detecting moiety, e.g., an antibody, nucleic acid or protein probe, is via a covalent linkage with the solid support. In other embodiments, attachment may be via a non-covalent linkage, for example, between members of a high affinity binding pair. Many examples of high affinity binding pairs are known in the art, and include biotin/avidin, ligand/receptor, and antigen/antibody pairs.

In particular aspects, the invention relates to compositions and methods for using such polypeptides and polynucleotides for treating diseases associated with increased cell proliferation, by administering a HGFIN gene or protein, in a pharmaceutically acceptable and appropriate delivery vehicle, to increase cell differentiation. Further, the compositions and methods of the present invention may be used for treating a disease associated with decreased cell proliferation by administering a HGFIN antisense sequence, in a pharmaceutically acceptable and appropriate delivery vehicle. The invention also provides immunospecific antibodies to the HGFIN protein that may be used in therapeutic compositions and methods, by themselves, or in conjugation with other therapeutic or cyto-radiotoxic agents. The compositions and methods of the present invention may also be useful in reducing the side effects of traditional chemo-radio therapies by administering a HGFIN gene, protein, or antisense sequence in conjunction with the chemo-radio therapy to thereby reduce the amount of toxic dosage needed to kill cells.

Hence, the present invention also relates to vectors that harbor a polynucleotide or polynucleotides of the present invention, and host cells that are genetically engineered with vectors of the invention and to the production of polypeptides of the invention by recombinant techniques both in vitro and in vivo, as well as ex vivo procedures. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. In accordance with the methods of the present invention, host cells may also be obtained from the bone marrow of a subject by procedures well known in the medical arts. Introduction of polynucleotides into host cells can then be effected by methods described in many standard laboratory manuals, such as Davis et al. (1986) *Basic Methods In Molecular Biology* and Sambrook et al. (1989) *Molecular Cloning: A Laboratory Manual*, $2^{nd}$ Ed., Cold Spring Harbor Laboratory Press, Cold Spring Harbor, N.Y. Such methods include calcium phosphate transfection, DEAE-dextran mediated transfection, microinjection, cationic lipid-mediated transfection, electroporation, transduction, scrape loading, ballistic introduction and infection.

Representative examples of appropriate hosts for in vitro procedures include bacterial cells, such as streptococci, staphylococci, *E. coli, Streptomyces* and *Bacillus subtilis* cells; fungal cells, such as yeast cells and *Aspergillus* cells, insect cells such as *Drosophila* S2 and *Spodoptera* Sf9 cells; animal cells such as CHO, COS, HeLa, C127, 3T3, BHK, HEK 293 and Bowes melanoma cells, and plant cells. The selection of an appropriate host is deemed to be within the scope of those skilled in the art from the teachings herein.

More particularly, the present invention also includes recombinant constructs comprising a HGFIN DNA, cDNA or RNA sequence as well as compliment nucleotide sequences for triplexing duplex DNA. The construct comprises a vector, such as a plasmid or viral vector, into which the clone has been inserted, in a forward or reverse orientation. In a preferred aspect of this embodiment, the construct further comprises regulatory sequences, including, for example, a promoter, operably linked to the genetic sequence. Large numbers of suitable vectors and promoters are known to those of skill in the art, and are commercially available. The following vectors are provided by way of example; Bacterial: pQE70, pQE60, pQE-9 (Qiagen), pBS, pD10, PHAGESCRIPT, psiX 174, PBLUESCRIPT SK, PBLUESCRIPT KS, pNH8A, pNH 16a, pNH18A, pNH46A (Stratagene); ptrc99a, pKK223-3, pKK233-3, pDR540, pRIT5 (Pharmacia); Eukaryotic: pWLNEO, pSV2CAT, pOG44, PXTI, pSG (Stratagene) pSVK3, pBPV, pMSG, pSVL (Pharmacia). As further examples, cDNA of human HGFIN may be inserted in the pEF/myc/cyto vector (from Invitrogen) and/or the pCMV-Tag3b vector (from Stratagene), which can then be used with anti-Myc Ab, to transform stem or Hela (or other) cells with the HGFIN DNA. The protein HGFIN produced may be purified from the cells and directly injected to the bone marrow tissue, infused to blood cells, or delivered in a lyophilized carrier as described herein.

However, any other plasmid or vector may be used as long as they are replicable and viable in the host. In addition, a complete mammalian transcription unit and a selectable marker can be inserted into a prokaryotic plasmid for use in in vivo procedures. The resulting vector is then amplified in bacteria before being transfected into cultured mammalian cells or delivered directly to the subject with an acceptable biological carrier as described below. Examples of vectors of this type include pTK2, pHyg and pRSVneo. Hence, these plasmids, constructs and vectors may be used in both in vivo and ex vivo procedures. Ex vivo procedures involve the removal of a host cell, such as a bone marrow, stromal or stem cell, from the subject, recombinant manipulation of the cell (i.e., transformation, transduction or transfection with a suitable HGFIN expression system vector), and the re-delivery of the cell back into its host environment.

Further, according to one particular embodiment of the present invention, recombinant HGFIN DNA, cDNA, RNA, or polynucleotide sequence coding for the antisense sequence encoding the protein, may be directly injected to the bone marrow for the production or inhibition of HGFIN endogenously. DNA, cDNA, RNA or polynucleotide sequences coding for the antisense sequence encoding the protein may also be delivered using other appropriate means, including vectors, as described below, and well known in the recombinant arts.

A wide variety of recombinant plasmids may be engineered to express the HGFIN protein and used to deliver HGFIN to a cell. These include the use of naked DNA and HGFIN plasmids to directly transfer genetic material into a cell; formulations of HGFIN encoding trapped liposomes or in proteoliposomes that contain other viral envelope receptor proteins; and HGFIN-encoding DNA, or antisense sequence, coupled to a polysine-glycoprotein carrier complex. Hence methods for the delivery of nucleotide sequences to cells are well-known in the recombinant arts. Such methods for in vitro delivery, further include, but are not limited to: microinjection, calcium phosphatase, lyposomes, and electroporation.

Genetic material, such as the nucleotides of the present invention, may be delivered to cells, in vivo, using various different plasmid based delivery platforms, including but not limited to recombinant ADV (such as that described in U.S. Pat. No. 6,069,134), AAV (such as those described by U.S. Pat. No. 5,139,941), MMLV, Herpes Simplex Virus (U.S. Pat. No. 5,288,641), cytomegalovirus, lentiviral, and overall, retroviral gene delivery systems, well known and practiced with in the art.

Techniques for preparing replication defective, infective viruses are well-known in the art. These systems typically include a plasmid vector including a promoter sequence (such as CMV early promoter) operably linked to the nucleotide coding the gene of interest (inserted into an appropriate gene insertion site; i.e., an IRES site), as well as a terminating signal (such as a Poly-A tail, i.e., BGH), and the appropriate mutations so as to make the delivery vehicle replication defective (e.g., Psi sequence deletions) and safe for therapeutic uses. The construction of the appropriate elements in a vector system containing the nucleotides of the present invention is well within the skills of one versed in the recombinant arts.

A great variety of vector and/or expression systems can be used. Such systems include, among others, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia, viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al. (1989) supra).

Promoter regions can be selected from any desired gene using CAT (chloramphenicol acetyl transferase) vectors or other vectors with selectable markers. Two appropriate vectors are pKK232-8 and pCM7. Particular named bacterial promoters include lacI, lacZ, T3, T7, gpt, lambda PR, PL and trp. Eukaryotic promoters include CMV immediate early, HSV thymidine kinase, early and late SV40, LTRs from retrovirus, and mouse metallothionein-1. Selection of the appropriate vector and promoter is well within the level of ordinary skill in the art.

For secretion of the translated protein into the lumen of the endoplasmic reticulum, into the periplasmic space or into the extracellular environment, appropriate secretion signals may be incorporated into the desired polypeptide. These signals may be endogenous to the polypeptide or they may be heterologous signals.

If the HGFIN polypeptide is to be expressed for use in screening assays, generally, it is preferred that the polypeptide be produced at the surface of the cell. In this event, the cells may be harvested prior to use in the screening assay. If the HGFIN polypeptide is secreted into the medium, the medium can be recovered in order to recover and purify the polypeptide; if produced intracellularly, the cells must first be lysed before the polypeptide is recovered. The HGFIN polypeptides can be recovered and purified from recombinant cell cultures by well known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well-known techniques for refolding proteins may be employed to regenerate active conformation when the polypeptide is denatured during isolation and or purification.

Further still, the recombinant HGFIN DNA, cDNA, RNA or polynucleotide sequences coding for the antisense sequence encoding the protein, may be delivered to the cells of the bone marrow for the production or inhibition of HGFIN endogenously, by use of biologically compatible carriers or excipients. This may be useful in inducing or inhibiting cell differentiation and/or possibly proliferation. Pharmaceutically acceptable carriers for therapeutic use are well-known in the pharmaceutical art, and are described, for example, in Remington's Pharmaceutical Sciences ((1985) Gennaro, ed.). For example, sterile saline or phosphate-buffered saline at physiological pH may be used. Preservatives, stabilizers, dyes, and even flavoring agents may be provided in the pharmaceutical composition. For example, sodium benzoate, sorbic acid, and esters of p-hydroxybenzoic acid may be added as preservatives. Antioxidants and suspending agents may also be used.

The above-described constructs, plasmids and vectors are useful in gene therapy procedures. Successful gene therapy generally requires the integration of a gene able to correct the genetic disorder into the host genome, where it would coexist and replicate with the host DNA and be expressed at a level to compensate for the defective gene. Ideally, the disease would be cured by one or a few treatments, with no serious side effects. There are several approaches to gene therapy proposed.

As described above, basic transfection methods exist in which DNA containing the gene of interest is introduced into cells non-biologically, for example, by permeabilizing the cell membrane physically or chemically. Liposomes or protein conjugates formed with certain lipids and amphophilic peptides can be used for transfection. This approach is particularly effective in ex vivo procedures involving leukocytes, which can be temporarily removed from the body and can tolerate the cytotoxicity of the treatment.

A second, transduction approach, capitalizes on the natural ability of viruses to enter cells, bringing their own genetic material with them. For example, retroviruses have promise as gene delivery vectors due to their ability to integrate their genes into the host genome, transferring a large amount of foreign genetic material, infecting a broad spectrum of species and cell types and, of being packaged in special cell-lines.

A third method uses other viruses, such as adenovirus, herpes simplex viruses (HSV), cytomegalovirus (CMV), and adeno-associated virus (AAV), which are engineered to serve as vectors for gene transfer. Although some viruses that can accept foreign genetic material are limited in the number of nucleotides they can accommodate and in the range of cells they infect, these viruses have been demonstrated to successfully effect gene expression. For example, adenovirus gene transfer systems may be used. Such a system is based upon recombinant, engineered adenovirus which is rendered replication-incompetent by deletion of a portion of its genome, such as E1, and yet still retains its competency for infection. Relatively large foreign proteins can be expressed when additional deletions are made in the adenovirus genome. For example, adenoviruses deleted in both E1 and E3 regions are capable of carrying up to 10 Kb of foreign DNA and can be grown to high titers in 293 cells. Surprisingly, persistent expression of transgenes following adenoviral infection has also been reported.

The pharmaceutical compositions of the present invention may be formulated and used as tablets, capsules, or elixirs for oral administration; suppositories for rectal or vaginal administration; sterile solutions and suspensions for parenteral administration; creams, lotions, or gels for topical administration; aerosols or insufflations for intratracheobronchial administration; and the like. Preparations of such formulations are well known to those skilled in the pharmaceutical arts. The dosage and method of administration can be tailored to achieve optimal efficacy and will depend on factors that those skilled in the medical arts will recognize.

When administration is to be parenteral, such as intravenous on a daily basis, injectable pharmaceuticals may be prepared in conventional forms, either as liquid solutions or suspensions; solid forms suitable for solution or suspension in liquid prior to injection; or as emulsions. Suitable excipients are, for example, water, saline, dextrose, mannitol, lactose, lecithin, albumin, sodium glutamate, cysteine hydrochloride, or the like. In addition, if desired, the injectable pharmaceutical compositions may contain minor amounts of nontoxic auxiliary substances, such as wetting agents, pH buffering agents, and the like. If desired, absorption enhancing preparations (e.g., liposomes) may be utilized.

Hence, in another preferred embodiment the present invention is directed to a novel pharmaceutical composition that includes a biologically acceptable carrier along with an effective amount of a HGFIN DNA, cDNA, RNA or protein for the treatment and/or prevention of diseases associated with a lack of progenitor cell differentiation. The pharmaceutical composition includes a HGFIN sequence substantially identical to SEQ ID NO:1 and/or a protein encoded by an amino acid sequence substantially identical to the sequence of SEQ ID NO:2. For the treatment of and/or prevention of diseases associated with an unhealthy increase in progenitor cell differentiation, a pharmaceutical composition that includes an effective amount of a nucleotide sequence coding for the antisense sequence of SEQ ID NO:1, may be administered. An example of such diseased state that may be treated by the compositions of the present invention are leukemia and lymphoma. Hence, methods for the treatment of diseases associated with an unhealthy increase or lack of stem or progenitor cell differentiation in a subject are also provided. These methods involve administering to the subject a pharmaceutical composition that includes an effective amount of a HGFIN protein or a nucleotide sequence coding for the HGFIN protein or a nucleotide sequence that codes for the anti-sense sequence of the nucleotide sequence coding for the HGFIN protein. These may be delivered by suitable means, as described above, including the use of vectors and or acceptable biological carriers. The above disclosed vectors may be targeted preferentially to different forms of lymphoproliferative diseases by use of antibodies that recognize specific epitopes on the cell surface of these abnormal cells. The production and use of such antibodies are well known in the recombinant arts but include, for example anti-CD20, for B-cell lymphoma; anti-CD52 for Chronic Lymphocytic Leukemia; Anti-CD33 linked to a chemotherapeutic agent (calicheamicin), for Acute Myeloid Leukemia; and an IL-2 gene linked to diphtheria toxin, for T-cell lymphoma.

The present invention also provides antibodies capable of immunospecifically binding to polypeptides of the invention. Polyclonal or monoclonal antibodies directed toward the polypeptide encoded by HGFIN may be prepared according to standard methods. Monoclonal antibodies may be prepared according to general hybridoma methods of Kohler and Milstein (1975) *Nature* 256:495-497), the trioma technique, the human B-cell hybridoma technique (Kozbor et al. (1983) *Immunology Today* 4:72) or the EBV-hybridoma technique (Cole et al. (1985) *Monoclonal Antibodies And Cancer Therapy*, pp. 77-96, Alan R. Liss, Inc.).

Antibodies used in the present invention may be polyclonal antibodies, although monoclonal antibodies are preferred because they may be reproduced by cell culture or recombinantly, and may be modified to reduce their antigenicity. Polyclonal antibodies may be raised by a standard protocol by injecting a production animal with an antigenic composition, formulated as described above. See, e.g., Harlow and Lane (1988) *Antibodies: A Laboratory Manual*, Cold Spring Harbor Laboratory. In one such technique, a HGFIN antigen comprising an antigenic portion of the HGFIN polypeptide is initially injected into any of a wide variety of mammals (e.g., mice, rats, rabbits, sheep or goats). Alternatively, in order to generate antibodies to relatively short peptide portions of HGFIN, a superior immune response may be elicited if the polypeptide is joined to a carrier protein, such as ovalbumin, BSA or KLH. The peptide-conjugate is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Alternatively, for monoclonal antibodies, hybridomas may be formed by isolating the stimulated immune cells, such as those from the spleen of the inoculated animal. These cells are then fused to immortalized cells, such as myeloma cells or transformed cells, which are capable of replicating indefinitely in cell culture, thereby producing an immortal, immunoglobulin-secreting cell line. The immortal cell line utilized is preferably selected to be deficient in enzymes necessary for the utilization of certain nutrients. Many such cell lines (such as myelomas) are known to those skilled in the art, and include, for example: thymidine kinase (TK) or hypoxanthine-guanine phosphoriboxyl transferase (HGPRT). These deficiencies allow selection for fused cells according to their ability to grow on, for example, hypoxanthine aminopterinthymidine medium (HAT).

Preferably, the immortal fusion partners utilized are derived from a line that does not secrete immunoglobulin. The resulting fused cells, or hybridomas, are cultured under conditions that allow for the survival of fused, but not unfused, cells and the resulting colonies screened for the production of the desired monoclonal antibodies. Colonies producing such antibodies are cloned, expanded, and grown so as to produce large quantities of antibody, see Kohler and Milstein (1975) supra).

Large quantities of monoclonal antibodies from the secreting hybridomas may then be produced by injecting the clones into the peritoneal cavity of mice and harvesting the ascites fluid therefrom. The mice, preferably primed with pristine, or some other tumor-promoter, and immunosuppressed chemically or by irradiation, may be any of various suitable strains known to those in the art. The ascites fluid is harvested from the mice and the monoclonal antibody purified therefrom, for example, by CM SEPHAROSE column or other chromatographic means. Alternatively, the hybridomas may be cultured in vitro or as suspension cultures. Batch, continuous culture, or other suitable culture processes may be utilized. Monoclonal antibodies are then recovered from the culture medium or supernatant.

In addition, the antibodies or antigen binding fragments may be produced by genetic engineering. In this technique, as with the standard hybridoma procedure, antibody-producing cells are sensitized to the desired antigen or immunogen. The messenger RNA isolated from the immune spleen cells or hybridomas is used as a template to make cDNA using PCR amplification. A library of vectors, each containing one heavy chain gene and one light chain gene retaining the initial antigen specificity, is produced by insertion of appropriate sections of the amplified immunoglobulin cDNA into the expression vectors. A combinatorial library is constructed by combining the heavy chain gene library with the light chain gene library. This results in a library of clones which co-express a heavy and light chain (resembling the Fab fragment or antigen binding fragment of an antibody molecule). The vectors that carry these genes are co-transfected into a host (e.g., bacteria, insect cells, mammalian cells, or other suitable protein production host cell). When antibody gene synthesis is induced in the transfected host, the heavy and light chain proteins self-assemble to produce active antibodies that can be detected by screening with the antigen or immunogen.

Chimeric antibodies may be made by recombinant means by combining the murine variable light and heavy chain regions (VK and VH), obtained from a murine (or other animal-derived) hybridoma clone, with the human constant light and heavy chain regions, in order to produce an antibody with predominantly human domains. The production of such chimeric antibodies is well-known in the art, and may be achieved by standard means (as described, e.g., in U.S. Pat. No. 5,624,659) Humanized antibodies are engineered to contain even more human-like immunoglobulin domains, and incorporate only the complementarity-determining regions of the animal-derived antibody. This is accomplished by carefully examining the sequence of the hyper-variable loops of the variable regions of the monoclonal antibody, and fitting them to the structure of the human antibody chains. Although facially complex, the process is straightforward in practice. See, e.g., U.S. Pat. No. 6,187,287.

In a preferred embodiment, antibodies are prepared, which react immunospecifically with various epitopes of the HGFIN encoded polypeptides. These above-described antibodies may be employed to isolate or to identify clones expressing the polypeptide or to purify the polypeptides by affinity chromatography. Further, these antibodies may be used for therapeutic purposes by binding to the endogenous HGFIN receptor and thereby impeding the binding of the natural ligand, where it is desirable to inhibit leukocyte proliferation. Specific antibodies may be made in vivo using recombinant DNA and methods well know in the art.

Antibodies that are immunologically specific to HGFIN proteins, or specific epitopes thereof, may be utilized in affinity chromatography to isolate the HGFIN protein, to quantify the protein utilizing techniques such as western blotting and ELISA, or to immunoprecipitate HGFIN from a sample containing a mixture of proteins and other biological materials. The immunoprecipitation of HGFIN is particularly advantageous when utilized to isolate binding partners of HGFIN, as described above. Antibodies against HGFIN polypeptides may also be employed to treat diseases associated with an increased rate of differentiation of progenitor cells, namely, the various lymphoproliferative diseases detailed above, among other hematopoietic pathological conditions.

As described above, the HGFIN antibodies for use in the present invention have utility on their own without conjugation, if they alter the native activity of HGFIN in the aberrant cells. Such antibodies, which may be selected as described above, may be utilized without further modification to include a cytotoxic moiety. These types of compositions have the advantage of reduced toxicity (in that only the toxicity of the antibody moieties themselves must be taken into account when dosing), and are simpler to manufacture. Thus, non-conjugated activity altering anti-HGFIN antibody therapeutics are a preferred embodiment of the invention. However, the conjugation of cytotoxic agents is yet another preferred embodiment when utilizing these antibodies, as the added moieties also add functionality to the therapeutic. Further, the antibodies of the present invention can be used as a delivery vehicle to target the delivery of other various elements (i.e., a genetic sequence encoding a HGFIN polynucleotide or its antisense sequence) to HGFIN expressing cells.

In certain preferred embodiments of the invention, the anti-HGFIN antibodies may be coupled or conjugated to one or more therapeutic or cytotoxic moieties. As used herein, "cytotoxic moiety" simply means a moiety that inhibits cell growth or promotes cell death when proximate to or absorbed by the cell. Suitable cytotoxic moieties in this regard include radioactive isotopes (radionuclides), chemotoxic agents such as differentiation inducers, inhibitors and small chemotoxic drugs, toxin proteins and derivatives thereof, as well as the nucleotide sequences (or their antisense sequence) of the present invention.

In general, therapeutic agents may be conjugated to the anti-HGFIN moiety by any suitable technique, with appropriate consideration of the need for pharmokinetic stability and reduced overall toxicity to the patient. A therapeutic agent may be coupled to a suitable antibody moiety either directly or indirectly (e.g., via a linker group). A direct reaction between an agent and an antibody is possible when each possesses a functional group capable of reacting with the other. For example, a nucleophilic group, such as an amino or sulfhydryl group, may be capable of reacting with a carbonyl-containing group, such as an anhydride or an acid halide, or with an alkyl group containing a good leaving group (e.g., a halide). Alternatively, a suitable chemical linker group may be used. A linker group can function as a spacer to distance an antibody from an agent in order to avoid interference with binding capabilities. A linker group can also serve to increase the chemical reactivity of a substituent on a moiety or an antibody, and thus increase the coupling efficiency. An increase in chemical reactivity may also facilitate the use of moieties, or functional groups on moieties, which otherwise would not be possible.

Suitable linkage chemistries include maleimidyl linkers and alkyl halide linkers (which react with a sulfhydryl on the antibody moiety) and succinimidyl linkers (which react with a primary amine on the antibody moiety). Several primary amine and sulfhydryl groups are present on immunoglobulins, and additional groups may be designed into recombinant immunoglobulin molecules. It will be evident to those skilled in the art that a variety of bifunctional or polyfunctional reagents, both homo- and hetero-functional (such as those provided by the Pierce Chemical Co., Rockford, Ill.), may be employed as a linker group. Coupling may be effected, for example, through amino groups, carboxyl groups, sulfhydryl groups or oxidized carbohydrate residues. There are numerous references describing such methodology, e.g., U.S. Pat. No. 4,671,958.

As an alternative coupling method, cytotoxic agents may be coupled to the anti-HGFIN antibody moiety through an oxidized carbohydrate group at a glycosylation site, as described in U.S. Pat. Nos. 5,057,313 and 5,156,840. Yet another alternative method of coupling the antibody moiety to the cytotoxic or imaging moiety is by the use of a non-covalent binding pair, such as streptavidin/biotin, or avidin/biotin. In these embodiments, one member of the pair is covalently coupled to the antibody moiety and the other member of the binding pair is covalently coupled to the cytotoxic or imaging moiety.

Where a cytotoxic moiety is more potent when free from the antibody portion of the immunoconjugates of the present invention, it may be desirable to use a linker group which is cleavable during or upon internalization into a cell, or which is gradually cleavable over time in the extracellular environment. A number of different cleavable linker groups have been described. The mechanisms for the intracellular release of a cytotoxic moiety agent from these linker groups include cleavage by reduction of a disulfide bond (e.g., U.S. Pat. No. 4,489,710), by irradiation of a photolabile bond (e.g., U.S. Pat. No. 4,625,014), by hydrolysis of derivatized amino acid side chains (e.g., U.S. Pat. No. 4,638,045), by serum complement-mediated hydrolysis (e.g., U.S. Pat. No. 4,671,958), and acid-catalyzed hydrolysis (e.g., U.S. Pat. No. 4,569,789).

It may be desirable to couple more than one therapeutic, cytotoxic and/or imaging moiety to an antibody. By poly-derivatizing the anti-HGFIN antibody, several cytotoxic strategies may be simultaneously implemented, an antibody may be made useful as a contrasting agent for several visualization techniques, or a therapeutic antibody may be labeled for tracking by a visualization technique. In one embodiment, multiple molecules of a cytotoxic moiety are coupled to one antibody molecule. In another embodiment, more than one type of moiety may be coupled to one antibody. For instance, a therapeutic moiety, such as an HGFIN polynucleotide or antisense sequence, may be conjugated to an antibody in conjunction with a chemotoxic or radiotoxic moiety, to increase the effectiveness of the chemo- or radiotoxic therapy, as well as lowering the required dosage necessary to obtain the desired therapeutic effect. Regardless of the particular embodiment, immunoconjugates with more than one moiety may be prepared in a variety of ways. For example, more than one moiety may be coupled directly to an antibody molecule, or linkers that provide multiple sites for attachment (e.g., dendrimers) can be used. Alternatively, a carrier with the capacity to hold more than one cytotoxic moiety can be used.

As explained, a carrier may bear the agents in a variety of ways, including covalent bonding either directly or via a linker group, and non-covalent associations. Suitable covalent-bond carriers include proteins such as albumins (e.g., U.S. Pat. No. 4,507,234), peptides, and polysaccharides such as aminodextran (e.g., U.S. Pat. No. 4,699,784), each of which have multiple sites for the attachment of moieties. A carrier may also bear an agent by non-covalent associations, such as non-covalent bonding or by encapsulation, such as within a liposome vesicle (e.g., U.S. Pat. Nos. 4,429,008 and 4,873,088). Encapsulation carriers are especially useful in chemotoxic therapeutic embodiments, as they can allow the therapeutic compositions to gradually release a chemotoxic moiety over time while concentrating it in the vicinity of the target cells.

Preferred radionuclides for use as cytotoxic moieties are radionuclides which are suitable for pharmacological administration. Such radionuclides include $^{123}$I, $^{125}$I, $^{131}$I, $^{90}$Y, $^{211}$At, $^{67}$Cu, $^{186}$Re, $^{188}$Re, $^{212}$Pb, and $^{212}$Bi. Iodine and astatine isotopes are more preferred radionuclides for use in the therapeutic compositions of the present invention, as a large body of literature has been accumulated regarding their use. $^{131}$I is particularly preferred, as are other β-radiation emitting nuclides, which have an effective range of several millimeters. $^{123}$I, $^{125}$I, $^{131}$I, or $^{211}$At may be conjugated to antibody moieties for use in the compositions and methods utilizing any of several known conjugation reagents, including Iodogen, N-succinimidyl 3-[$^{211}$At]astatobenzoate, N-succinimidyl 3-[$^{131}$I]iodobenzoate (SIB), and, N-succinimidyl 5-[$^{131}$I]iodob-3-pyridinecarboxylate (SIPC). Any iodine isotope may be utilized in the recited iodo-reagents. Other radionuclides may be conjugated to anti-HGFIN antibody moieties by suitable chelation agents known to those of skill in the nuclear medicine arts.

Preferred chemotoxic agents include small-molecule drugs such as methotrexate, and pyrimidine and purine analogs. Preferred chemotoxin differentiation inducers include phorbol esters and butyric acid. Chemotoxic moieties may be directly conjugated to the anti-HGFIN antibody moiety via a chemical linker, or may encapsulated in a carrier, which is in turn coupled to the anti-HGFIN antibody moiety.

Preferred toxin proteins for use as cytotoxic moieties include ricin, abrin, diphtheria toxin, cholera toxin, gelonin, *Pseudomonas* exotoxin, *Shigella* toxin, pokeweed antiviral protein, and other toxin proteins known in the medicinal biochemistry arts. As these toxin agents may elicit undesirable immune responses in the patient, especially if injected intravascularly, it is preferred that they be encapsulated in a carrier for coupling to the anti-HGFIN antibody moiety.

For administration, the antibody-therapeutic agent will generally be mixed, prior to administration, with a non-toxic, pharmaceutically acceptable carrier substance. Usually, this will be an aqueous solution, such as normal saline or phosphate-buffered saline (PBS), Ringer's solution, lactate-Ringer's solution, or any isotonic physiologically acceptable solution for administration by the chosen means. Preferably, the solution is sterile and pyrogen-free, and is manufactured and packaged under current Good Manufacturing Processes (GMPs), as approved by the FDA. The clinician of ordinary skill is familiar with appropriate ranges for pH, tonicity, and additives or preservatives when formulating pharmaceutical compositions for administration by intravascular injection, intrathecal injection, injection into the bone marrow, direct injection into the aberrant cell, or by other routes. In addition to additives for adjusting pH or tonicity, the antibody-therapeutics agent may be stabilized against aggregation and polymerization with amino acids and non-ionic detergents, polysorbate, and polyethylene glycol.

Optionally, additional stabilizers may include various physiologically-acceptable carbohydrates and salts. Also, polyvinylpyrrolidone may be added in addition to the amino acid. Suitable therapeutic immunoglobulin solutions, which are stabilized for storage and administration to humans, are described in U.S. Pat. No. 5,945,098, incorporated fully herein by reference. Other agents, such as human serum albumin (HSA), may be added to the therapeutic composition to stabilize the antibody conjugates. The compositions of the invention may be administered using any medically appropriate procedure, e.g., intravascular (intravenous, intraarterial, intracapillary) administration, injection into the bone marrow, intracavity or direct injection in the aberrant cell. Intravascular injection may be by intravenous or intraarterial injection.

The effective amount of the therapeutic antibody-conjugate composition to be given to a particular patient will depend on a variety of factors, several of which will be different from patient to patient. A competent clinician will be able to determine an effective amount of a therapeutic antibody-conjugate composition to administer to a patient to retard the growth and promote the death of leukemia/lymphoma associated cells. Dosage of the antibody-conjugate will depend on the treatment of the tumor, route of administration, the nature of the therapeutics, sensitivity of the tumor to the therapeutics, etc. Utilizing LD.sub.50 animal data, and other information available for the conjugated cytotoxic or imaging moiety, a clinician can determine the maximum safe dose for an individual, depending on the route of administration. For instance, an intravenously administered dose may be more than an intrathecally administered dose, given the greater body of fluid into which the therapeutic composition is being administered. Similarly, compositions, which are rapidly cleared from the body, may be administered at higher doses, or in repeated doses, in order to maintain a therapeutic concentration. Utilizing ordinary skill, the competent clinician will be able to optimize the dosage of a particular therapeutic composition in the course of routine clinical trials.

Typically the dosage will be 0.001 to 100 milligrams of conjugate per Kilogram subject body weight. Doses in the range of 0.01 to 1 mg per kilogram of patient body weight may be utilized for a radionuclide therapeutic composition that is administered intrathecally. In a therapeutic example, where the therapeutic composition comprises a $^{131}$I cytotoxic moiety, the dosage to the patient will typically start at a lower range of 10 mCi, and go up to 100, 300 or even 500 mCi. Stated otherwise, where the therapeutic agent is $^{131}$I, the dosage to the patient will typically be from 5,000 Rads to 100,000 Rads (preferably at least 13,000 Rads, or even at least 50,000 Rads). Doses for other radionuclides are typically selected so that the tumoricidal dose will be equivalent to the foregoing range for $^{131}$I. Similarly, chemotoxic or toxin protein doses may be scaled accordingly.

The antibody conjugate can be administered to the subject in a series of more than one administration. For therapeutic compositions, regular periodic administration (e.g., every 2-3 days) will sometimes be required, or may be desirable to reduce toxicity. For therapeutic compositions that will be utilized in repeated-dose regimens, antibody moieties that do not provoke HAMA or other immune responses are preferred.

The following description sets forth the general procedures involved in practicing the present invention. To the extent that specific materials are mentioned, it is merely for purposes of illustration and is not intended to limit the invention.

Example 1

Materials and Methods

Unless otherwise specified, general cloning procedures, such as those set forth in Sambrook et al., Molecular Cloning, supra or Ausubel et al. (eds) *Current Protocols in Molecular Biology*, John Wiley & Sons (2000) were used herein.

Reagents. Hoffman-La Roche (Nutley, N.J.) provided recombinant human (rh)IL-1α. Stem cell factor (rhSCF), rhIL-6, rhIL-11 and alkaline phosphatase (Alk Phos)-conjugated goat anti-rabbit IgG were purchased from R&D Systems (Minneapolis, Minn.). IL-1β and nerve growth factor (NGF) were purchased from Collaborative Research (Bedford, Mass.) and Amersham Life Science (Cleveland, Ohio) respectively. The following was purchased from Sigma (St Louis, Mo.): Isopropyl-D-Thioglactopyranoside (IPTG), SP, FICOLL HYPAQUE, lipopolysaccharide (LPS), Fibronectin-Fragment III-C (FN-IIIC), 12-0-tetradecanoylphorbol diester (TPA), dimethylsulfoxide (DMSO) and cytochemical staining kits for 2-naphthyl-acetate esterase and naphthol AS-D chloroacetate esterase. SP was dissolved in sterile distilled water and then immediately solubilized with nitrogen gas. The reconstituted SP was used within two days. The immunology department of Genetics Institute (Cambridge, Mass.) provided the human G-CSF and M-CSF. Rabbit anti-Id2 was purchased from Santa Cruz Biotechnology (Santa Cruz, Calif.). Rabbit anti-Histidine Affinity Tag (HAT) and HAT-affinity resin were purchased from Clontech (Palo Alto, Calif.). The HAT protein expression system (pHAT10) was also purchased from Clontech.

Cell Lines. With regard to primary human cell lines, bone marrow aspirates and peripheral blood from healthy human volunteers between the ages of 25 to 35 years, were used. Samples were obtained following informed consent. The bone marrow aspirates were used to prepare stromal cultures and to isolate BMNC. The peripheral blood was used to isolate mononuclear cells (PMNC). BMNC and PBMC were isolated by FICOLL-HYPAQUE density gradient.

K562, MCF12A, and MCF10 (non-tumorigenic); DU4475 (carcinoma); HCC70 and T-47D (low invasive) breast cells; and human melanoma cell line (SK-Mel) were purchased from American Type Culture Collection (ATCC, Manassas, Va.). The highly aggressive MDA-MDB-231 was obtained from Dr. Ian Whitehead, N.J. Medical School. CCL64 has been described (Rameshwar et al. (1994) supra). Cells were cultured as per ATCC instructions. HL-60 were cultured in RPMI 1640 (Sigma) containing 10% fetal calf serum, FCS (Hyclone Laboratories, Logan, Utah).

Bone Marrow Stromal Culture. Stromal cultures were prepared from bone marrow aspirates of healthy donors, ages 20 to 35 years. Cultures were prepared as described (Singh, et al. (2000) supra). Briefly, unfractionated cells from bone marrow aspirates were cultured at 33° C. and after day 3, RBC and granulocytes were removed by FICOLL-HYPAQUE density gradient. Cultures were maintained with weekly replacement of 50% medium until confluence.

cDNA Libraries. Three different cDNA libraries were screened with an NK-1 probe (Gerard et al. (1991) supra). One cDNA library, constructed from unstimulated pooled human bone marrow cells was purchased from Clontech (Palo Alto, Calif.). Two of the cDNA libraries were prepared with mRNA from IL-1α or SCF cytokine-stimulated bone marrow stroma as described (Rameshwar, et al. (2001) *Blood* 97:3025-303). Briefly, bone marrow stroma from more than 9 healthy donors were stimulated with 25 ng/ml IL-1α, or 10 ng/ml SCF and the pooled mRNA used to construct the cDNA library. Bone marrow donors were selected based on sex and ethnic diversity. Libraries were constructed using the ZAP EXPRESS cDNA GIGAPACK III Gold cloning kit (Stratagene, La Jolla, Calif.). XhoI and EcoRI adapters were ligated in pZAP, which resulted in ~$10^6$-$10^7$ pfu/ml. Each library was screened with $10^7$ pfu at $5\times10^4$ pfu/150 mm agar. Plaques were hybridized with a 0.65 kb fragment of NK-1 cDNA (Gerard et al. (1991) supra) using different hybridization and washing parameters. The insert from seven phagemid was amplified using T3/T7 primers and the PCR products were ligated into pCR2.1 (Invitrogen, Carlsbad, Calif.). The inserts were sequenced with the M13 forward and reverse primers, followed by five other sequencing with overlapping primers. Alignment of the overlapping DNA fragments indicated that the insert was equivalent to 2662 bp.

Cell Differentiation. Cell differentiation was performed with a myelomonocytic cell line, HL-60, or bone marrow mononuclear cells (BMNC). HL-60 cells were chemically differentiated with TPA and DMSO for monocytes and granulocytes respectively (Miura, et al. (2000) supra; Hegde, et al. (1999) Blood 94:1578-1589). BMNC were isolated from bone marrow aspirate of healthy donors using FICOLL HYPAQUE density gradient.

Further, BMNC cells were differentiated with M-CSF or G-CSF (500 U/ml for each) to monocytes and granulocytes, respectively. Undifferentiated cells were cultured in parallel with only media. Culture media were replaced at two-day intervals until cytochemical staining determined that >90% of the cells were differentiated. At this time, cell differentiation was terminated and the cells analyzed by northern analyses for Id2 and HGFIN mRNA, and by immunoblot for Id2 protein. For HL-60 cultures, cytochemical staining was performed after three days with 100-200 cells. Beginning at day 5, cells from cultures with BMNC were stained and daily thereafter. Neutrophil and monocyte staining were performed with kits specific for 2-naphthyl-acetate esterase and naphthol AS-D chloroacetate esterase, respectively.

Cell Stimulation. Peripheral blood mononuclear cells (PBMC) were resuspended in RPMI 1640 containing 2% FCS at $10^6$/ml. Cell suspension, 10 ml, was stimulated with 1 μg/ml of LPS. bone marrow stroma was stimulated in sera-free α-MEM (Sigma) with the following: 10 μg/ml SCF, 5 ng/ml IL-11, 5 U/ml IL-1β, 5 ng/ml IL-1β, 25 ng/ml NGF and ng/ml IL-6. Dose-response curves with slot blots for HGFIN mRNA determined the optimal concentration of each stimulus. During stromal cell stimulation, culture media were supplemented with insulin-transferring-selenium-A (Life Technologies, Grand Island, N.Y.). In both types of cells, controls included parallel cultures in similar media. At 8 hours and 16 hours, total RNA was extracted from each experimental point and control and then analyzed by northern analyses for HGFIN mRNA.

Northern Analysis. Northern analysis for steady state HGFIN mRNA was performed as described (Rameshwar, et al. (1997) J. Immunol. 158:3417-3424). Total RNA was extracted from the experimental cells and 10 μg from each was separated in 1.2% agarose. RNA was transferred to nylon membranes (S & S NYTRAN, Keene, N.H.) and then hybridized with [α-$^{32}$P]-dATP-labeled cDNA probes specific for HGFIN or Id2. Membranes were stripped and then reprobed with cDNA for 18S rRNA. Probes were randomly labeled with [α-$^{32}$P]-dATP, 3000 Ci/mM, (Dupont/NEN, Boston, Mass.) using the PRIME-IT II random primer kit (Stratagene). The membrane was placed in a PHOSPHOIMAGER cassette (Molecular Dynamics, Sunnyvale, Calif.) and then scanned at different times beginning at 6 hours to 24 hours on a PHOSPHOIMAGER (Molecular Dynamics). Negative results were not attributed to the lack of total RNA on the membrane since each was hybridized with a cDNA probe for 18S rRNA.

cDNA Probes. Transformed bacteria containing cDNA inserts for 18S rRNA and β-actin were purchased from ATCC. Id2 and HGFIN inserts were ligated in pCR2.1 (as described herein). Each of the cDNA probes used in this study was excised with EcoRI. The human Id2 cDNA was cloned by RT-PCR using 2 μg of total RNA obtained from differentiated HL-60 cells. Primers specific for Id2 were: 5'-CCG GTG CCA AGC GCA CCT-3' (sense, +208/+225; SEQ ID NO:3) and 5'-CGC TTA TTC AGC CAC ACA G-3' (antisense, +762/+780; SEQ ID NO:4). The following profile was used to amplify the Id2 fragment using 35 cycles: 95° C. for 30 seconds, annealing at 60° C. for 30 seconds, and extension at 72° C. for 1 minute. The sample was subjected to a final extension at 72° C. for 7 minutes. The PCR reactions containing the predicted fragments (508 bp) were purified using QIAQUICK Gel Extraction Kit (Qiagen, Valencia, Calif.). The purified DNA was subcloned into pCR2.1 and then sequenced using the M13 forward and reverse primers. Analyses of the sequence indicated that the selected fragment was >99% similar to the published clone for Id2 (Biggs, et al. (1992) supra).

Western Blots. Differentiated and undifferentiated BMNC were washed and resuspended in PBS, pH 7.4 containing 1 mM PMSF and 5 μM leupeptin (both protease inhibitors purchased from Sigma). Cell extracts were prepared by subjecting the cells to three cycles of freeze-thaw using an ethanol/dry ice bath and a 37° C. water bath. Extracts were centrifuged at 10,000 g for 10 minutes and then determined for total protein concentration using the BIO-RAD Protein Assay kit (BIO-RAD Laboratories, Hercules, Calif.). Extracts (15 Vig) were analyzed by western blot for Id2 protein as described (Rameshwar, et al. (2000) J. Immunol. 165:2271-2277). Briefly, proteins were separated on a gradient SDS-PAGE ranging from 10-20%. Proteins were transblotted to PVDF transfer membrane (NEN Life Sciences, Boston, Mass.) for 1 hour at 60 volts. Membranes were incubated with anti-Id2 (1/2000) at room temperature overnight followed by incubation with Alk Phos-conjugated anti-rabbit IgG for 2 hours at room temperature. Alk Phos activity was detected with BCIP/NBT substrate System (Kirkeguard & Perry Laboratories, Gaithersburg, Md.). The $M_r$ of the developed bands were compared with Rainbow colored markers (Amersham Life Science, Arlington Heights, Ill.).

Vectors and Reporter Gene Assay. pGL3-basic and Luciferase detection kit were purchased from PROMEGA (Madison, Wis.). β-galactosidase detection kit and pHyg were purchased from Clontech (Palo Alto, Calif.). pCR2.1 was purchased from Invitrogen (Carlsbad, Calif.). The p53 expression vectors and mutants are known in the art. The included pME18S-SN3 containing wild-type human p53, pME18S-SCX3 containing Val143Ala mutant human p53, and pPME18S (Shiio, et al. (1992)). The vectors are under the SRα promoter. The expression vectors encode both the N- and C-termini of p53 (Shiio et al. 1992).

Cloning of 5' Flanking Region of HGFIN Gene. Cloning of the 5' flanking region of HGFIN involved a 2-step cloning procedure to add Exon 1, with the translational start site omitted. The clone has been designated HGFIN-RM/2.0E. The first step used PCR with pooled human gDNA as template and Hot Start Ex Taq Polymerase with the following primers: 5'-GGT GCA GGG AAG GAA AAA AGA C-3' (SEQ ID NO:5) (sense) and 5'-TAG AGA CAT TCC ATG CTG AA-3' (SEQ ID NO:6) (antisense). The fragment was inserted into pCR2.1 and was designated HGFINRM/2.1.

Subsequently HGFIN-RM/2.0E was cloned with primers that included Exon 1 with omission of the translation start site. There primers were: 5'-CTC GAG GTG CAG GGA AGG AAA-3' (SEQ ID NO:7) (sense with XhoI linker) and 5'-AAG CTT TCC ATG CTG AAT TCC-3' (SEQ ID NO:8) (antisense with HindIII linker). The fragment was first ligated into pCR2.1 for sequencing. After the DNA sequencing verification, the insert was subcloned into pGL3-basic reporter vector within XhoI/HindIII sites.

Reporter Gene Assays. Reporter gene assays were performed as described (Qian et al. (2001) *J. Immunol.* 166: 2553-2561). Briefly, non-tumorigenic cells, at 60-80% confluence, were co-transfected with pGL3-HGFIN-2.0 or -HGFIN-2.0E and pβ-gal-control (0.2 μg each). Transfections with EFFECTENE (Qiagen) resulted in 60-80% efficiency as determined by labeling for β-gal. Controls were transfected with pGL3-6 basic pβ-gal. After 48 hours, cell extracts were quantitated for luciferase and β-galactosidase using kits from Promega and Clontech, respectively. The ratios of Luciferase/β-gal in cells transfected with vector alone were normalized to 1. Luciferase activities were presented per μg of total protein and the levels normalized with cells transfected with vector alone. Total protein in cell extracts was quantitated using a protein assay kit from BIO-RAD (Hercules, Calif.).

Stable HGFIN Knockdown and Expression. The method to construct HGFIN-specific siRNA into pPMSKH1 is disclosed herein. HGFIN siRNA was based on Accession AF322909 spanning +343/+361: 5'-CAT TTG CGG TGA ACC TGA T-3' (SEQ ID NO:9). Blast analyses using NCBI database determined no significant homology to any human gene. The 19 nucleotide (nt) sequence (sense) was placed in tandem with the loop structure followed by the antisense sequence of the upstream 19 nt sequence compliment, resulting in 64 nt. Control siRNA contained single nucleotide mutations within the gene-specific insert. Double-stranded DNA was ligated into pPMSKH1 at a molar ratio of 1:50 (vector to insert). Digestion with EcoRI and HindIII confirmed inserts of ~280 bp. Negative clones without inserts showed bands at ~220 bp. The insert was further verified by DNA sequencing. Stimulated (GM-CSF) bone marrow fibroblasts was used to induce HGFIN and verify the efficiency of siRNA in HGFIN knockdown.

HGFIN knockdown was carried out in MCF12A by co-transfection with pPMSKH1-HGFIN (wild-type or mutant) and pHyg. Stable transfectants were selected with hygromycin at μg/mL. HGFIN expression was studied by co-transfecting T47D with pFLAG-HGFIN and pHyg. Stable transfectants were selected with 150 μg/mL hygromycin. Selected cells were positive for FLAG by western blots with combination of whole cell and membrane extracts. The combinations of extracts were necessary since HGFIN is a membrane molecule.

Selection of Primary Breast Cancer Cells. Breast tissues were obtained at the initial diagnosis of patients with Stages IIIA or IIIB. At the time of surgery, patients were not subjected to chemotherapy or radiation. Patient 7 was obtained from Cooperative Human Tissue Network, University of Pennsylvania Medical Center (Philadelphia, Pa.). Variations in hormone status of patients are summarized in Table 1. Malignant cells within the surgical breast tissues were selected according to known methods.

TABLE 1

| Subjects | Age Range (Years) | ER | PR | HER2 | In situ Densities (Range) |
|---|---|---|---|---|---|
| Patients: 1-3 19-28 29-35 | 65-73 54-60 36-60 | − | − | − | <0.2-1.2 |
| Patients 4-7 8-10 | 55-60 60-64 | + | + | + | 1-1.5 |
| Patients: 11-18 36-50 | 70-82 56-65 | + | + | − | 0.5-1 |
| Benign Tissues | 35-60 | Not Done | Not Done | Not Done | 10 |

ER, Estrogen Receptor; PR, Progesterone Receptor; HER2, c-erbB-2.

In Situ Hybridization of HGFIN mRNA. Slides with surgical breast samples from benign and malignant subjects were obtained. In situ hybridization was performed with a cocktail of three antisense biotinylated oligonucleotides, 18 nt each, specific for the HGFIN mRNA. Briefly, the slides were de-waxed and then incubated with 30 μg/mL proteinase K for 1 hour at 37° C. Negative control slides were incubated with 100 μg/ml RNase for 30 minutes at 37° C. After this, slides were prehybridized with 200 ng/mL oligonucleotide cocktail, each with biotin conjugated at the 5' ends. The oligos were selected from the two ends, and middle regions of HGFIN cDNA, Accession AF322909: 5'-CCA CTT GAT GCC GCC AAA-3' (+111/+128) (SEQ ID NO:10); 5'-ATG GCA CCG GCC AAA GCC-3' (+496/+513) (SEQ ID NO:11); 5'-GCC TGT GGT ATG ATG TGC-3' (+2235/+2252) (SEQ ID NO:12). Sections were next incubated for 1 hour at room temperature with 1.25 μg/ml avidin-AP (Boehringer Mannheim Biochemicals). Control slides were incubated with a cocktail of sense oligomers. Slides were counterstained with Harris Modified Hematoxylin (Fisher Scientific, Springfield, N.J.) and then examined microscopically. Photomicrographs were imported into an image analysis program and analyzed to count the positive labelings. Labeling intensities <0.05 were considered negative. The densities of labeling from non-tumorigenic cells were normalized to 10.

Semi-quantitative RT-PCR. Total RNA was extracted from cells and 2 μg was reverse transcribed. cDNA, 200 ng, was subjected to PCR for HGFIN using primers designed from Accession AF322909, spanning +570/+681: 5'-AAC CTT TTC CTC ACC ACC C-3' (forward) (SEQ ID NO:13) and 5'-TTC ACA GAA ACT CTC ACT GAA C-3' (reverse) (SEQ ID NO:14). PCR reactions were normalized by amplifying the same sample of cDNA with primers specific for glyceraldehyde-3-phosphate dehydrogenase, GAPDH. The primers for GAPDH spanned +212/+809 (NM 002046): forward: 5'-CCA CCC ATG GCA AAT TCC ATG GCA-3' (SEQ ID NO:15); reverse: 5'-TCT AGA CGG CAG GTC AGG TCC ACC-3' (SEQ ID NO:16). PCR was done for 35 cycles for HGFIN and 30 cycles for GAPDH at 94° C. for 30 seconds, 55° C. for 30 seconds and 72° C. for 30 seconds with a final extension at 72° C. for 10 minutes. PCR reactions (10 μL) were separated by electrophoresis on 1.0% agarose containing ethidium bromide. Band sizes were compared with 1 kb DNA ladder (Invitrogen, Carlsbad, Calif.).

Methylcellulose Cultures. Clonogenic assays were performed by resuspending cells in 1.2% methylcellulose containing the respective culture media and monitoring colony formation. Assays were performed with cells seeded at 10²/ ml in 35 mm suspension dishes. Colonies with >20 cells were counted after 5-day incubation at 37° C.

Example 2

Purification of HGFIN from a Prokaryotic Expression Vector

PCR was used to amplify the coding region of HGFIN, +60/+1760 (GENBANK accession number AF322909). The following primer pairs were used in the PCR reaction: 5'-CGG GGT ACC ATG GAA TGT CTC TAC TA-3' (SEQ ID NO:17) (upstream with KpnI linker) and 5'-CCG GAA TTC TCG AAA TTT AAG AAA CT-3' (SEQ ID NO:18) (downstream with EcoRI linker). The HGFIN-specific sequences are underlined for both the upstream and downstream primers.

The amplified DNA fragment was cloned into pHAT10, hereafter referred as pHAT10-HGFIN. The vector was transformed into bacteria and HGFIN-HAT induced with IPTG. Induced bacterial cultures (20 ml) were sonicated in 2 ml of 100 mM Tris, pH 6.8, 4% SDS. After this, HGFIN was verified in the cell-free lysates by western blot analysis using 15 µg of total protein and rabbit anti-HAT. Details on the technique for western blot are described herein. The lysates that showed a band at the predicted size of ~66 kDa were further purified with the HAT-affinity resin (TALON Metal Affinity Resins, Clontech). The purification procedure followed manufacturer's protocol. Bacterial cultures, 20 ml, provided ~0.5 mg of total HGFIN protein. The purified proteins from different purification procedures were pooled and then verified by purified HGFIN by western blots.

Example 3

ProteinChip Analyses for HGFIN-SP Interaction

Before studying the interaction between SP and HGFIN, each protein was profiled by the Surface Enhanced Laser Desorption/Ionization (SELDI) ProteinChip Array technology (Ciphergen Biosystems Inc., Fremont, Calif.). Normal phase (NP1) arrays were used for profiling and preactivated surface arrays (PS1) for HGFIN-SP interaction. For profiling studies, 2 µg of purified HGFIN or 2 µg of SP were spotted directly onto the NP1 arrays. Prior to adding of the proteins, chips were pre-wet with PBS. Arrays were incubated at room temperature until the protein was absorbed, which took approximately 5 to 10 minutes. After this, 0.5 µl of sinapinic acid (SPA) (Ciphergen Biosystems), diluted at 1:50 in 50% acetonitrile and 0.5% trifluoroacetic acid was added to the arrays. Chips were immediately analyzed using linear, time-lag focusing laser desorption/ionization SELDI-time-of-flight mass spectrometer (Model PBS II). Accurate mass was determined by collecting approximately 150 averaged laser shots. The range of molecular mass that was used to calibrate the spectrometer ranged between 1000 Da to 100 kDa. The laser intensities ranged between 250 and 255.

The mass spectrometer data indicated that the SP was not degraded. HGFIN-SP interaction was studied by pre-treating the PS1 chips with 50% acetonitrile for 3 minutes. After this, the chips were incubated for 45 minutes with the following: 2.5 µg HGFIN (experimental sample), anti-Id2, an unrelated IgG regarding its ability to complex with SP and was therefore treated as a negative control, rabbit anti-SP (positive control) or 20 ng fibronectin, fragment III-C (positive control). The arrays were blocked for 25 minutes with 1 M ethanolamine and washed with PBS+0.5% TRITON-X (2×) and a final PBS wash step. After this the chips were washed with PBS+TRITON-X, PBS, rinsed with 5 mM HEPES and then dried. CHCA was applied and the non-covalently bound SP was detected with the SELDI-Time of Flight Mass spectrometer as described for the profiling studies for HGFIN.

Since the HGFIN clone was retrieved through screening of cDNA libraries with an NK-1-specific probe the natural, high affinity ligand for NK-1 could interact with HGFIN. The coding region of HGFIN was cloned and the protein was prepared purified with a prokaryotic vector under the control of IPTG and the histidine tag of 19 amino acid residues. Western blots with anti-His and proteomics studies verified the purity of HGFIN consisting of the histidine tag at the predicted molecular mass of ~66 kDa.

Protein-protein interactions were performed with the PS1 protein chip since this chip was determined to covalently bind HGFIN. SP was added to the chip and then detected with the SELDI system. The results showed a single peak at ~13000 Da indicating that the interaction between SP and HGFIN was non-covalent. Similar studies with HGFIN expressed in a eukaryotic vector in the absence of the HAT tag showed similar results, indicating that the tag protein was not responsible for the interaction between SP and HGFIN.

Fibronectin has been reported to bind SP. Therefore, this property of fibronectin was used as a positive control for SP interaction on the SELDI system. As expected, PS1 chips that were covalently coated with FN-IIIC and then incubated with SP showed a single peak at ~13000 Da. Similar results were shown with another positive control: rabbit anti-SP (co-valently bound) and SP. No peak was detected in two negative controls, which consisted of bovine serum albumin or an unrelated antibody (anti-Id2) covalently bound to the surface of PS1.

Computational studies were next used to devise a 3-D model to understand the interaction between HGFIN and SP. The 3-D structure of the PKD region from HGFIN was generated based on the structure of the PKD region on the protein database. The structure of SP is known in the art. The PKD region was selected since the putative spatial arrangement in the extracellular portion of HGFIN (FIG. 2) would allow contact with SP. Unlike a binding pocket in NK-1 for SP, there was no obvious pocket for PKD. However, the electrostatic differences between SP and PKD could allow for one to model protein-protein interactions that might explain how the PKD regions of HGFIN might interact non-covalently with SP.

Example 4

Expression of HGFIN in Differentiated Immune/Hematopoietic Cells

Since the HGFIN cDNA was isolated from bone marrow cell subsets, bone marrow and PB mononuclear cells were screened using northern analyses to study the expression of HGFIN. BMNC represents proliferating progenitors and PBMC represents differentiated cells that could be derived from the bone marrow progenitors. The results showed no detectable HGFIN mRNA in BMNC from five different healthy donors, while HGFIN expression was detectable in PBMC from the same donors. Since HGFIN was detected in cells that represent a predominant population of differentiated immune cells (PBMC), the results indicated that HGFIN may be associated with cell differentiation. To further investigate a role for HGFIN in cell differentiation, BMNC were stimulated with M-CSF or G-CSF. After the cells were >90% differentiated to monocytes and neutrophils, cells were analyzed for the expression of HGFIN mRNA by northern analyses. The results indicate that differentiation of BMNC to monocytes and neutrophils correlates with detectable HGFIN mRNA.

To verify that the expression of HGFIN was not due to activation by the two cytokines, northern analyses were performed with BMNC cultured with M-CSF or G-CSF and then analyzed for HGFIN mRNA before the cells were differentiated. The results showed no detectable HGFIN mRNA, similar to unstimulated BMNC. Together, the data indicated that HGFIN is preferentially expressed in differentiated immune and hematopoietic cells.

As stated, Id2 is an inhibitor of cell differentiation (Biggs, et al. (1992) supra). Thus, Id2 would be expected to be detectable in BMNC cells and then down-regulated after the cells differentiate. Since the HGFIN gene appears to be associated with cell differentiation, studies were performed to determine its association with Id2. The reason for choosing this particular transcription factor among the Id family is because Id2 mediates terminal differentiation in progenitors with cell cycle arrest during granulopoiesis but its expression is down-regulated after the cells differentiate (Cooper & Newburger (1998) *J. Cell. Biochem.* 71:277-285; Ishiguro, et al. (1996) *Blood* 87:5225-5231). Furthermore, Id-2 expression is expressed in HL-60 cells, a granulocytic progenitor cell line (Norton, et al. (1998) *Trends Cell Biol.* 8:58-65).

Northern blots were performed in four experiments, each with a different donor. The results showed that Id2 was undetectable in differentiated BMNC. However in undifferentiated BMNC (cultured in media alone), Id2 mRNA was detected in each of the four bone marrow donors. In BMNC differentiated with M-CSF or G-CSF, the band for Id2 protein was very light to undetectable. The data presented in this section indicate that HGFIN is expressed in differentiated bone marrow cells and that its expression correlates with down-regulation of Id2, the transcription factor that inhibits cell differentiation.

Whole cell extracts from the same bone marrow donor were studied for Id2 protein by western blot analysis and the results showed a single band at 15 KDa in undifferentiated/BMNC and no detectable band in differentiated cells. The data presented in this section indicate that HGFIN is expressed in differentiated bone marrow cells and that its expression correlates with down-regulation of Id2, the transcription factor that inhibits cell differentiation.

HGFIN mRNA was studied in differentiated and undifferentiated HL-60 cells to determine if the expression of this gene was limited to normal bone marrow progenitors. HL-60 cells were differentiated with chemical agents, TPA or DMSO for monocytes or granulocytes, respectively. Similar to normal progenitors, HGFIN mRNA was detected in differentiated HL-60. HGFIN mRNA was undetectable in undifferentiated cells. The results show that HGFIN is expressed after differentiation of the myelomonocytic leukemic cell line, HL-60 to granulocytes and monocytes.

As differentiated immune cells express HGFIN, studies were performed to determining if HGFIN was also expressed when these differentiated cells were activated. This question was addressed by stimulating PBMC with LPS for 8 and 16 hours and determining the levels of steady state HGFIN mRNA by northern analysis. Studies with PBMC from three different healthy donors A, B and C showed that LPS stimulation down-regulated HGFIN expression at 16 hours. There was no difference at 8 hours. Consistent with HGFIN expression in PBMC, HGFIN mRNA was detected in the unstimulated PBMC. The data indicate that the expression of HGFIN in unstimulated, differentiated PBMC was down-regulated following cell activation by a mitogen.

The mesenchymal/stromal cells of the bone marrow produce most of the necessary soluble regulators that modulate bone marrow organ functions (Muller-Sieburg & Deryugina (1995) supra). Since HGFIN expression was altered in activated PBMC, the next set of studies examined the role of HGFIN in activated bone marrow stroma. The following stimulators were used: cytokines, SCF, IL-11, IL-1($\alpha$, $\beta$) and IL-6 and a neurotrophic factor, NGF. The results of three studies indicated that HGFIN was induced in each of the stimulated stromal cells. Densitometric scans were normalized with 18S rRNA and the fold (mean±SD) increase over unstimulated stroma was determined. The steady state levels of HGFIN mRNA in cultures stimulated with SCF, IL-11, IL-1$\alpha$/$\beta$ or IL-6 were comparable. However, together, the levels of HGFIN mRNA in the cytokine-stimulated cultures were much less than in stroma stimulated with NGF.

To determine if HGFIN is expressed in tissues other than bone marrow and immune cells, a northern blot was performed with a membrane from a commercial source, which has poly A from different tissues, Human MTN blot (Clontech, Palo Alto, Calif.). Except for mRNA isolated from the brain, the results showed a single band from the other tissues. The bands from the lung, liver, and skeletal muscle were less intense than the lanes from the other HGFIN expressing tissues (heart, placenta, kidney, pancreas). The reduced band intensities could not be due to differences in the mRNA loaded per lane since the MTN blots were equally intense for P-actin mRNA. The similarity in P-actin levels was consistent with the manufacturer's product information.

HGFIN has also been discovered in breast cancer cells. HGFIN is homologous to the nmb cDNA that was isolated in melanoma (Weterman, et al. (1995) supra). The next set of studies screened cancer cell lines from human melanoma and breast cancer (T-47D and DU4475). Comparison was made with a normal mammary epithelial cell line (MCF-12A). Except for T-47D, each cell line tested showed single bands at the predicted size of 2.4 kb. A double band was shown for T-47D, one at 2.4 kb and the other slightly bigger. The validity of the double band in the T-47D cell line was verified in three separate experiments using cell lines from different passages. These results showed that HGFIN expression is not limited to bone marrow and immune cells.

Paraffin sections of breast biopsies were also analyzed for HGFIN mRNA by in situ hybridization with a cocktail of biotin-conjugated oligonucleotides. Malignant breast cells from primary sources were also analyzed for HGFIN mRNA. RT-PCR with selected primary breast cancer cells showed a light band for Stage 0 breast cancer patient (P0) and undetectable bands for breast cancer cells selected from Stage III patients (P1 and P38).

In situ hybridization for HGFIN mRNA analyzed fifty breast biopsies from patients at various stages of breast cancer and benign tissues. Representative labelings showed dense labels for benign sections, but undetectable labeling for malignant tissue. In total, high HGFIN expression was observed in non-tumorigenic breast cells, but reduced expression in malignant breast cancer cells.

Example 5

Role of HGFIN

The present invention sets forth the association of the HGFIN gene with hematopoietic cell differentiation. Since the HGFIN gene is expressed in other tissues, it is likely that this gene may be involved in the differentiation of cells in other tissues. Since melanoma and breast cancer cell lines express HGFIN, regulation of HGFIN expression in melanoma and breast cancer can be used to modulate cancer proliferation. Further, since both NK-1 and HGFIN bind SP, treatment of cancer cells that express HGFIN, including breast cancer, can involve targeting both NK-1 and HGFIN. As a result, regulating ligands which bind to NK-1 and/or HGFIN may have implications in breast cancer treatment and treatments of cancerous cells that express both NK-1 and HGFIN.

The down-regulation of HGFIN in immune cells stimulated with LPS was observed. LPS is a B-cell mitogen and despite terminal cell differentiation of B-cells, mitogens could mediate the polyclonal expansion of B-cells. The present inventors studied HGFIN expression in cells from a 'quiescent' differentiating state to the reversion into proliferating cells. Results suggest that differentiating cells may be prevented from proliferating in the event that HGFIN expression cannot be down-regulated.

Also, over-expression of HGFIN in proliferating cells such as bone marrow progenitors may be polarized into terminal differentiation. This mechanism is applicable to leukemia and lymphoma, where the cells are at a checkpoint of proliferation. Further, the HGFIN gene could be involved in differentiation in other tissues where it is overexpressed as well. HL-60 was studied since it is a myelomonocytic leukemic cell line. These findings, as well as the data, which showed differences in HGFIN expression from studies with differentiated and predominantly proliferating BMNC are important in showing how HGFIN could be intervened in leukemia and perhaps lymphoma. As discussed above, specific antibodies to HGFIN (prepared in accordance with the methods described herein) and studies on the spatial arrangement of HGFIN within a cell will further lead to a more comprehensive understanding of the biology of this gene and how it can better be used to treat blood related diseases.

The interaction between SP and the PKD region of HGFIN is important in the development of immune cells and erythrocytes in the bone marrow since SP is a hematopoietic regulator (Rameshwar (1997) *Clin. Immunol. Immunopath.* 85:129-133). Proteomic analyses shows an interaction between SP and the PKD region of HGFIN. This interaction may be important in regulating other functions, given SP's dual role as a proinflammatory peptide and as a hemapoietic regulator. For instance, SP may induce cytokines and other hematopoietic relevant factors in bone marrow cell subsets and immune cells. Another relevance for this interaction is bone morphogenesis since SP is involved in bone metabolism (Adamus, et al. (2001) *J. Cell. Biochem.* 81:499-506).

Furthermore, since SP binds to NK-1 (Rameshwar (1997) supra; Krause, et al. (1992) supra), which is the cDNA that was used to isolate the HGFIN clone during screening of the libraries, and since NK-1 is associated with several clinical disorders and is a target for drug development (Rupniak (2000) *Tachykinins* 2000:2a), molecules such as HGFIN with potential binding of SP could confound the treatments with drugs that target NK-1. It has been shown that SP can complex to fibronectin. The property of SP to bind proteins that share structural homology to its high affinity receptor, NK-1 could confound the biology of NK-1, which is associated with several clinical disorders and a target for drug development.

During targeting of NK-1, the ligand, SP, could bind to other molecules such as HGFIN and fibronectin, part of the bone marrow extracellular matrix proteins. In these cases, SP, which preferentially binds to NK-1 would be available to HGFIN at 'abnormal' levels and might mediate other functions through its interaction with HGFIN and other molecules. The analysis disclosed herein indicates how such an interaction is possible since similar 3-D structure was observed for fibronectin, which shared a homologous region with NK-1 (Rameshwar, et al. (2001) supra).

Figure 2:
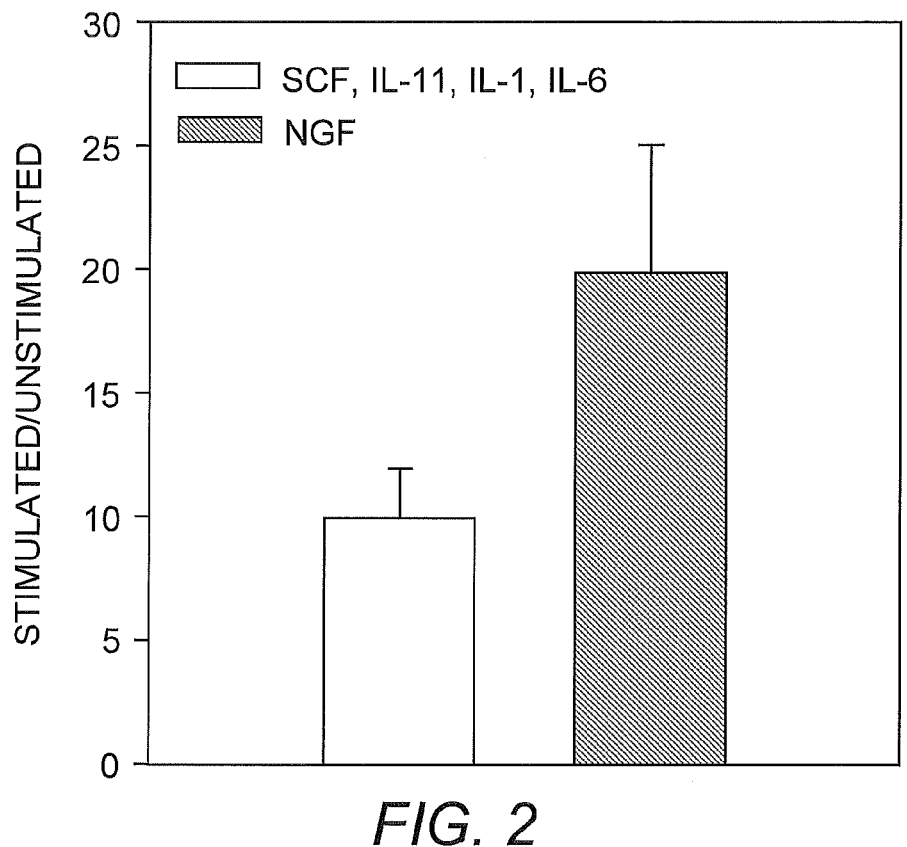
FIG. 2 shows the expression of HGFIN in bone marrow stroma upon stimulation with various hematopoietic relevant cytokines. The results are from three experiments, each with a different healthy donor. Band intensities were normalized with 18S rRNA and the induction over unstimulated cells is shown.

HGFIN induction in bone marrow stromal cells of healthy subjects was different than in the differentiated hematopoietic cells. While HGFIN mRNA is undetectable in unstimulated stroma, it is induced by cytokines (FIG. 2). A compelling relevance for these findings is based on the importance of the bone marrow stroma to regulate the proliferation and differentiation of hematopoietic stem and progenitor cells (Muller-Sieburg & Deryugina (1995) supra). In contrast to stromal cells, the expression of HGFIN in differentiated immune cells was blunted following cell stimulation. Together, these results indicate that HGFIN is important at two levels of the hematopoietic hierarchy: at the top where the stromal cells have major roles in regulating the hematopoietic stem cells (Muller-Sieburg & Deryugina (1995) supra) and at the terminal end where the cells are fully differentiated and are ready to exit the bone marrow into the circulation and to the secondary lymphoid organs. The fact that HGFIN was down-regulated when Id2 was upregulated and vice versa, indicates that the basic helix-loop-helix family of transcription factors (Massari & Murre (2000) *Mol. Cell. Biol.* 20:429-440) may be important in the regulation of HGFIN.

Example 6

Breast Cancer Metastasis to the Bone Marrow

Breast cancer metastasis can involve the processes of breast cancer cell entry in the bone marrow, and through seeding of the breast cancer cells in areas of stromal cells. A model was developed to represent the movement of breast cancer cells across endothelial cells, facilitated by MSC, by establishing methods to obtain pure cultures of primary MSC which were immunologically and phenotypically characterized (Randall & Weissman (1998) supra). A model with a Boyden chamber to study an example of mesenchymal stem cells as facilitators to breast cancer cells was used.

The Boyden chamber with an 8 micron insert was used to model breast cancer cells entering the bone marrow. Layer MSC were added in DMEM with sera. At semi-confluence, human umbilical vein endothelial cells (HUVEC) were added in sera-free DMEM. Tight junction of HUVEC was rapidly attained with the MSC providing the necessary growth and survival supplements. Thirty to one hundred breast cancer cells were added in sera-free media. After an hour, transmigration of the cells was examined. The data showed that MSC have significant roles in facilitation of breast cancer cells across the endothelial barrier (See Table 2).

TABLE 2

| Breast Cells | Layers | | | | | |
|---|---|---|---|---|---|---|
| | HUVEC | MSC | BC | BC MSC | BC HUVEC | BC HUVEC MSC |
| Non-trans-formed* | None | None | <1% | <1% | None | None |
| DU4475 | None | None | <1% | 80 ± 12% | 5 ± 2 | 100% |
| T-47D | None | None | <1% | 95 ± 11% | 3 ± 1 | 100% |
| BT-474 | None | None | <1% | 82 ± 10% | 3 ± 2 | 100% |

*MCF12A, MCF10 cells.

Numbers represent percent migration of breast cells from the inner to the outer wells (n=3; ±SD).

Initial experiments to suppress PPT-1 in breast cancer cells with antisense oligos showed that the PPT-1 gene was required for breast cancer cell integration among stromal cells. Hence, siRNA-pPMSKH1 was constructed similar to another previously described (Brummelkamp et al. (2002) Science 296:550), with the goal of inserting specific sequences to suppress any gene.

The link between HGFIN and breast cancer metastasis was explored next to show the role of HGFIN as a tumor suppressor gene. The fact that HGFIN is linked to hematopoietic cell differentiation with concomitant blunting of Id2 expression (Bandari et al. (2003) supra) indicated that HGFIN could be important in keeping cells in $G_0/G_1$ phase of the cell cycle. Indeed, analysis of the 2 kb region upstream of HGFIN (Genbank Accession No. AF549408) revealed eight consensus sequences for p53.

Subsequently, reporter analysis using luciferase activity was conducted on a 2 kb and a 1.5 kb DNA fragment upstream of the HGFIN gene in breast cancer cells lines and the same cell lines that are PPT-1 deficient (by siRNA). The results of this analysis indicated that HGFIN interacts with PPT-1 peptide and acts as a decoy membrane protein. HGFIN may be the negative feedback for PPT-1 peptides/NK receptors. Confirmed by northern blot analyses, these studies show high expression of HGFIN in non-transformed breast cells and significantly less expression in breast cancer cells. Computer analyses showed SNPs at several potential sites of C/T and one A/G.

Figure 3A:
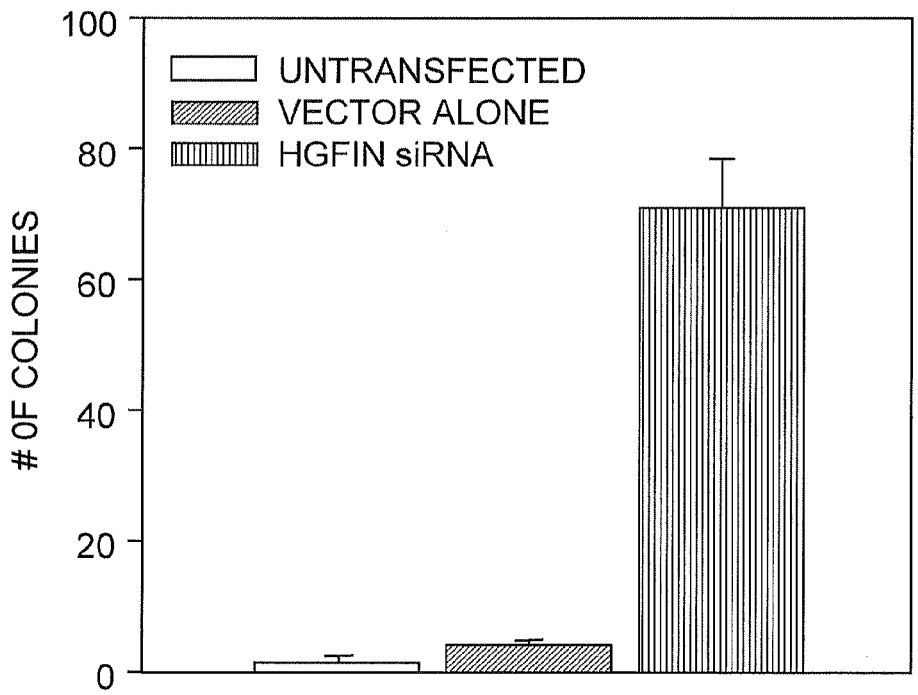
FIG. 3A shows the total number of colonies in methylcellulose cultures plates with 100 cells/dish. The results are presented as mean±SD, n=5.

Malignant cells showed undetectable to reduced expression of HGFIN, indicating a malignant phenotype in cells with reduced HGFIN expression. It was therefore determined whether HGFIN knockdown in non-tumorigenic MCF12A could confer a transformed phenotype. Knockdown cells were studied for contact-independent growth in methylcellulose matrix and in growth curve. Control cells were untransfected, stably transfected with vector alone (pPMSKH1) or mutant HGFIN siRNA. Representative colonies for untransfected or vector transfectants showed no colony by day 5. HGFIN mutant siRNA showed similar findings. HGFIN knockdown MCF12A resulted in large colonies, indicating cell transformation. The total number of colonies with >20 cells were counted and presented as the mean±SD, n=4. The results showed increased colonies in HGFIN siRNA cells as compared to untransfected and vector transfectants (FIG. 3A).

Figure 3B:
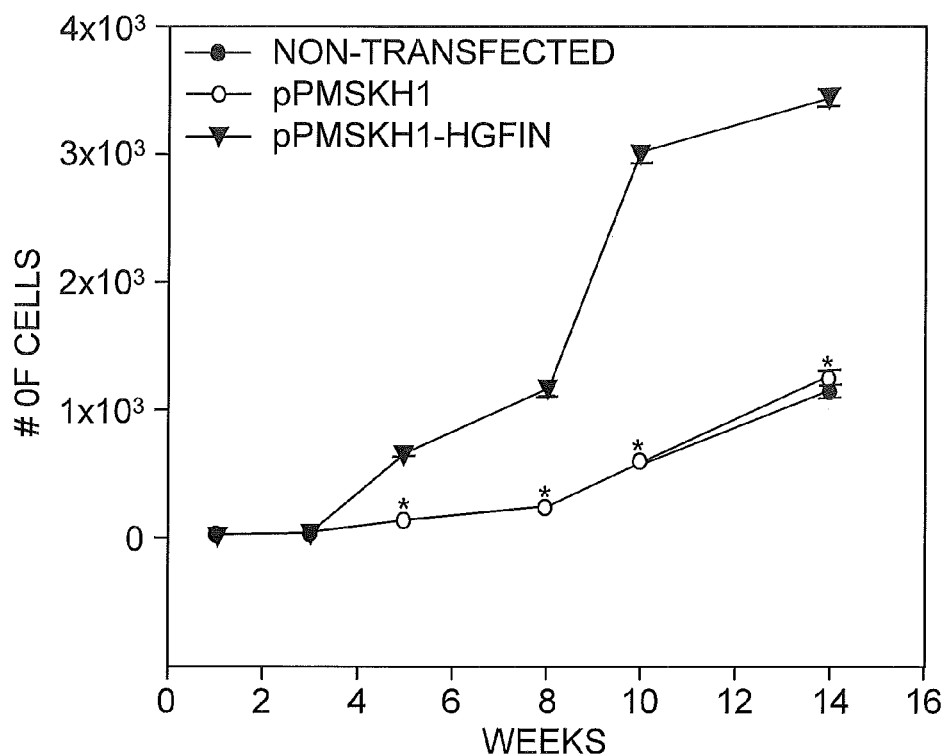
FIG. 3B shows growth curve analyses with MCF-12A, untransfected or stably transfected with vector alone or knockdown for HGFIN. Cells were counted at weekly intervals and the results presented as mean±SD of five different experiments. * $p<0.05$ vs. culture with pPMSKH1-HGFIN siRNA.

Transformation is generally associated with increased cell growth. Growth curves were therefore generated for HGFIN knockdown MCF12A cells beginning with 100 cells/dish. The growth curve for vector-transfected MCF12A was similar to untransfected cells (FIG. 3B) and mutant HGFIN siRNA transfectants. In contrast, HGFIN knockdown MCF12A showed increased cell growth (FIG. 3B). The increases were significant (p<0.05) as compared to the other experimental points beginning at week 4.

Figure 4:
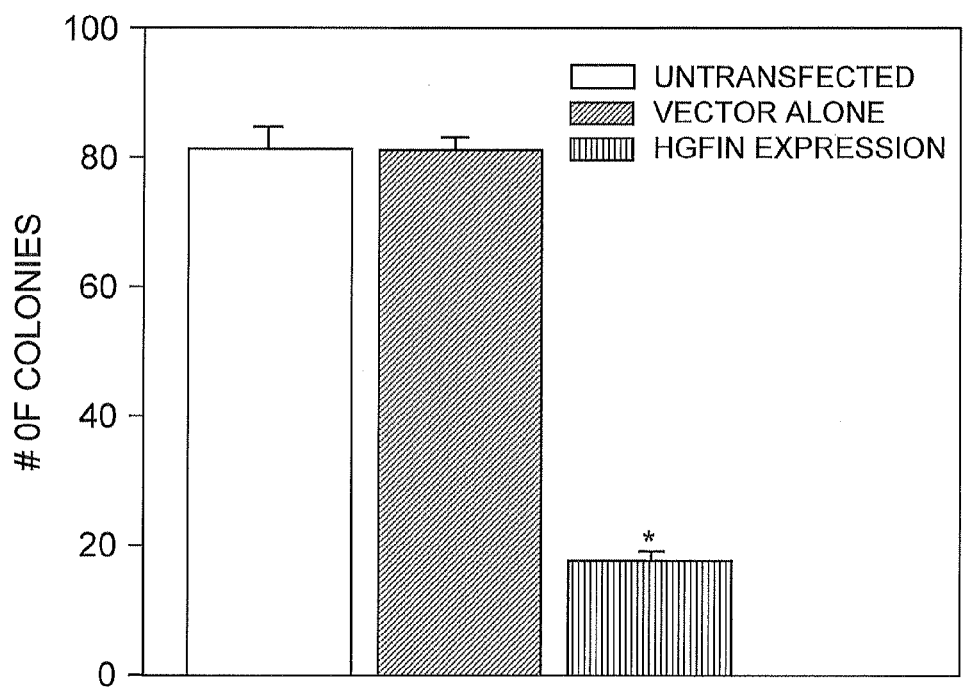
FIG. 4 shows that HGFIN imparts contact-dependent growth of T47D. Transfected or untransfected T47D cells were analyzed in 5-day clonogenic assays at 100 cells/35 mm2 dishes. The total number of colonies are presented as mean±SD, n=5. * $p<0.05$ vs. untransfected and vector transfectants.
Figure 5:
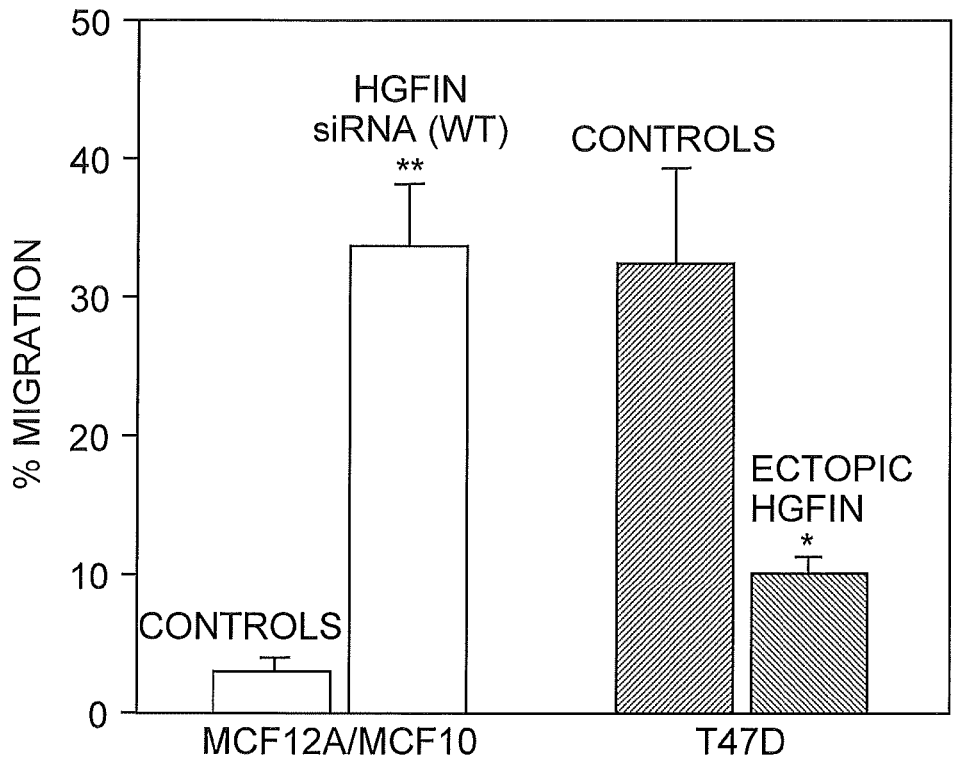
FIG. 5 shows the role of HGFIN in cell migration. HGFIN knockdown MCF12A and T47D with ectopic expression of HGFIN were studied in cell migration assays. Controls included MCF12A were done with untransfected cells, vector transfectants or HGFIN mutant siRNA transfectants. Controls for T47D were done with untransfected cells or vector transfectants. All values for controls were presented in the same bars. The data are presented as mean±SD, n=5.

Since HGFIN knockdown led to increased growth of MCF12A and loss of contact-dependent growth (FIG. 3), it was next determined if ectopic expression of HGFIN in a low metastatic cell line could lead to reduced clonogenicity. T47D cells were stably transfected with pFLAG-HGFIN and their growth in methylcellulose cultures was analyzed. After 5 days, colonies were detected for untransfected cells and vector transfectants. No colony was observed for HGFIN-expressing T47D. The cells did not undergo cell death as determined by trypan blue exclusion. The total number of colonies in cultures plated with 100 cells/dish was determined, wherein a significant (p<0.05) decrease in colonies for HGFIN expressing cells was observed as compared to untransfected T47D and vector transfectants (FIG. 4). In summary, these data show a loss of contact-independent growth in T47D cells, ectopically expressed for HGFIN.

Since HGFIN confers reduced growth rate, and adherent-dependent growth (FIGS. 3 and 4), it was subsequently determined whether these observations correlated with the cell migration. Comparisons were done with MCF12A and T47D cells. MCF12A was stably knockdown for HGFIN and T47D was stably expressed with ectopic pFLAG-HGFIN. There was a significant (p<0.05) increase in HGFIN knockdown MCF12A as compared to untransfected and mutant siRNA transfectants (FIG. 4). In contrast, ectopic-expression of HGFIN in T47D showed significantly (p<0.05) reduced migration as compared to untransfected and vector transfectants (FIG. 4). In summary, HGFIN expression reduced cell migration of T47D and MCF12A.

Figure 6A:
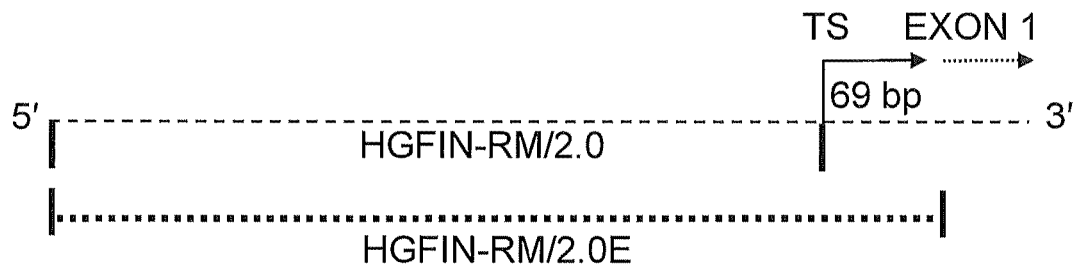
FIG. 6A is a cartoon depicting the upstream region of HGFIN. TS: transcription start site.
Figure 6B:
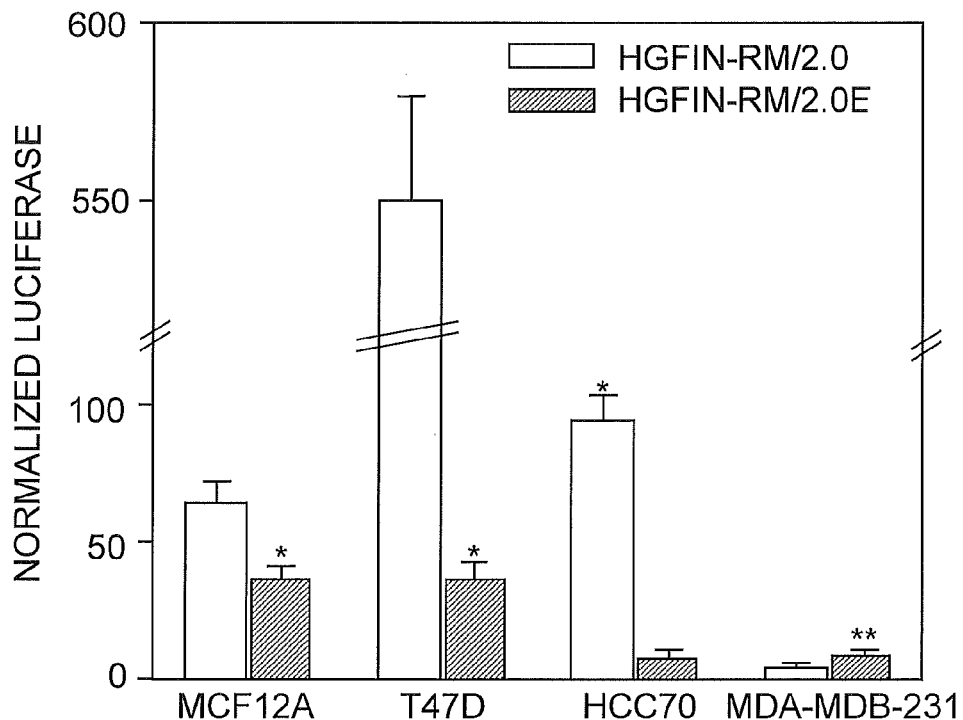
FIG. 6B shows non-tumorigenic (MCF12A) and tumorigenic (T47D, HCC70, MDA-MDB-231) cells cotransfected with pGL3-HGFIN-RM/2.0 or -RM/2.0E and pGal. Luciferase activity was normalized with β-galactosidase activity. The data are presented as mean±SD, n=6. * $p<0.05$ vs. HGFIN-RM/2.0 ** $p>0.05$ vs. HGFIN-RM/2.0E, MDA-MDB-231

Studies with a 2.0 kb fragment upstream of Exon 1 were also conducted. Exon 1 is an untranslated region of HGFIN (FIG. 6A). This study examined the role of Exon 1 in non-tumorigenic cells to provide insight into the dysfunctional expression of HGFIN in malignant cells. A reporter gene system with Exon 1 (minus the translational start site; pHGFIN-RM/2.0E) was employed to study expression in MCF12A and three breast cancer cell lines. The studies were compared with a construct in which Exon 1 was omitted (HGFIN-RM/2.0). HGFIN-RM/2.0E showed significant (p<0.05) decrease in luciferase activities in MCF12A, T47D and HCC70 (FIG. 6B). There was no significant (p>0.05) difference between the HGFIN-RM/2.0 and -RM/2.0E in the highly metastatic MDAMDB-231 cell line. In addition, luciferase activities were markedly reduced in MDA-MDB-231 as compared to the other cell lines. This difference was not due to reduced transfection efficiency since co-transfection with pGal showed β-galactosidase activity similar to the other cell lines.

Figure 6C:
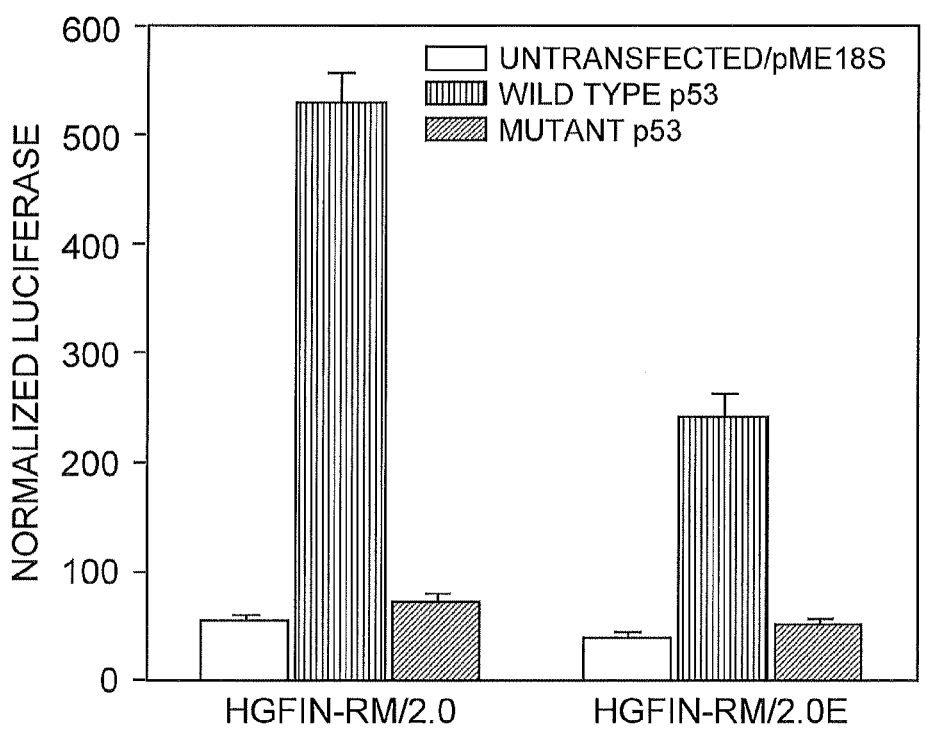
FIG. 6C shows T47D cells co-transfected with HGFIN-RM/2.0 or HGFIN-RM/2.0E and with wild-type or mutant p53 expression vectors. Controls were transfected with vector alone. Luciferase activities were determined after 16 hours transfection and are presented as mean±SD, n=6.

Computer analyses have identified a consensus sequence for p53 in Exon 1 (FIG. 6A). It was therefore determined if high levels of wild-type p53 can reverse the repressive effect of Exon 1. This question was addressed with a cell line that expresses low levels of p53, CCL64. Cells were co-transfected with pGL3-HGFIN-RM/2.0 or -RM/2.0E and/or the following: pME18S-SN3 wild type p53, pME18S-SCX3 mutant and pPME18S vector alone. Despite ectopic wild-type p53, Exon 1 still retained its inhibitory property, although less (FIG. 6C). In summary, these data demonstrate a role for wild-type p53 in reversing the suppressive effect of Exon 1 in HGFIN activity.

Figure 7A:
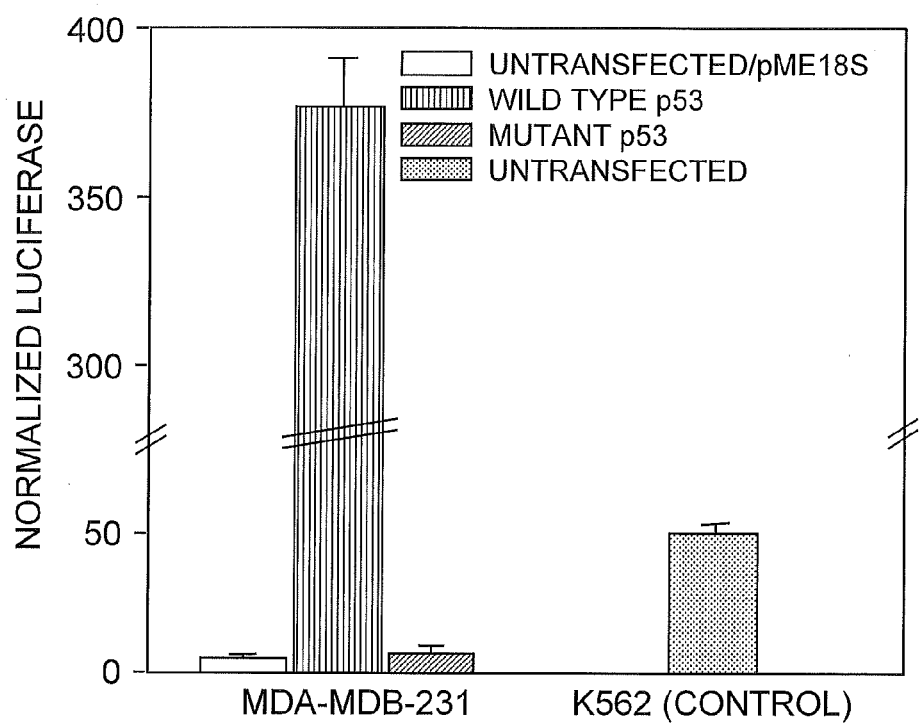
FIG. 7A shows MDA-MDB-231 cotransfected with pLuc and/or pME18S-SCX3 expression p53, mutant or vector alone. K562 transfected with pLuc served as control. The results are presented as mean±SD, n=5.
Figure 7B:
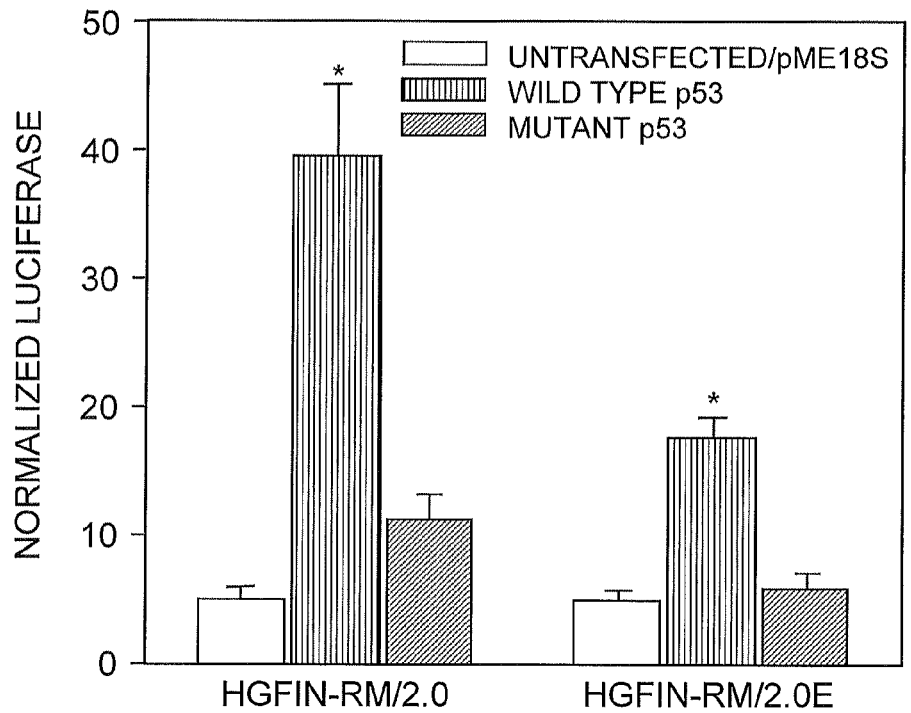
FIG. 7B shows MDA-MDB-231 coexpressed with HGFIN-RM/2.0 or HGFIN-RM/2.0E and/or p53 expression vector, pME18S-SCX3. Controls were co-transfected with p53 mutants or vector alone. The results were normalized with β-galactosidase and are presented as mean±SD, n=6. * $p<0.05$ vs. vector/untransfected and mutant p53.

MDA-MDB-231 expresses mutant p53, therefore, it was verified whether the MDAMDB-231 also expresses functionally mutated p53. This was addressed by transfecting pLuc into MDA-MDB-231 with or without ectopic expression of p53 and determining luciferase activity. Cells were co-transfected with pLuc and/or pME18S-SN3 wild-type p53, pME18SSCX3 mutant and pPME18S vector alone. Control studies used K562 cells stimulated with 10 nM neurokinin-A that can activate p53. The results showed a significant (p<0.05) increase in luciferase activity in transfectants with wild-type p53 as compared to vector alone or mutant p53 (FIG. 7A). Control K562 verified the experimental variables associated with pLuc (FIG. 7A). MDA-MDB-231 cells were co-transfected with p53 and pGL3-HGFIN-RM/2.0 or -2.0E. In the case of HGFIN-2.0, p53 expression led to increased luciferase by 4-fold as compared to p53 mutant transfectants (FIG. 7B). Similar increase was not observed for HGFIN- 2.0E. Therefore, reduced HGFIN in the highly aggressive MDA-MDB-231 could be partly explained by wild-type p53.

Example 7

Isolation of Cancer Stem Cells

This experiment isolates clones of cells with functions consistent for cancer stem cells. At division, the stem cell has a self-renewal property, meaning that it will form one of itself. Cancer stem cells express mdr genes, similar to other subsets of cancer cells. The cancer stem cells are likely more efficient at pumping out molecules. The cancer stem cells resist cell death by chemotherapeutic agents. The doubling time of the cancer stem cells is significantly longer compared to cancer progenitors. During early integration of cancer stem cells, they adapt a transitional function of mesenchymal/stroma-type cells and produce collagen I and EDa fibronectin (Brekken & Sage (2001) supra). Although these cells retain the intrinsic property of stem cells, they nonetheless remain functionally 'ignorant/harmless' and do not cause immediate bone invasion, or alter bone marrow functions. During metastasis from the marrow to tertiary sites, the 'quiescent' cancer stem cells revert to functions consistent with their original property of a stem cell and commit to rapidly dividing cancer progenitors, which are capable of aggressive invasion to bone and other distant tissues.

In the selection of clones, 10-12 different breast cancer cell lines are screened. Breast cancer cells are cultured in the presence of each or combinations of the anti-cancer agents 5-FU, Methothrexate, and Cytarabine. Cultures are initiated using the lowest dose and then increasing the dose, similar to selection strategies for stable transfectants with neomycin or hygromycin. Cells are passaged at least 5 times in high concentrations of anti-cancer drugs. The results of this experiment are that few cells survive, but those that do are expanded into clones for the 2nd round of screening, which comprises a two-step limiting dilution Clones are expanded in the appropriate culture media and frozen as a backup in case of experimental errors. Each clone is then subjected to a second round of selection by limiting dilution in 96-well plates (duplicate cultures). Plate 1 is treated with one or combinations of anti-cancer agents. Any difficulty in expanding the cells is remedied with feeder cells. Clones are designated as resistant, moderately sensitive or highly sensitive to the anti-cancer agents. These designations are based on the time for cell death of clones. The clones are frozen. Growth curves are performed on each subset of clones. The growth curves and the doubling times for the 3 categories of clones is used as the basis for further studies to group them as slowly-growing, moderately-growing, or rapidly-growing cells.

To confirm this approach, clones of cancer stem cells from 10 or 12 different breast cancer cell lines were selected, which resulted in 10-15 clones total. Breast cancer cells were subjected to rounds of exposure to 5-fluorouracil (5-FU), methotrexate, and cytarabine. Then, methods were employed to elucidate the mechanisms by which the cancer stem cells were stimulated to form cancer progenitors. Studies indicated that cancer stem cells were resistant to 5-FU and to 2000 R γ-irradiation. Cancer stem cells also preferred cells that remained within bone marrow stromal cells for more than 4 months. Furthermore, when heterogeneous breast cancer cell lines were placed in culture with stroma, a subset with low frequency became part of the stroma and the larger subset underwent cell death. The surviving subset was resistant to 5-FU treatment.

Example 8

Characterization of Slow-Growing and/or Drug Resistant Clones Via Flow Cytometry Another experiment of the present invention characterizes slow-growing and/or drug resistant clones by flow cytometry, which determines the degree that cells from different clones can pump dye (either Rhodamine 123 or Hoechst as used experimentally). The cancer stem cells are likely more efficient than cancer progenitors to pump dye out of cells. The size and scatter pattern of the different clones are examined to determine whether the slow-growing clones represent side population (S-Pop) cells and whether the progenitor cells larger so that they would be identified at a particular region in the scattergram. A subset of the study population is collected by cell sorting based on size and/or rhodamine uptake. Drug resistant cells are categorized as S-Pop, S-Pop/Rhodamine or Hoescht$^{dim}$, S-Pop/Rhodamine or Hoescht$^{bright}$, Forward scatter (FSc), FSc/Rhodamine or Hoescht$^{dim}$, FSc/Rhodamine or Hoesch$^{bright}$.

Cancer cells are subsequently stimulated in a third round of selection, which is significant because it assists in understanding how a cancer stem cell could convert into an aggressive phenotype and form progenitors that metastasize to tertiary sites. Clones that have been narrowed as potential cancer stem cells are used. Cells are always re-cultured with the anti-cancer agents prior to assays so as to be certain that the experiments are performed with clones that are resistant to the high concentration of drugs. Cells are then studied to determine if they can be stimulated to self-renew and also form cancer progenitors.

To test the self-renewal properties and asymmetry of the cancer stem cells, assays begin with 1-15 cells at 1 cell/well in 96-well plates using a modified technique for asymmetry, self-renewal and pluripotency. Cells are plated in wells containing irradiated feeder cells, preferable the bone marrow stroma/fibroblasts or MSC identified above. Appropriate media is added to each well and cell division is observed with an inverted microscope. The time of cells division is documented and after about twenty generations, the cells per well are counted. Because the cells will be adherent, cell counting is done in wells from a parallel culture in order to allow for the enumeration of the cells after labeling with FITC-conjugated anti-cytokeratin.

To separate the cancer cells from feeder cells, magnetic beads coupled to anti-cytokeratin are used and then the breast cancer cells are separated from the feeder cells. After this, it is determined if the cells from each well consist of progenitors by limiting dilutions of 1 cell/well of 6-well plates without feeder cells. The reason that feeder cells are omitted is because progenitors will be able to divide without feeder cells. Cells from 6-well plates are counted and some used for cell cycle analyses (propidium iodide method) and colony formation in methylcellulose.

The results of this experiment are that cells are not lost and there is even an increase of a few cells, if the starting population truly represents the stem cell subset within the cancer because the cancer stem cells self-renew. There are typically one or few wells in the E-well plates where the cells could not proliferate without feeder due to long doubling time. These cells are selected as cancer stem cells. The asymmetry of cancer stem cells may be studied by membrane dye resolution of PKH-26. Clones are labeled with PKH-26 and then cultured on feeder cells at 1 cell/well in 96-well plates and the cells are examined at 3 hour intervals. Cell division is based on the intensities of the dye.

Another experiment further dissects cancer stem cells and progenitors at both the entry and seeding stages. Entry studies analyze the movement of cancer stem cells and progenitors in bone marrow through endothelial cells, using MSC as facilitators. Seeding studies analyze co-cultures of bone marrow stroma and cancer stem cells or cancer progenitors. The assay uses the Boyden Chamber method described above. Three groups of cultures contain cancer progenitors, cancer stem cells and heterogeneous population. Preferably, the assay uses HUVEC. Because endothelial cell functions may vary depending on the source, endothelial cells will be isolated from bone marrow aspirate and also differentiated from progenitor cells.

Transmigration through transwell cultures is determined by looking for cells in the outer well and at the bottom/outer membrane of the insert. Membranes are stained with methylene blue and then counted. In parallel membranes, cells are dislodged with EDTA and then pooled with those in the outer media for immunofluorescence. In the event that the breast cancer cells are complexed to MSC, the cells are labeled with perform 2-color immunofluorescence for MSC(SH2/CD105) and breast cancer (cytokeratin). The labeled cells are examined by flow cytometry and microscopically. The microscopic examination is performed on slides so as to avoid the cell complexes to dislodge.

Primary cultures of endothelial cells and endothelial progenitors are known in the art. Endothelial cells are established with bone marrow mononuclear cells and endothelial progenitors are established from purified CD34+ cells. Endothelial cells are isolated because they can be retrieved from cryopreservation with better efficiency. Furthermore, they undergo more than 15 doubling times before senescence.

To understand early metastasis to the bone marrow, the relationships between bone marrow stroma and cancer cells must be defined. Cultures of stroma at different confluences are added cancer progenitors or cancer stem cells. The growth pattern (monolayer vs. colony formation using stroma as feeder cells) is documented with an inverted microscope attached to a digital camera. Growth curves are performed for stroma and breast cancer cells using two methods: (A) Separation of the two cell populations at different times with microbeads to do cell counts and (B) Labeling cells with two different fluorescent membrane dyes and then using flow cytometry to quantitate cell doubling at different times, to be determined by the dilution of membrane dyes.

The next set of experiments determines the roles of HGFIN and PPT-1 in early entry of breast cancer cells in the bone marrow and begins to uncover the mechanisms for crosstalk among endothelial cells, MSC, and breast cancer cells during entry of breast cancer cells in the bone marrow. TRANSWELL cultures are established, but instead of breast cancer cells, breast cancer cell lines with HGFIN overexpressed will be used. There is no efficient transmigration of these cells because in three breast cancer cell lines, overexpression of HGFIN showed functions consistent with non-transformed breast cells. The second cell line overexpresses PPT-1 in non-transformed breast cells (n=4), resulting in PPT-1 to transform cells to malignant phenotypes and HGFIN to show functions consistent for a tumor suppressor gene. The functions (malignant vs. non-transformed) result in the movement of the cells across endothelial cells.

A TRANSWELL culture employs heterogenous breast cancer cells and the wells are larger so as to retrieve sufficient cells for RNA extraction. These studies help explain how the breast cancer cells, endothelial cells, and MSC communicate. The following microarrays are used: transcriptional factors, cytokines/chemokines, cell-cycle-specific, angiogenesis and extracellular matrix proteins. Genes that show compelling evidence (>1.5-fold) that they are relevant for breast cancer cell movement are verified by different methods: Northern analyses, western, and/or ELISA. For the experimental period, the cause-effect relationship is employed on genes that provide a global 'picture' on the mechanisms by using knock-in and/or knockout genes, e.g., expression of genes, expression of dominant negative genes, siRNA strategies. Finally, animal models are employed to determine the level of metastasis by the cancer cell subsets and to determine the role of particular gene(s) in metastasis of cell subsets.

Example 9

In Vivo Activity of HGFIN to Inhibit Tumor Growth

Female athymic BALB/c mice (4 weeks) were obtained from Harlan Laboratories (Somerville, N.J.) and housed in a laminar flow hood at an AAALAC-accredited facility. The use of mice was approved by the Institutional Animal Care and Use Committee, New Jersey Medical School (Newark, N.J.).

Mice were inoculated with Oct4(hi) breast cancer cells that had been identified as expressing high levels of HGFIN. Another group of nude BALE/c mice was inoculated with Oct4 cells where HGFIN expression was knocked down with siRNA. The cells were injected in a total volume of 0.2 mL subcutaneously in the dorsal flanks. Tumors were monitored daily and measured in two dimensions with a caliper and volume was calculated using the formula $V=\pi r^2 h$, where r=radius and h=height.

After five days of palpating tumors and measuring tumor volume, the tumor size in HGFIN knockdown mice had increased at a significantly more rapid pace as compared to mice with high expressing Oct4 cells injected with mutant siRNA. These data demonstrate that HGFIN activity can be targeted and affect tumor cell growth in vivo, where inhibition of tumor cell growth results when HGFIN expression or activity is present or increased.

These data provide direct evidence that HGFIN is active in vivo as a tumor suppressor gene in breast cancer cells. Moreover, these data provide in vivo evidence that contacting a breast cancer cell with an effective amount of HGFIN inhibits breast cancer cell growth.

Example 10

Knock Down of HGFIN Activity Reverses Carboplatin Resistance in Breast Cancer by Affecting Breast Cancer Cell Differentiation As discussed above, female athymic BALB/c mice (4 weeks) were obtained from Harlan Laboratories (Somerville, N.J.) and housed in a laminar flow hood at an AAALAC-accredited facility. The use of mice was approved by the Institutional Animal Care and Use Committee, New Jersey Medical School (Newark, N.J.).

Mice were inoculated with Oct4 cells where HGFIN expression was knocked down with siRNA. The cells were injected in a total volume of 0.2 mL subcutaneously in the dorsal flanks. Tumors were monitored daily and measured in two dimensions with a caliper and volume was calculated using the formula $V=\pi r^2 h$, where r=radius and h=height. Animal were injected with carboplatin (50 mg/kg) on day 0 and day 3 of the test period. Tumors were palpated and tumor volume was measured every other day for two weeks (i.e., days 0, 2, 4, 6, 8, 10, 12 and 14). The tumors grew rapidly and were more sensitive to carboplatin two weeks after the second carboplatin injection. This study indicates that HGFIN can be targeted to eradicate the most difficult cancer cells. Thus, these data are evidence that inhibition of HGFIN activity or expression in breast cancer stem cells affected cell differentiation and reversed drug resistance.

Although carboplatin was used to demonstrate the effects of HGFIN knockdown on drug resistance, other drugs typically used for treatment of solid tumors may be employed. These drugs would be any drug known by one of skill in the art to be effective in cancer therapy and would include but not be limited to drugs that are currently approved for cancer treatment by the U.S. Food and Drug Administration. Also contemplated would be drugs found in the future to be useful for inhibition of tumor growth and approved for use in humans. Doses of the drugs to be used would be those typically used to treat solid tumors and would be known to one of skill in the art based on reference to the regulatory body approved drug labeling for a drug such as are found in the Physician's Desk Reference (PDR).

What is claimed is:

1. A method for reversing carboplatin resistance in breast cancer cells comprising contacting carboplatin-resistant breast cancer cells with a hematopoietic growth factor-inducible neurokinin-1 (HGFIN)-specific siRNA in combination with carboplatin, wherein contacting said breast cancer cells with the HGFIN-specific siRNA and carboplatin results in inhibition of breast cancer cell growth.

* * * * *

SEQUENCE LISTING

<160> NUMBER OF SEQ ID NOS: 18

<210> SEQ ID NO 1
<211> LENGTH: 2661
<212> TYPE: DNA
<213> ORGANISM: Homo sapiens

<400> SEQUENCE: 1

```
cggcacgagg gcccagagga ataagttaac cttggtgcct gcgtccgtga gaattcagca      60
tggaatgtct ctactatttc ctgggatttc tgctcctggc tgcaagattg ccacttgatg     120
ccgccaaacg atttcatgat gtgctgggca atgaaagacc ttctgcttac atgagggagc     180
acaatcaatt aaatggctgg tcttctgatg aaaatgactg gaatgaaaaa ctctacccag     240
tgtggaagcg gggagacatg aggtggaaaa actcctggaa gggaggccgt gtgcaggcgg     300
tcctgaccag tgactcacca gccctcgtgg gctcaaatat aacatttgcg gtgaacctga     360
tattccctag atgccaaaag gaagatgcca atggcaacat agtctatgag aagaactgca     420
gaaatgaggc tggtttatct gctgatccat atgtttacaa ctggacagca tggtcagagg     480
acagtgacgg ggaaaatggc accggccaaa gccatcataa cgtcttccct gatgggaaac     540
cttttcctca ccaccccgga tggagaagat ggaatttcat ctacgtcttc cacacacttg     600
gtcagtattt ccagaaattg ggacgatgtt cagtgagagt ttctgtgaac acagccaatg     660
tgacacttgg gcctcaactc atggaagtga ctgtctacag aagacatgga cgggcatatg     720
ttcccatcgc acaagtgaaa gatgtgtacg tggtaacaga tcagattcct gtgtttgtga     780
ctatgttcca gaagaacgat cgaaattcat ccgacgaaac cttcccaaag atctccccat     840
tatgtttgat gtcctgattc atgatcctag ccacttcctc aattattcta ccattaacta     900
caagtggagc ttcggggata atactggcct gtttgtttcc accaatcata ctgtgaatca     960
cacgtatgtg ctcaatggaa ccttcagcct taacctcact gtgaaagctg cagcaccagg    1020
accttgtccg ccaccgccac caccaccagg accttcaaaa cccaccccctt ctttaggacc    1080 tgctggtgac aaccccctgg agctgagtag gattcctgat gaaaactgcc agattaacag    1140
atatggccac tttcaagcca ccatcacaat tgtagaggga atcttagagg ttaacatcat    1200
ccagatgaca gacgtcctga tgccggtgcc atggcctgaa agctccctaa tagactttgt    1260
cgtgacctgc caagggagca ttcccacgga ggtctgtacc atcatttctg accccacctg    1320
cgagatcacc cagaacacag tctgcagccc tgtggatgtg gatgagatgt gtctgctgac    1380
tgtgagacga accttcaatg ggtctgggac gtactgtgtg aacctcaccc tgggggatga    1440
cacaagcctg gctctcacga gcaccctgat ttctgttcct gacagagacc cagcctcgcc    1500
tttaaggatg gcaaacagtg ccctgatctc cgttggctgc ttggccatat ttgtcactgt    1560
```

-continued

```
gatctccctc ttggtgtaca aaaaacacaa ggaatacaac ccaatagaaa atagtcctgg    1620
gaatgtggtc agaagcaaag gcctgagtgt ctttctcaac cgtgcaaaag ccgtgttctt    1680
cccgggaaac caggaaaagg atccgctact caaaaaccaa gaatttaaag gagtttctta    1740
aatttcgacc ttgtttctga agctcacttt tcagtgccat tgatgtgaga gtgctggag    1800 tggctattaa cctttttttc ctaaagatta ttgttaaata gatattgtgg tttggggaag    1860
ttgaattttt tataggttaa atgtcatttt agagatgggg agagggatta tactgcaggc    1920
agcttcagcc atgttgtgaa actgataaaa gcaacttagc aaggcttctt ttcattattt    1980
tttatgtttc acttataaag tcttaggtaa ctagtaggat agaaacactg tgtcccgaga    2040
gtaaggagag aagctactat tgattagagc ctaacccagg ttaactgcaa gaagaggcgg    2100
gatactttca gctttccatg taactgtatg cataaagcca atgtagtcca gtttctaaga    2160
tcatgttcca agctaactga atcccacttc aatacacact catgaactcc tgatggaaca    2220
ataacaggcc caagcctgtg gtatgatgtg cacacttgct agactcagaa aaaatactac    2280
tctcataaat gggtgggagt attttggtga caacctactt tgcttggctg agtgaaggaa    2340
tgatattcat atattcattt attccatgga catttagtta gtgcttttta tataccaggc    2400
atgatgctga gtgacactct tgtgtatatt tccaaatttt tgtatagtcg ctgcacatat    2460
ttgaaatcaa aatattaaga cttttccaaa atttggtccc tggttttca tggcaacttg    2520 atcagtaagg atttcccctc tgtttggaac taaaaccatt tactatatgt tagacaagac    2580
attttttttt tttccttcct gaaaaaaaaa tgagggaaga gacaaaaaaa aaaaaaaaa    2640 aaaaaaaaaa aaaaaaaaa a                                              2661
```

<210> SEQ ID NO 2
<211> LENGTH: 560
<212> TYPE: PRT
<213> ORGANISM: Homo sapiens

<400> SEQUENCE: 2

```
Met Glu Cys Leu Tyr Tyr Phe Leu Gly Phe Leu Leu Leu Ala Ala Arg
1               5                   10                  15

Leu Pro Leu Asp Ala Ala Lys Arg Phe His Asp Val Leu Gly Asn Glu
                20                  25                  30

Arg Pro Ser Ala Tyr Met Arg Glu His Asn Gln Leu Asn Gly Trp Ser
            35                  40                  45

Ser Asp Glu Asn Asp Trp Asn Glu Lys Leu Tyr Pro Val Trp Lys Arg
        50                  55                  60

Gly Asp Met Arg Trp Lys Asn Ser Trp Lys Gly Gly Arg Val Gln Ala
65                  70                  75                  80

Val Leu Thr Ser Asp Ser Pro Ala Leu Val Gly Ser Asn Ile Thr Phe
                85                  90                  95

Ala Val Asn Leu Ile Phe Pro Arg Cys Gln Lys Glu Asp Ala Asn Gly
            100                 105                 110

Asn Ile Val Tyr Glu Lys Asn Cys Arg Asn Glu Ala Gly Leu Ser Ala
        115                 120                 125

Asp Pro Tyr Val Tyr Asn Trp Thr Ala Trp Ser Glu Asp Ser Asp Gly
    130                 135                 140

Glu Asn Gly Thr Gly Gln Ser His His Asn Val Phe Pro Asp Gly Lys
145                 150                 155                 160

Pro Phe Pro His His Pro Gly Trp Arg Arg Trp Asn Phe Ile Tyr Val
                165                 170                 175

Phe His Thr Leu Gly Gln Tyr Phe Gln Lys Leu Gly Arg Cys Ser Val
```

180                 185                 190
Arg Val Ser Val Asn Thr Ala Asn Val Thr Leu Gly Pro Gln Leu Met
            195                 200                 205
Glu Val Thr Val Tyr Arg Arg His Gly Arg Ala Tyr Val Pro Ile Ala
        210                 215                 220
Gln Val Lys Asp Val Tyr Val Thr Asp Gln Ile Pro Val Phe Val
225                 230                 235                 240
Thr Met Phe Gln Lys Asn Asp Arg Asn Ser Ser Asp Glu Thr Phe Leu
                245                 250                 255
Lys Asp Leu Pro Ile Met Phe Asp Val Leu Ile His Asp Pro Ser His
            260                 265                 270
Phe Leu Asn Tyr Ser Thr Ile Asn Tyr Lys Trp Ser Phe Gly Asp Asn
        275                 280                 285
Thr Gly Leu Phe Val Ser Thr Asn His Thr Val Asn His Thr Tyr Val
    290                 295                 300
Leu Asn Gly Thr Phe Ser Leu Asn Leu Thr Val Lys Ala Ala Ala Pro
305                 310                 315                 320
Gly Pro Cys Pro Pro Pro Pro Pro Arg Pro Ser Lys Pro Thr
                325                 330                 335
Pro Ser Leu Gly Pro Ala Gly Asp Asn Pro Leu Glu Leu Ser Arg Ile
            340                 345                 350
Pro Asp Glu Asn Cys Gln Ile Asn Arg Tyr Gly His Phe Gln Ala Thr
        355                 360                 365
Ile Thr Ile Val Glu Gly Ile Leu Glu Val Asn Ile Ile Gln Met Thr
    370                 375                 380
Asp Val Leu Met Pro Val Pro Trp Pro Glu Ser Ser Leu Ile Asp Phe
385                 390                 395                 400
Val Val Thr Cys Gln Gly Ser Ile Pro Thr Glu Val Cys Thr Ile Ile
                405                 410                 415
Ser Asp Pro Thr Cys Glu Ile Thr Gln Asn Thr Val Cys Ser Pro Val
            420                 425                 430
Asp Val Asp Glu Met Cys Leu Leu Thr Val Arg Arg Thr Phe Asn Gly
        435                 440                 445
Ser Gly Thr Tyr Cys Val Asn Leu Thr Leu Gly Asp Asp Thr Ser Leu
    450                 455                 460
Ala Leu Thr Ser Thr Leu Ile Ser Val Pro Asp Arg Asp Pro Ala Ser
465                 470                 475                 480
Pro Leu Arg Met Ala Asn Ser Ala Leu Ile Ser Val Gly Cys Leu Ala
                485                 490                 495
Ile Phe Val Thr Val Ile Ser Leu Leu Val Tyr Lys Lys His Lys Glu
            500                 505                 510
Tyr Asn Pro Ile Glu Asn Ser Pro Gly Asn Val Val Arg Ser Lys Gly
        515                 520                 525
Leu Ser Val Phe Leu Asn Arg Ala Lys Ala Val Phe Phe Pro Gly Asn
    530                 535                 540
Gln Glu Lys Asp Pro Leu Leu Lys Asn Gln Glu Phe Lys Gly Val Ser
545                 550                 555                 560

<210> SEQ ID NO 3
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 3

```
ccggtgccaa gcgcacct                                                  18

<210> SEQ ID NO 4
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 4
cgcttattca gccacacag                                                 19

<210> SEQ ID NO 5
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 5
ggtgcaggga aggaaaaaag ac                                             22

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 6
tagagacatt ccatgctgaa                                                20

<210> SEQ ID NO 7
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 7
ctcgaggtgc agggaaggaa a                                              21

<210> SEQ ID NO 8
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 8
aagctttcca tgctgaattc c                                              21

<210> SEQ ID NO 9
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 9
catttgcggt gaacctgat                                                 19

<210> SEQ ID NO 10
<211> LENGTH: 18
<212> TYPE: DNA
<213> ORGANISM: Artificial Sequence
```

```
<220> FEATURE:
<223> OTHER INFORMATION: Synthetic oligonucleotide

<400> SEQUENCE: 10
ccacttgatg ccgccaaa                                                 18

<210> SEQ ID NO 11
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 11
atggcaccgg ccaaagcc                                                 18

<210> SEQ ID NO 12
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 12
gcctgtggta tgatgtgc                                                 18

<210> SEQ ID NO 13
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 13
aaccttttcc tcaccaccc                                                19

<210> SEQ ID NO 14
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 14
ttcacagaaa ctctcactga ac                                            22

<210> SEQ ID NO 15
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 15
ccacccatgg caaattccat ggca                                          24

<210> SEQ ID NO 16
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 16
tctagacggc aggtcaggtc cacc                                          24
```

```
<210> SEQ ID NO 17
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 17
cggggtacca tggaatgtct ctacta                                          26

<210> SEQ ID NO 18
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 18
ccggaattct cgaaatttaa gaaact                                          26
```